(12) United States Patent  (10) Patent No.: US 7,745,446 B2
Maier et al.                 (45) Date of Patent:     Jun. 29, 2010

(54) PYRAZOLO[1,5-C]PYRIMIDINES

(75) Inventors: Thomas Maier, Stockach (DE); Armin Zuelch, Constance (DE); Thomas Ciossek, Ravensburg (DE); Thomas Baer, Reichenau (DE); Thomas Beckers, Constance (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 707 days.

(21) Appl. No.: 11/661,111

(22) PCT Filed: Sep. 5, 2005

(86) PCT No.: PCT/EP2005/054366

§ 371 (c)(1),
(2), (4) Date: Feb. 26, 2007

(87) PCT Pub. No.: WO2006/027346

PCT Pub. Date: Mar. 16, 2006

(65) Prior Publication Data

US 2007/0254046 A1    Nov. 1, 2007

(30) Foreign Application Priority Data

Sep. 6, 2004 (EP) .................. 04104283

(51) Int. Cl.
C07D 487/04 (2006.01)
A61K 31/519 (2006.01)
A61P 35/04 (2006.01)
A61P 35/02 (2006.01)

(52) U.S. Cl. ..................... 514/259.3; 544/281
(58) Field of Classification Search ................. 544/281; 514/259.3
See application file for complete search history.

(56) References Cited

U.S. PATENT DOCUMENTS

| 5,859,205 | A | 1/1999 | Adair et al. |
| 6,235,741 | B1 | 5/2001 | Bilodeau et al. |
| 2003/0180924 | A1 | 9/2003 | DeSimone |
| 2004/0116432 | A1 | 6/2004 | Carling et al. |

FOREIGN PATENT DOCUMENTS

| EP | 0 464 533 | 7/1998 |
| EP | 1 348 707 | 10/2003 |
| WO | 94/18215 | 8/1994 |
| WO | 00/53605 | 9/2000 |
| WO | 03/029209 | 4/2003 |
| WO | 03/033499 | 4/2003 |
| WO | 03/080064 | 10/2003 |
| WO | 03/099820 | 12/2003 |
| WO | 2004/002255 | 1/2004 |
| WO | 2004/009596 | 1/2004 |
| WO | 2004/009597 | 1/2004 |
| WO | 2004/009602 | 1/2004 |
| WO | 2004/022062 | 3/2004 |
| WO | 2004/022560 | 3/2004 |
| WO | 2004/022561 | 3/2004 |
| WO | 2004/026229 | 4/2004 |
| WO | 2004/030671 | 4/2004 |
| WO | 2004/063195 | 7/2004 |
| WO | 2004/087707 | 10/2004 |

*Primary Examiner*—Susanna Moore
(74) *Attorney, Agent, or Firm*—The Nath Law Group; Joshua B. Goldberg; Sheldon M. McGee

(57) ABSTRACT

Compounds of a certain formula I

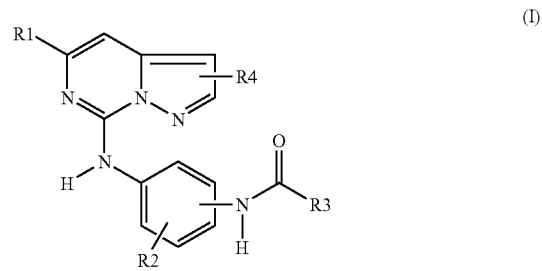

in which R1, R2, R3 and R4 have the meanings indicated in the description are novel compounds expected to be useful in the therapy of (hyper)proliferative diseases and/or disorders responsive to induction of apoptosis.

14 Claims, No Drawings

PYRAZOLO[1,5-C]PYRIMIDINES

This application was filed under 35 U.S.C. 371 as a national stage of PCT/EP2005/054366, filed Sep. 5, 2005.

FIELD OF APPLICATION OF THE INVENTION

The invention relates to a novel class of pyrazolopyrimidine derivatives, which can be used in the pharmaceutical industry for the production of pharmaceutical compositions.

PRIOR ART

Pyrazolopyrimidines of certain condensation patterns are known from a variety of patent applications or patents, such as WO 2004026229, WO 2004022561, WO 2004022560, WO 200402255, WO 2004022062, WO 2004009602, WO 2004009597, WO 2004009596, WO2004087707, WO 2003099820, WO 2003080064, EP 1348707, US 2003180924, WO 2003033499, WO 2003029209, WO 2000053605, WO 9418215 and U.S. Pat. No. 6,235,741.

It is further known that compounds of some pyrazolopyrimidine classes can act as kinase inhibitors.

However, compounds containing specifically a pyrazolo[1,5-c]pyrimidine scaffold have not been described as protein kinase inhibitors.

DESCRIPTION OF THE INVENTION

It has now been found that the pyrazolo[1,5-c]pyrimidine derivatives, which are described in greater details below, represent a structurally novel class of pharmaceutically valueable compounds and have surprising and particularly advantageous properties.

Thus, for example, pyrazolopyrimidine derivatives according to this invention can act as inhibitors of protein kinase B (PKB)/Akt.

The invention thus relates, in a first aspect (aspect A) to compounds of formula I

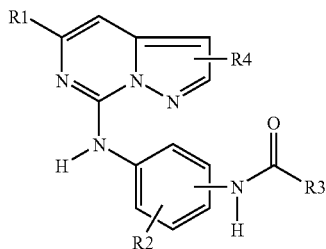

in which
R1 is Ar1, or
   Har1, Har2 or Har3, or
   Cyc1, or
   Hh1, Ah1 or Ha1, in which
Ar1 is optionally substituted by R11, and is phenyl, naphthyl, fluorenyl or Aa1, in which
Aa1 is a bisaryl radical made up of two aryl groups, which are selected independently from a group consisting of phenyl and naphthyl, and which are linked together via a single bond,
R11 is 1-4C-alkoxy, 1-4C-alkoxy-2-4C-alkoxy, halogen, nitro, hydroxyl, phenoxy, phenyl-1-4C-alkoxy, hydroxy-2-4C-alkoxy, carboxy-1-4C-alkoxy or 1-4C-alkylcarbonylamino,
Har1 is optionally substituted by R12, and is an unsaturated monocyclic 5- or 6-membered heteroaryl radical comprising one to four heteroatoms, each of which is selected from the group consisting of nitrogen, oxygen and sulphur, in which
R12 is 1-4C-alkyl,
Har2 is optionally substituted by R13, and is an unsaturated fused bicyclic 9- or 10-membered heteroaryl radical comprising one to four heteroatoms, each of which is selected from the group consisting of nitrogen, oxygen and sulphur, in which
R13 is 1-4C-alkyl,
Har3 is optionally substituted by R14, and is an unsaturated fused tricyclic 13- or 14-membered heteroaryl radical comprising one to four heteroatoms, each of which is selected from the group consisting of nitrogen, oxygen and sulphur, in which
R14 is 1-4C-alkyl,
Cyc1 is a group of formula A

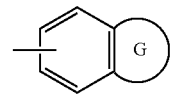

in which
G is a 5- or 6-membered saturated or partially unsaturated heterocyclic ring comprising one or two heteroatoms independently selected from the group consisting of oxygen and sulfur, whereby said Cyc1 ring system is attached to the parent molecular group via any substitutable benzoring carbon atom,
Hh1 is optionally substituted by R15, and is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond, in which
R15 is 1-4C-alkyl,
Ah1 is optionally substituted by R16, and is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, in which
R16 is 1-4C-alkyl,
Ha1 is optionally substituted by R17, and is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, in which
R17 is 1-4C-alkyl, whereby each of the radicals Har1, Har2, Har3, Hh1 and Ah1 is bonded via a ring carbon atom to the pyrazolopyrimidine scaffold;

R2 is hydrogen, halogen or 1-4C-alkyl;

R3 is -T-R30, —U—Ar2, -V-Har4, or Cyc2, in which

T is 1-4C-alkylene,

R30 is —N(R301)R302, cyano, amidino, carbamoyl, guanidino, ureido, 1-4C-alkylsulfonyl, or Het2, in which R301 is hydrogen, 1-4C-alkyl, 1-4C-alkoxycarbonyl, hydroxy-2-4C-alkyl or 1-4C-alkoxy-2-4C-alkyl, R302 is hydrogen or 1-4C-alkyl, or R301 and R302 together an with inclusion of the nitrogen atom to which they are bonded form a radical Het1, in which Het1 is a monocylic 3- to 7-membered saturated heterocyclic ring comprising the nitrogen atom, to which R301 and R302 are attached, and optionally one further heteroatom selected from a group consisting of oxygen, nitrogen, N(R303) and sulfur, in which R303 is hydrogen, 1-4C-alkyl or 1-4C-alkoxycarbonyl, Het2 is a monocylic 3- to 7-membered saturated heterocyclic ring,
which comprises one nitrogen atom and optionally one further heteroatom selected from a group consisting of oxygen, nitrogen, N(R304) and sulfur,
whereby said Het2 radical is attached to the parent molecular group via a ring carbon atom, in which R304 is 1-4C-alkyl, U is a bond, 1-4C-alkylene, or 1-4C-alkylene substituted with amino-1-4C-alkyl, Ar2 is phenyl, or R31- and/or R32-substituted phenyl, in which R31 is 1-4C-alkyl, 1-4C-alkoxy, halogen, trifluoromethyl, or —W—R311, in which W is a bond or 1-4C-alkylene, R311 has one of the meanings of R30 as defined afore, R32 is halogen, V is a bond, Har4 is optionally substituted by R33, and is a monocyclic or fused bicyclic 5- to 10-membered unsaturated heteroaryl radical comprising one to four heteroatoms, each of which is selected from the group consisting of nitrogen, oxygen and sulfur, whereby said Har4 radical is attached to the moiety V via a ring carbon atom, in which R33 is -Z-R331, in which Z is 1-4C-alkylene, R331 has one of the meanings of —N(R301)R302 as defined afore, Cyc2 is a group of formula A (A)

in which

G is a 5- or 6-membered saturated heterocyclic ring comprising one nitrogen atom and optionally one further heteroatom selected from the group consisting of oxygen, nitrogen and sulfur, whereby said Cyc2 ring system is attached to the parent molecular group via any substitutable benzoring carbon atom;

R4 is hydrogen or halogen;

and the salts of these compounds.

The invention relates in a second aspect (aspect B), which is an embodiment of aspect A, to compounds of formula Ia

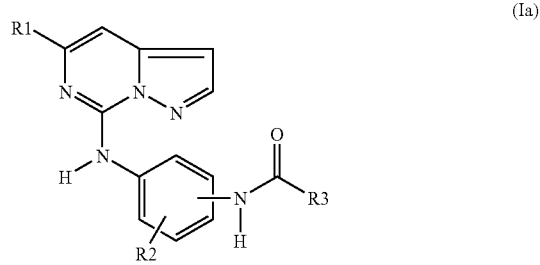

(Ia)

in which

R1 is Ar1, or
  Har1, Har2 or Har3, or
  Cyc1, or
  Hh1, Ah1 or Ha1, in which

Ar1 is optionally substituted by R11, and is phenyl, naphthyl, fluorenyl or Aa1, in which Aa1 is a bisaryl radical made up of two aryl groups, which are selected independently from a group consisting of phenyl and naphthyl, and which are linked together via a single bond, R11 is 1-4C-alkoxy, 1-4C-alkoxy-2-4C-alkoxy, halogen, hydroxyl, phenoxy, phenyl-1-4C-alkoxy, hydroxy-2-4C-alkoxy, carboxy-1-4C-alkoxy or 1-4C-alkylcarbonylamino, Har1 is optionally substituted by R12, and is an unsaturated monocyclic 5-or 6-membered heteroaryl radical comprising one to four heteroatoms, each of which is selected from the group consisting of nitrogen, oxygen and sulphur, in which R12 is 1-4C-alkyl, Har2 is optionally substituted by R13, and is an unsaturated fused bicyclic 9-or 10-membered heteroaryl radical comprising one to four heteroatoms, each of which is selected from the group consisting of nitrogen, oxygen and sulphur, in which R13 is 1-4C-alkyl, Har3 is optionally substituted by R14, and is an unsaturated fused tricyclic 13-or 14-membered heteroaryl radical comprising one to four heteroatoms, each of which is selected from the group consisting of nitrogen, oxygen and sulphur, in which R14 is 1-4C-alkyl, Cyc1 is a group of formula A (A)

in which

G is a 5- or 6-membered saturated or partially unsaturated heterocyclic ring comprising one or two heteroatoms independently selected from the group consisting of oxygen and sulfur, whereby said Cyc1 ring system is attached to the parent molecular group via any substitutable benzoring carbon atom, Hh1 is optionally substituted by R15, and is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond, in which R15 is 1-4C-alkyl, Ah1 is optionally substituted by R16, and is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, in which R16 is 1-4C-alkyl, Ha1 is optionally substituted by R17, and is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, in which R17 is 1-4C-alkyl, whereby each of the radicals Har1, Har2, Har3, Hh1 and Ah1 is bonded via a ring carbon atom to the pyrazolopyrimidine scaffold;

R2 is hydrogen, halogen or 1-4C-alkyl;

R3 is -T-R30, —U—Ar2, -V-Har4, or Cyc2, in which

T is 1-4C-alkylene,

R30 is —N(R301)R302, cyano, amidino, carbamoyl, guanidino, ureido, or Het2, in which R301 is hydrogen, 1-4C-alkyl, 1-4C-alkoxycarbonyl, hydroxy-2-4C-alkyl or 1-4C-alkoxy-2-4C-alkyl, R302 is hydrogen or 1-4C-alkyl, or R301 and R302 together an with inclusion of the nitrogen atom to which they are bonded form a radical Het1, in which Het1 is a monocylic 3- to 7-membered saturated heterocyclic ring comprising the nitrogen atom, to which R301 and R302 are attached, and optionally one further heteroatom selected from a group consisting of oxygen, nitrogen, N(R303) and sulfur, in which R303 is hydrogen, 1-4C-alkyl or 1-4C-alkoxycarbonyl, Het2 is a monocylic 3- to 7-membered saturated heterocyclic ring,
which comprises one nitrogen atom and optionally one further heteroatom selected from a group consisting of oxygen, nitrogen, N(R304) and sulfur,
whereby said Het2 radical is attached to the parent molecular group via a ring carbon atom, in which R304 is 1-4C-alkyl, U is a bond, 1-4C-alkylene, or 1-4C-alkylene substituted with amino-1-4C-alkyl, Ar2 is phenyl, or R31- and/or R32-substituted phenyl, in which R31 is 1-4C-alkyl, 1-4C-alkoxy, halogen, trifluoromethyl, or —W—R311, in which W is a bond or 1-4C-alkylene, R311 has one of the meanings of R30 as defined afore, R32 is halogen, V is a bond, Har4 is optionally substituted by R33, and is a monocyclic or fused bicyclic 5- to 10-membered unsaturated heteroaryl radical comprising one to four heteroatoms, each of which is selected from the group consisting of nitrogen, oxygen and sulfur, whereby said Har4 radical is attached to the moiety V via a ring carbon atom, in which R33 is -Z-R331, in which Z is 1-4C-alkylene, R331 has one of the meanings of —N(R301)R302 as defined afore, Cyc2 is a group of formula A

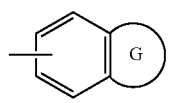

(A)

in which

G is a 5- or 6-membered saturated heterocyclic ring comprising one nitrogen atom and optionally one further heteroatom selected from the group consisting of oxygen, nitrogen and sulfur, whereby said Cyc2 ring system is attached to the parent molecular group via any substitutable benzoring carbon atom;

and the salts of these compounds.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

Halogen within the meaning of the present invention is iodine or, in particular, bromine, chlorine or fluorine.

Naphthyl, alone or as part of another group, includes naphthalen-1-yl and naphthalen-2-yl.

1-4C-Alkylene is a straight or branched chain alkylene radical having 1 to 4 carbon atoms. Examples which may be mentioned as straight chain alkylene radicals are the methylene (—CH$_2$—), ethylene (—CH$_2$—CH$_2$—), trimethylene (—CH$_2$—CH$_2$—CH$_2$—) and tetramethylene (—CH$_2$—CH$_2$—CH$_2$—CH$_2$—) radical. An example which may be mentioned as branched chain alkylene radical is the 1,1-dimethyl-methylene radical.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and preferably the ethoxy radical.

1-4C-Alkoxy-2-4C-alkoxy represents one of the abovementioned 2-4C-alkoxy radicals, which is substituted by one of the abovementioned 1-4C-alkoxy radicals. Examples which may be mentioned are the 2-methoxyethoxy, 2-ethoxyethoxy and the 2-isopropoxyethoxy radicals.

Hydroxy-2-4C-alkoxy represents one of the abovementioned 2-4C-alkoxy radicals, which is substituted by a hydroxyl radical. Examples which may be mentioned are the 2-hydroxyethoxy and the 3-hydroxypropoxy radicals.

Carboxy-1-4C-alkoxy represents one of the abovementioned 1-4C-alkoxy radicals, which is substituted by a carboxyl radical. Examples which may be mentioned are the carboxy-methoxy, the 2-carboxy-ethoxy and the 3-carboxypropoxy radicals.

Phenyl-1-4C-alkoxy represents one of the abovementioned 1-4C-alkoxy radicals, which is substituted by a phenyl radical. Examples which may be mentioned are the phenethoxy and the benzyloxy radicals.

1-4C-Alkoxy-2-4C-alkyl represents one of the abovementioned 2-4C-alkyl radicals, which is substituted by one of the abovementioned 1-4C-alkoxy radicals. Examples which may be mentioned are the 2-methoxyethyl, 2-ethoxyethyl and the 2-isopropoxyethyl radicals.

Hydroxy-2-4C-alkyl represents one of the abovementioned 2-4C-alkyl radicals, which is substituted by a hydroxy radical. Examples which may be mentioned are the 2-hydroxyethyl and the 3-hydroxypropyl radicals.

Amino-1-4C-alkyl represents one of the abovementioned 1-4C-alkyl radicals, which is substituted by an amino radical. Examples which may be mentioned are the aminomethyl, 2-aminoethyl and the 3-aminopropyl radicals.

"1-4C-Alkylene substituted with amino-1-4C-alkyl" may include, for example, one of the abovementioned 1-4C-alkylene radicals, particularly one of the abovementioned straight chain alkylene radicals, which is substituted by one of the abovementioned amino-1-4C-alkyl radicals, such as, for example, the amino-1-4C-alkyl-methylene radicals, e.g. the aminomethyl-methylene or the 2-aminoethyl-methylene radical. The radical 1-4C-alkylene substituted with amino-1-4C-alkyl is bonded to the adjacent molecular groups via its 1-4C-alkylene moiety.

1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the tertbutoxycarbonyl radicals.

An 1-4C-Alkylcarbonylamino radical is, for example, the propionylamino ($C_3H_7C(O)NH-$) and the acetylamino radical ($CH_3C(O)NH-$).

1-4C-Alkylsulfonyl is a sulfonyl group to which one of the abovementioned 1-4C-alkyl radicals is bonded. An example is the methanesulfonyl radical ($CH_3SO_2-$).

In the meaning of the present invention, it is to be understood, that, when two structural portions of the compounds according to this invention are linked via a constituent which has the meaning "bond", then said two portions are directly attached to another via a single bond.

Aa1 is a bisaryl radical made up of two aryl groups, which are selected independently from a group consisting of phenyl and naphthyl, and which are linked together via a single bond.

Aa1 may include, without being restricted thereto, a biphenyl radical, such as e.g. the 1,1'-biphen-3-yl or the 1,1'-biphen-4-yl radical.

As non-limiting examples of R11-substituted derivatives of Aa1 may be mentioned the following radicals:

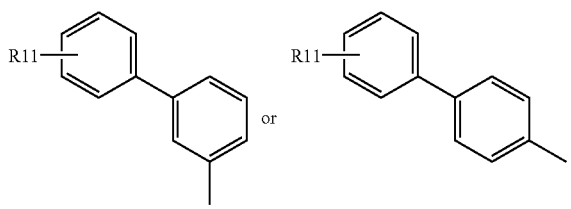

or in which the substituent R11 can be attached in the ortho, or, particularly, meta or para position with respect to the binding position in which the benzene ring is bonded to the phenyl radical, such as e.g. 4'-(R11)-1,1'-biphen-3-yl or 3'-(R11)-1,1'-biphen-3-yl, or 2'-(R11)-1,1'-biphen-4-yl, 3'-(R11)-1,1'-biphen-4-yl or 4'-(R11)-1,1'-biphen-4-yl, like, for example, the 4'-fluoro-biphen-4-yl, 3'-fluoro-biphen-4-yl, 2'-fluoro-biphen-4-yl, 4'-methoxy-biphen-4-yl, 3'-methoxy-biphen-4-yl, 2'-methoxy-biphen-4-yl, or 3'-acetylamino-biphen-4-yl radical, or the 3'-nitro-biphen-4-yl, 4'-methoxy-biphen-3-yl, 3'-methoxy-biphen-3-yl or 3'-acetylamino-biphen-3-yl radical.

In one embodiment, as exemplary Ar1 radicals may be mentioned any one selected from the group consisting of
phenyl, naphthyl such as e.g. naphthalen-1-yl or naphthalen-2-yl, fluorenyl such as e.g. fluoren-1-yl, biphenyl such as e.g. 1,1'-biphen-3-yl or 1,1'-biphen-4-yl;
4'-fluoro-biphen-4-yl, 3'-fluoro-biphen-4-yl, 2'-fluoro-biphen-4-yl, 4'-methoxy-biphen-4-yl, 3'-methoxy-biphen-4-yl, 2'-methoxy-biphen-4-yl, 3'-acetylamino-biphen-4-yl, 3'-nitro-biphen-4-yl, 4'-methoxy-biphen-3-yl, 3'-methoxy-biphen-3-yl, 3'-acetylamino-biphen-3-yl;
benzyloxy-naphthyl (e.g. 6-benzyloxy-naphthyl), hydroxy-naphthyl (e.g. 6-hydroxy-naphthyl), methoxy-naphthyl (e.g. 6-methoxy-naphthyl), ethoxy-naphthyl (e.g. 6-ethoxy-naphthyl), 2-(methoxyethoxy)-naphthyl (e.g. 6-[2-(methoxyethoxy)]-naphthyl), 2-(hydroxyethoxy)-naphthyl (e.g. 6-[2-(hydroxyethoxy)]-naphthyl), such as, for example, 6-benzyloxy-naphthalen-2-yl, 6-hydroxy-naphthalen-2-yl, 6-methoxy-naphthalen-2-yl, 6-ethoxy-naphthalen-2-yl, 6-[2-(methoxyethoxy)]-naphthalen-2-yl or 6-[2-(hydroxyethoxy)]-naphthalen-2-yl; and
benzyloxy-phenyl such as, for example, 3-benzyloxy-phenyl or 4-benzyloxy-phenyl.

In another embodiment, as exemplary Ar1 radicals may be mentioned any one selected from the group consisting of
3-benzyloxy-phenyl, 4-benzyloxy-phenyl, naphthyl, phenyl, fluoren-1-yl, biphen-4-yl, 4'-fluoro-biphen-4-yl, 3'-fluoro-biphen-4-yl, 2'-fluoro-biphen-4-yl, 4'-methoxy-biphen-4-yl, 3'-methoxy-biphen-4-yl, 2'-methoxy-biphen-4-yl, 3'-acetylamino-biphen-4-yl, 6-benzyloxy-naphthalen-2-yl, 6-hydroxy-naphthalen-2-yl, 6-methoxy-naphthalen-2-yl, 6-ethoxy-naphthalen-2-yl, 2-(methoxyethoxy)-naphthalen-2-yl, 6-[2-(methoxyethoxy)]-naphthalen-2-yl and 6-[2-(hydroxyethoxy)]-naphthalen-2-yl.

As exemplary suitable Ar1 radicals may be explicitely mentioned biphen-4-yl, 4'-fluoro-biphen-4-yl, 3'-fluoro-biphen-4-yl, 2'-fluoro-biphen-4-yl, 4'-methoxy-biphen-4-yl, 3'-methoxy-biphen-4-yl, 2'-methoxy-biphen-4-yl, 3'-acetylamino-biphen-4-yl, 3'-nitro-biphen-4-yl, 4'-methoxy-biphen-3-yl, 3'-methoxy-biphen-3-yl or 3'-acetylamino-biphen-3-yl; as well as benzyloxy-naphthyl (e.g. 6-benzyloxy-naphthyl), hydroxy-naphthyl (e.g. 6-hydroxy-naphthyl), methoxy-naphthyl (e.g. 6-methoxy-naphthyl), ethoxy-naphthyl (e.g. 6-ethoxy-naphthyl), 2-(methoxyethoxy)-naphthyl (e.g. 6-[2-(methoxyethoxy)]-naphthyl), 2-(hydroxyethoxy)-naphthyl (e.g. 6-[2-(hydroxyethoxy)]-naphthyl), such as, for example, 6-benzyloxy-naphthalen-2-yl, 6-hydroxy-naphthalen-2-yl, 6-methoxy-naphthalen-2-yl, 6-ethoxy-naphthalen-2-yl, 2-(methoxyethoxy)-naphthalen-2-yl, 6-[2-(methoxyethoxy)]-naphthalen-2-yl or 6-[2-(hydroxyethoxy)]-naphthalen-2-yl.

Har1 is optionally substituted by R12, and is an unsaturated monocyclic 5- or 6-membered heteroaryl radical comprising one to four heteroatoms, or, in an embodiment, one, two or three heteroatoms, each of which is selected from the group consisting of nitrogen, oxygen and sulphur. In particular, Har1 is optionally substituted by R12 on a ring nitrogen atom.

Non-limiting examples of Har1 include the 5-membered ring radicals such as, without being restricted to, furanyl, thiophenyl, pyrrolyl, oxazolyl, isoxazolyl, thiazolyl, isothiazolyl, imidazolyl, pyrazolyl, triazolyl, (precisely: 1,2,4-triazolyl or 1,2,3-triazolyl), thiadiazolyl (precisely: 1,3,4-thiadiazolyl, 1,2,5-thiadiazolyl, 1,2,3-thiadiazolyl or 1,2,4-thiadiazolyl) or oxadiazolyl (precisely: 1,3,4-oxadiazolyl, 1,2,5-oxadiazolyl, 1,2,3-oxadiazolyl or 1,2,4-oxadiazolyl), and the 6-membered ring radicals such as, without being restricted to, pyridinyl, pyrimidinyl, pyrazinyl or pyridazinyl.

Har2 is optionally substituted by R13, and is an unsaturated fused bicyclic 9- or 10-membered heteroaryl radical comprising one to four heteroatoms, or, in an embodiment, one, two or three heteroatoms, each of which is selected from the group consisting of nitrogen, oxygen and sulphur. In particular, Har2 is optionally substituted by R13 on a ring nitrogen atom.

Non-limiting examples of Har2 include, without being restricted thereto, the benzo-fused analogues of the aforementioned monocyclic 5-membered Har1 radicals, like e.g. benzothiophenyl, benzofuranyl, indolyl, benzoxazolyl, benzothiazolyl, indazolyl, benzimidazolyl, benzisoxazolyl, benzisothiazolyl, benzoxadiazolyl (e.g. benzofurazanyl), benzotriazolyl, benzothiadiazolyl, isoindolyl, isobenzofuranyl or isobenzothiophenyl, or indolizinyl; and the benzo-fused analogues of the aforementioned monocyclic 6-membered Har1 radicals, like e.g. quinolinyl, isoquinolinyl, quinazolinyl, quinoxalinyl, phthalazinyl or cinnolinyl, or naphthyridinyl.

Har3 is optionally substituted by R14, and is an unsaturated fused tricyclic 13- or 14-membered heteroaryl radical comprising one to four heteroatoms, or, in an embodiment, one, two or three heteroatoms, or, in another embodiment, one or two heteroatoms, each of which is selected from the group consisting of nitrogen, oxygen and sulphur.

In particular, Har3 is optionally substituted by R14 on a ring nitrogen atom.

Non-limiting examples of Har3 include, without being restricted to, carbazolyl, phenanthridinyl, acridinyl, carbolinyl, phenazinyl, dibenzofuranyl, dibenzothiophenyl, phenothiazinyl, phenoxazinyl, phenoxathiinyl or thianthrenyl.

As exemplary Har3 radical may be more detailed mentioned, for example, thianthrenyl e.g. thianthren-1-yl, dibenzothiophenyl e.g. dibenzothiophen-4-yl, or dibenzofuranyl e.g. dibenzofuran-4-yl.

As exemplary suitable Har3 radical may be explicitly mentioned, for example, dibenzofuranyl, such as e.g. the dibenzofuran-4-yl radical:

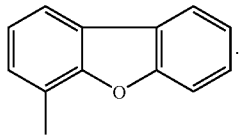

Cyc1 is a group of formula A

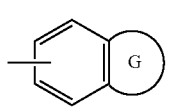

(A)

in which

G is a 5- or 6-membered saturated or partially unsaturated heterocyclic ring comprising one or two heteroatoms independently selected from the group consisting of oxygen and sulfur, whereby said Cyc1 ring system is attached to the parent molecular group via any substitutable benzring carbon atom.

As examples of Cyc1 may be mentioned, without being restricted thereto, 1,3-benzodioxolyl, 2,3-dihydro-1,4-benzodioxinyl, 2,3-dihydrobenzothiophenyl, chromanyl, chromenyl or 2,3-dihydrobenzofuranyl.

As exemplary Cyc1 radicals may be more detailed mentioned, for example, 1,3-benzodioxol-5-yl.

Hh1 is optionally substituted by R15, and is a bisheteroaryl radical made up of two heteroaryl groups, which are selected independently from a group consisting of monocyclic 5- or 6-membered heteroaryl radicals comprising one or two heteroatoms, each of which is selected from the group consisting of nitrogen, oxygen and sulfur, and which are linked together via a single bond.

In particular, Hh1 is optionally substituted by R15 on a ring nitrogen atom.

Hh1 may include, without being restricted thereto, the bithiophenyl radical, such as, for example, (thiophen-3-yl)-thiophenyl or (thiophen-2-yl)-thiophenyl, e.g. the 5-(thiophen-2-yl)-thiophen-2-yl radical.

Ah1 optionally substituted by R16, and is an arylheteroaryl radical made up of an aryl group selected from a group consisting of phenyl and naphthyl, and a heteroaryl group selected from a group consisting of monocyclic 5- or 6-membered heteroaryl radicals comprising one or two heteroatoms, each of which is selected from the group consisting of nitrogen, oxygen and sulfur, whereby said aryl and heteroaryl groups are linked together via a single bond, and whereby Ah1 is bonded via said heteroaryl moiety to the parent molecular group.

In particular, Ah1 is optionally substituted by R16 on a ring nitrogen atom.

Ah1 may include, without being restricted thereto, the phenyl-thiophenyl or the phenyl-pyridyl radical.

As non-limiting example of Ah1, the phenyl-pyridyl radical, such as e.g. the 6-phenyl-pyridin-3-yl radical, may be mentioned.

Ha1 optionally substituted by R17, and is a heteroarylaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, and whereby Ha1 is bonded via said aryl moiety to the to the parent molecular group.

In particular, Ha1 is optionally substituted by R17 on a ring nitrogen atom.

A particular embodiment of said Ha1 radicals refers to heteroaryl-phenyl radicals, particularly 3-(heteroaryl)-phenyl or 4-(heteroaryl)-phenyl radicals.

Ha1 may include, without being restricted thereto, the furanyl-phenyl, the thiophenyl-phenyl, the pyrazolyl-phenyl or the pyridyl-phenyl radical.

As non-limiting example of R17-substituted derivatives of Ha1, [1N-(1-4C-alkyl)-pyrazol-4-yl]-phenyl, e.g. (1-methyl-pyrazol-4-yl)-phenyl, such as the 3-(1N-methyl-pyrazol-4-yl)-phenyl or the 4-(1N-methyl-pyrazol-4-yl)-phenyl radical may be mentioned.

In the context of the foregoing, it is to be stated, that each of the radicals Har1, Har2, Har3, Hh1 and Ah1 is bonded via a ring carbon atom to the pyrazolopyrimidine scaffold.

Har4 is optionally substituted by R33, and is a monocyclic or fused bicyclic 5- to 10-membered unsaturated heteroaryl radical comprising one to four heteroatoms, or, in an embodiment, one, two or three heteroatoms, each of which is selected from the group consisting of nitrogen, oxygen and sulphur, whereby said Har4 radical is attached to the moiety V via a ring carbon atom. In particular, Har4 is optionally substituted by R33 on a ring carbon atom.

Examplary Har4 radicals may include, but are not limited thereto, the monocyclic derivatives, such as e.g. furanyl, thiophenyl, pyrrolyl, oxazolyl, isoxazolyl, thiazolyl, isothiazolyl, imidazolyl, pyrazolyl, triazolyl, thiadiazolyl, oxadiazolyl, pyridinyl, pyrimidinyl, pyrazinyl, pyridazinyl, the bicyclic, benzo-fused analogues thereof, such as e.g. quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl or benzimidazolyl, as well as naphthyridinyl, indolizinyl or purinyl.

As non-limiting examples of R33-substituted derivatives of Har4, R33-substituted pyridinyl, e.g. aminomethyl-pyridyl, or R33-substituted furanyl, e.g. aminomethyl-furanyl, radicals may be mentioned.

As exemplary Har4 radicals may be more detailed mentioned, for example, furanyl or pyridyl.

As exemplary Har4 radicals may be further more detailed mentioned, for example, furan-2-yl, pyridin-4-yl, aminomethyl-pyridyl, such as e.g. 6-(aminomethyl)-pyridin-2-yl, 6-(aminomethyl)-pyridin-3-yl, 5-(aminomethyl)-pyridin-3-yl, 2-(aminomethyl)-pyridin-4-yl, 4-(aminomethyl)-pyridin-2-yl or 5-(aminomethyl)-pyridin-2-yl, or aminomethyl-furanyl, such as e.g. 5-(aminomethyl)-furan-2-yl.

As exemplary suitable Har4 radicals may be explicitly mentioned, for example, (aminomethyl)-pyridyl or (aminomethyl)-furanyl, such as e.g. 6-(aminomethyl)-pyridin-2-yl, 6-(aminomethyl)-pyridin-3-yl, 5-(aminomethyl)-pyridin-3-yl, 2-(aminomethyl)-pyridin-4-yl, 4-(aminomethyl)-pyridin-2-yl or 5-(aminomethyl)-pyridin-2-yl, or 5-(aminomethyl)-furan-2-yl.

Het1 is a monocylic 3- to 7-membered saturated heterocyclic ring comprising the nitrogen atom, to which R301 and R302 are attached, and optionally one further heteroatom selected from a group consisting of oxygen, nitrogen, N(R303) and sulphur.

Het1 may include, without being restricted thereto, aziridin-1-yl, azetidin-1-yl, pyrrolidin-1-yl, piperidin-1-yl, homopiperidin-1-yl, pyrazolidin-1-yl, imidazolidin-1-yl, piperazin-1-yl, homopiperazin-1-yl, morpholin-4-yl or thiomorpholin-4-yl.

As further examples for Het1 may be mentioned, without being restricted thereto, morpholin-4-yl, 2-N—(R303)-pyrazolidin-1-yl, 3-N—(R303)-imidazolidin-1-yl, 4-N—(R303)-piperazin-1-yl or 4-N—(R303)-homopiperazin-1-yl.

As exemplary Het1 radicals may be more detailed mentioned, for example, morpholin-4-yl or 4-N-methyl-piperazin-1-yl.

Het2 is a monocylic 3- to 7-membered saturated heterocyclic ring, which comprises one nitrogen atom and optionally one further heteroatom selected from a group consisting of oxygen, nitrogen, N(R304) and sulfur, whereby said Het2 radical is attached to the parent molecular group via a ring carbon atom.

Het2 may include, without being restricted thereto, aziridinyl, azetidinyl, pyrrolidinyl, piperidinyl, homopiperidinyl, pyrazolidinyl, imidazolidinyl, piperazinyl, homopiperazinyl, morpholinyl or thiomorpholinyl.

In more detail, Het2 may include, without being restricted thereto, 1NH-piperidinyl including piperidin-2-yl, piperidin-3-yl and piperidin-4-yl.

As further examples for Het2 may be mentioned, without being restricted thereto, 1N—(R304)-piperidinyl, such as e.g. 1N—(R304)-piperidin-3-yl or 1N—(R304)-piperidin-4-yl.

As exemplary suitable Het2 radicals may be explicitly mentioned, for example, piperidin-3-yl.

Cyc2 is a group of formula A

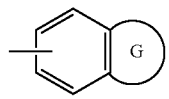

(A)

in which

G is a 5- or 6-membered saturated heterocyclic ring comprising one nitrogen atom and optionally one further heteroatom selected from the group consisting of oxygen, nitrogen and sulfur, whereby said Cyc2 ring system is attached to the parent molecular group via any substitutable benzoring carbon atom.

As examples of Cyc2 may be mentioned, without being restricted thereto, indolinyl, isoindolinyl, 1,2,3,4-tetrahydroquinolinyl, 1,2,3,4-tetrahydroisoquinolinyl, or 3,4-dihydrobenzo[1,4]-oxazinyl.

As exemplary Cyc2 radicals may be more detailed mentioned, for example, isoindolinyl or 1,2,3,4-tetrahydroisoquinolinyl.

As exemplary suitable Cyc2 radicals may be explicitly mentioned, for example, 1,2,3,4-tetrahydroisoquinolinyl, such as e.g. 1,2,3,4-tetrahydroisoquinolin-6-yl or 1,2,3,4-tetrahydroisoquinolin-7-yl.

As exemplary suitable Cyc2 radicals may be more explicitely mentioned, for example, 1,2,3,4-tetrahydroisoquinolin-6-yl.

The term "thiophenyl" alone or as part of another group is used herein synonymously with the term "thienyl".

The expression "4-(R31)-fluoro-phenyl" means that the phenyl radical is substituted by both R31 and fluorine, whereby the substituent R31 is bonded in the 4-position to the phenyl radical, and fluorine is bonded in any other position to the phenyl ring; and the expression "2-fluoro-4-(R31)-phenyl" means, that the phenyl radical is substituted by both R31 and fluorine, whereby the substituent R31 is bonded in the 4-position to the phenyl radical, and fluorine is bonded in the 2-position to the phenyl ring; In this connection, further similar expressions mentioned herein indicating in short form the positions in which substituents are bonded to a ring radical are to be understood similarly, mutatis mutandis, as specified exemplarily and representatively for the foregoing two expressions.

In general, unless otherwise mentioned, the heterocyclic groups mentioned herein refer to all of the possible isomeric forms thereof.

The heterocyclic groups mentioned herein refer, unless otherwise noted, in particular to all of the possible positional isomers thereof.

Thus, for example, the term pyridyl or pyridinyl, alone or as part of another group, includes pyridin-2-yl, pyridin-3-yl and pyridin-4-yl.

Constituents which are optionally substituted as stated herein, may be substituted, unless otherwise noted, at any possible position.

The carbocyclic groups, alone or as part of other groups, mentioned herein may be substituted by their given substituents or parent molecular groups, unless otherwise noted, at any substitutable ring carbon atom.

The heterocyclic groups, alone or as part of other groups, mentioned herein may be substituted by their given substituents or parent molecular groups, unless otherwise noted, at any possible position, such as e.g. at any substitutable ring carbon or ring nitrogen atom.

Rings containing imino-type ring nitrogen atoms (—N═) may be preferably not substituted on these imino-type ring nitrogen atoms by the mentioned substituents or parent molecular groups.

Any heteroatom of a heterocyclic ring with unsatisfied valences mentioned herein is assumed to have the hydrogen atom(s) to satisfy the valences.

When any variable occurs more than one time in any constituent, each definition is independent.

Suitable salts for compounds of formula I according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds of formula I according to this invention on an industrial scale, are converted into pharmacologically tolerable salts by processes known to the person skilled in the art.

According to expert's knowledge the compounds of formula I according to this invention as well as their salts may contain, e.g. when isolated in crystalline form, varying amounts of solvents. Included within the scope of the invention are therefore all solvates and in particular all hydrates of the compounds of formula I according to this invention as well as all solvates and in particular all hydrates of the salts of the compounds of formula I according to this invention.

The substituents R2 and —N(H)C(O)R3 of compounds of formula I can be attached in the ortho, meta or para position with respect to the binding position in which the phenyl ring is bonded to the pyrazolopyrimidinyl-amino moiety, whereby preference is given, in a first independent embodiment, to the attachment of —N(H)C(O)R3 in the meta position, and particular preference is given, in a second independent embodiment, to the attachment of —N(H)C(O)R3 in the para position.

The substituents R31 and R32 of compounds of formula I can be attached in the ortho, meta or para position with respect to the binding position in which the phenyl ring is bonded to the moiety U, whereby preference is given to the attachment of R31 in the meta or, particularly, in the para position.

The substituents R4 of compounds of formula I can be attached in the 2- or 3-position of the pyrazolo[1,5-c]pyrimidine scaffold, whereby preference is given to the attachment of R4 in the 3-position of the pyrazolo[1,5-c]pyrimidine scaffold.

Compounds according to aspect A of this invention more worthy to be mentioned are those compounds of formula I, in which
R1 is Ar1, or
  Har3, or
  Ah1 or Ha1, in which
Ar1 is optionally substituted by R11, and is phenyl, naphthyl or Aa1, in which
Aa1 is biphenyl,
R11 is 1-4C-alkoxy, 1-4C-alkoxy-2-4C-alkoxy, halogen, hydroxyl, nitro, phenoxy, phenyl-1-4C-alkoxy, hydroxy-2-4C-alkoxy, carboxy-1-4C-alkoxy or 1-4C-alkylcarbonylamino,
Har3 is dibenzofuranyl,
Ah1 is the phenyl-pyridyl radical,
Ha1 is optionally substituted by R17 on the pyrazolyl moiety, and is the pyrazolyl-phenyl radical, in which
R17 is 1-4C-alkyl;
R2 is hydrogen;
R3 is T-R30, —U—Ar2, —V-Har4, or Cyc2, in which
T is 1-4C-alkylene,
R30 is —N(R301)R302, in which
R301 is hydrogen, 1-4C-alkyl or hydroxy-2-4C-alkyl,
R302 is hydrogen or 1-4C-alkyl, either
U is a bond,
Ar2 is R31-substituted phenyl, or R31- and R32-substituted phenyl, in which
R31 is amidino, guanidino, Het2 or —W—R311, in which
Het2 is piperidinyl or pyrrolidinyl,
  whereby said Het2 radical is attached to the parent molecular group via a ring carbon atom,
W is a bond or 1-4C-alkylene,
R311 has one of the foregoing meanings of R30, and
R32 is halogen, or
U is 1-4C-alkylene substituted with amino-1-4C-alkyl,
Ar2 is R31- and R32-substituted phenyl, in which
R31 is halogen, and
R32 is halogen,
V is a bond,
Har4 is R33-substituted pyridyl, R33-substituted thiophenyl or
R33-substituted furanyl, in which
R33 is -Z-R331, in which
Z is 1-4C-alkylene,
R331 has one of the foregoing meanings of R30,
Cyc2 is

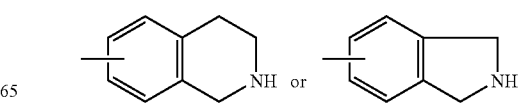

whereby the substituent —N(H)C(O)R3 is attached in the meta or para position with respect to the binding position in which the phenyl ring is bonded to the pyrazolopyrimidinyl-amino moiety;
R4 is hydrogen or bromine;

and the salts of these compounds.

Compounds according to aspect A of this invention in particular worthy to be mentioned are those compounds, which are from formula Ib or Ic as shown below, and in which
R1 is Ar1, or
  Har3, or
  Ah1 or Ha1, in which either
Ar1 is naphthalen-2-yl or 6-(R11)-naphthalen-2-yl, in which
R11 is 1-2C-alkoxy, 2-methoxyethoxy, hydroxyl, benzyloxy or 2-hydroxyethoxy, or
Ar1 is biphen-3-yl, biphen-4-yl, 2'-(R11)-biphen-3-yl, 3'-(R11)-biphen-3-yl, 4'-(R11)-biphen-3-yl, 2'-(R11)-biphen-4-yl, 3'-(R11)-biphen-4-yl or 4'-(R11)-biphen-4-yl, in which
R11 is 1-2C-alkoxy, nitro, 1-2C-alkylcarbonylamino or halogen, or
Ar1 is 3-(R11)-phenyl or 4-(R11)-phenyl, in which
R11 is halogen,
Har3 is dibenzofuran-4-yl,
Ah1 is phenyl-pyridyl,
Ha1 is 3-(pyrazol-1-yl)-phenyl, 3-(1N-H-pyrazolyl)-phenyl, 3-[1N-(1-2C-alkyl)-pyrazolyl]-phenyl, 4-(pyrazol-1-yl)-phenyl, 4-(1N-H-pyrazolyl)-phenyl or 4-[1N-(1-2C-alkyl)-pyrazolyl]-phenyl;
R2 is hydrogen;
R3 is -T-R30, —U—Ar2, —V-Har4, or Cyc2, in which
T is 1-4C-alkylene,
R30 is amino, either
U is a bond, and
Ar2 is 2-(R31)-phenyl, 3-(R31)-phenyl or 4-(R31)-phenyl, in which
R31 is amino, or
U is a bond, and
Ar2 is 3-(R31)-phenyl or 4-(R31)-phenyl, in which
R31 is guanidino, amidino or 1N-H-piperidinyl, or
U is a bond, and
Ar2 is 3-(R31)-phenyl, 4-(R31)-phenyl, R32-substituted 3-(R31)-phenyl, or R32-substituted 4-(R31)-phenyl, in which
R31 is —W—R311, in which
W is 1-4C-alkylene,
R311 is —N(R301)R302, in which
R301 is hydrogen, 1-2C-alkyl or 2-hydroxyethyl,
R302 is hydrogen, and
R32 is fluorine, or
U is 1-4C-alkylene substituted with amino-1-4C-alkyl, and
Ar2 is R31- and R32-substituted phenyl, in which
R31 is chlorine, and
R32 is chlorine,
V is a bond, Har4 is R33-substituted pyridyl, or R33-substituted furanyl, in which
R33 is -Z-R331, in which
Z is 1-4C-alkylene,
R331 is amino,
Cyc2 is any one of the following radicals:

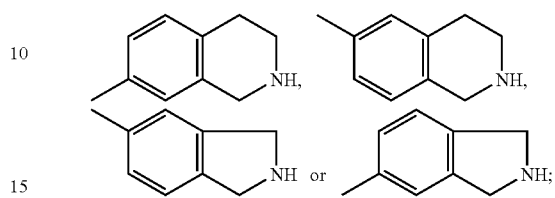

R4 is hydrogen or bromine;

and the salts of these compounds.

Compounds according to aspect A of this invention in more particular worthy to be mentioned are those compounds, which are from formula Ib or Ic as shown below, and in which
R1 is Ar1, or
  Har3, or
  Ah1 or Ha1, in which either
Ar1 is naphthalen-2-yl, or 6-(R11)-naphthalen-2-yl, in which
R11 is 1-2C-alkoxy, 2-methoxyethoxy, hydroxyl, benzyloxy or 2-hydroxyethoxy, or
Ar1 is biphen-3-yl, biphen-4-yl, 2'-(R11)-biphen-4-yl, 3'-(R11)-biphen-4-yl, 4'-(R11)-biphen-4-yl, 3'-(R11)-biphen-3-yl or 4'-(R11)-biphen-3-yl, in which
R11 is 1-2C-alkoxy, nitro, fluorine or 1-2C-alkylcarbonylamino, or
Ar1 is 3-(R11)-phenyl or 4-(R11)-phenyl, in which
R11 is bromine or iodine,
Har3 is dibenzofuran-4-yl,
Ah1 is 6-phenyl-pyridin-3-yl,
Ha1 is 4-[1N-(1-2C-alkyl)-pyrazol-4-yl]-phenyl;
R2 is hydrogen;
R3 is -T-R30, —U—Ar2, —V-Har4, or Cyc2, in which
T is straight chain 1-4C-alkylene,
R30 is amino, either
U is a bond, and
Ar2 is 4-(R31)-phenyl or 3-(R31)-phenyl, in which
R31 is guanidino, or
U is a bond, and
Ar2 is 4-(R31)-phenyl, 3-(R31)-phenyl or 2-fluoro-4-(R31)-phenyl, in which
R31 is —W—R311, in which
W is methylene or ethylene,
R311 is —N(R301)R302, in which
R301 is hydrogen, methyl or 2-hydroxyethyl,
R302 is hydrogen, or
U is methylene substituted with amino-1-2C-alkyl, and
Ar2 is 3,4-dichloro-phenyl,
V is a bond, Har4 is R33-substituted pyridyl, or R33-substituted furanyl, in which
R33 is -Z-R331, in which
Z is methylene,
R331 is amino,
Cyc2 is 1,2,3,4-tetrahydroisoquinolin-6-yl or 1,2,3,4-tetrahydroisoquinolin-7-yl;
R4 is hydrogen or bromine;

and the salts of these compounds.

In one embodiment, compounds according to aspect A of this invention to be emphasized are those compounds, which are from formula Ic or, in particular, from formula Ib as shown below, and
in which
R1 is Ar1, or
    Har3, or
    Ah1 or Ha1, in which either
Ar1 is 6-(R11)-naphthalen-2-yl, in which
R11 is 1-2C-alkoxy, 2-methoxyethoxy, hydroxyl, benzyloxy or 2-hydroxyethoxy, or
Ar1 is biphen-3-yl, biphen-4-yl, 2'-(R11)-biphen-4-yl, 3'-(R11)-biphen-4-yl, 4'-(R11)-biphen-4-yl, 3'-(R11)-biphen-3-yl or 4'-(R11)-biphen-3-yl, in which
R11 is methoxy, fluorine, acetylamino or nitro,
Har3 is dibenzofuran-4-yl,
Ah1 is 6-phenyl-pyridin-3-yl,
Ha1 is 4-(1N-methyl-pyrazol-4-yl)-phenyl;
R2 is hydrogen;
R3 is —U—Ar2, —V-Har4, or Cyc2, in which either
U is a bond, and
Ar2 is 4-(R31)-phenyl or 3-(R31)-phenyl, in which
R31 is guanidino, or
U is a bond, and
Ar2 is 4-(R31)-phenyl, 3-(R31)-phenyl or 2-fluoro-4-(R31)-phenyl, in which
R31 is —W—R311, in which
W is methylene or ethylene,
R311 is —N(R301)R302, in which
R301 is hydrogen or methyl,
R302 is hydrogen,
V is a bond,
Har4 is 6-(aminomethyl)-pyridin-3-yl, 2-(aminomethyl)-pyridin-4-yl, 6-(aminomethyl)-pyridin-2-yl, 5-(aminomethyl)-pyridin-3-yl or 5-(aminomethyl)-pyridin-2-yl, or 5-(aminomethyl)-furan-2-yl,
Cyc2 is 1,2,3,4-tetrahydroisoquinolin-6-yl or 1,2,3,4-tetrahydroisoquinolin-7-yl;
R4 is hydrogen;

and the salts of these compounds.

In another embodiment, compounds according to aspect A of this invention to be emphasized are those compounds, which are from formula Ic or, in particular, from formula Ib as shown below, and in which
R1 is Ar1, or
    Har3, or
    Ah1 or Ha1, in which either
Ar1 is 6-(R11)-naphthalen-2-yl, in which
R11 is 1-2C-alkoxy, 2-methoxyethoxy, hydroxyl, benzyloxy or 2-hydroxyethoxy, or
Ar1 is biphen-3-yl, biphen-4-yl, 2'-(R11)-biphen-4-yl, 3'-(R11)-biphen-4-yl, 4'-(R11)-biphen-4-yl, 3'-(R11)-biphen-3-yl or 4'-(R11)-biphen-3-yl, in which
R11 is methoxy, fluorine, acetylamino or nitro,
Har3 is dibenzofuran-4-yl,
Ah1 is 6-phenyl-pyridin-3-yl,
Ha1 is 4-(1N-methyl-pyrazol-4-yl)-phenyl;
R2 is hydrogen;
R3 is —U—Ar2, —V-Har4, or Cyc2, in which either
U is a bond, and
Ar2 is 4-(R31)-phenyl or 3-(R31)-phenyl, in which
R31 is guanidino, or
U is a bond, and
Ar2 is 4-(R31)-phenyl, 3-(R31)-phenyl or 2-fluoro-4-(R31)-phenyl, in which
R31 is —W—R311, in which
W is methylene or ethylene,
R311 is —N(R301)R302, in which
R301 is hydrogen or methyl,
R302 is hydrogen,
V is a bond,
Har4 is 6-(aminomethyl)-pyridin-3-yl, 2-(aminomethyl)-pyridin-4-yl, 6-(aminomethyl)-pyridin-2-yl, 5-(aminomethyl)-pyridin-3-yl or 5-(aminomethyl)-pyridin-2-yl, or 5-(aminomethyl)-furan-2-yl,
Cyc2 is 1,2,3,4-tetrahydroisoquinolin-6-yl or 1,2,3,4-tetrahydroisoquinolin-7-yl;
R4 is bromine;

and the salts of these compounds.

Compounds according to aspect B of this invention more worthy to be mentioned are those compounds, which are from formula Ib or Ic as shown below, and
in which
R1 is Ar1, or
    Har3, or
    Cyc1, or
    Ah1 or Ha1, in which
Ar1 is optionally substituted by R11, and is phenyl, naphthyl or Aa1, in which
Aa1 is biphenyl,
R11 is 1-4C-alkoxy, 1-4C-alkoxy-2-4C-alkoxy, halogen, hydroxyl, phenoxy, phenyl-1-4C-alkoxy, hydroxy-2-4C-alkoxy, carboxy-1-4C-alkoxy or 1-4C-alkylcarbonylamino,
Har3 is dibenzofuranyl,
Cyc1 is 1,3-benzodioxolyl or 2,3-dihydro-1,4-benzodioxinyl,
Ah1 is the phenyl-pyridyl radical,
Ha1 is the [1N—(R17)-pyrazolyl]-phenyl radical, in which
R17 is 1-4C-alkyl;
R2 is hydrogen;
R3 is -T-R30, —U—Ar2, —V-Har4, or Cyc2, in which
T is 1-4C-alkylene,
R30 is —N(R301)R302, in which
R301 is hydrogen, 1-4C-alkyl or hydroxy-2-4C-alkyl,
R302 is hydrogen or 1-4C-alkyl, or R301 and R302 together an with inclusion of the nitrogen atom to which they are bonded form a radical Het1, in which
Het1 is 4N—(R303)-piperazin-1-yl,
R303 is 1-4C-alkyl, either
U is a bond,
Ar2 is R31-substituted phenyl, or R31- and R32-substituted phenyl, in which
R31 is 1-4C-alkyl, guanidino, Het2 or —W—R311, in which
Het2 is piperidinyl or pyrrolidinyl,
whereby said Het2 radical is attached to the parent molecular group via a ring carbon atom,
W is a bond or 1-4C-alkylene,
R311 has one of the foregoing meanings of R30, and
R32 is halogen, or
U is 1-4C-alkylene substituted with amino-1-4C-alkyl,
Ar2 is R31- and R32-substituted phenyl, in which
R31 is halogen, and
R32 is halogen,
V is a bond,
Har4 is R33-substituted pyridyl, R33-substituted thiophenyl or R33-substituted furanyl, in which
R33 is -Z-R331, in which
Z is 1-4C-alkylene,
R331 has one of the foregoing meanings of R30,
Cyc2 is

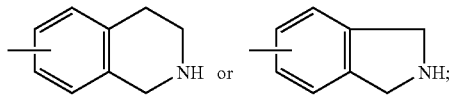

R4 is hydrogen;
and the salts of these compounds.

Compounds according to aspect B of this invention in particular worthy to be mentioned are those compounds, which are from formula Ib or Ic as shown below, and in which
R1 is Ar1, or
Har3, or
Ah1 or Ha1, in which
either
Ar1 is optionally substituted by R11, and is naphthyl, in which
R11 is 1-4C-alkoxy, 1-4C-alkoxy-2-4C-alkoxy, hydroxyl, phenyl-1-4C-alkoxy or hydroxy-2-4C-alkoxy, or
Ar1 is optionally substituted by R11, and is Aa1, in which
Aa1 is 1,1'-biphen-4-yl, and
R11 is 1-4C-alkoxy, fluorine or 1-4C-alkylcarbonylamino,
Har3 is dibenzofuran-4-yl,
Ah1 is 6-phenyl-pyridin-3-yl,
Ha1 is 4-[1N—(R17)-pyrazol-4-yl]-phenyl, in which
R17 is 1-4C-alkyl;
R2 is hydrogen;
R3 is -T-R30, —U—Ar2, —V-Har4, or Cyc2, in which
T is 1-4C-alkylene,
R30 is amino, either
U is a bond, and
Ar2 is R31-substituted phenyl, in which
R31 is guanidino, 1N—H-piperidinyl or amino, or
U is a bond, and
Ar2 is R31-substituted phenyl, or R31- and R32-substituted phenyl, in which
R31 is —W—R311, in which
W is 1-4C-alkylene,
R311 is —N(R301)R302, in which
R301 is hydrogen, 1-4C-alkyl or hydroxy-2-4C-alkyl,
R302 is hydrogen, and
R32 is fluorine, or
U is 1-4C-alkylene substituted with amino-1-4C-alkyl, and
Ar2 is R31- and R32-substituted phenyl, in which
R31 is chlorine, and
R32 is chlorine,
V is a bond,
Har4 is R33-substituted pyridyl, or R33-substituted furanyl, in which
R33 is -Z-R331, in which
Z is 1-4C-alkylene,
R331 is amino,
Cyc2 is any one of the following radicals:

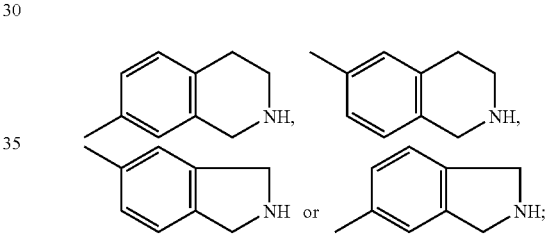

R4 is hydrogen;
and the salts of these compounds.

Compounds according to aspect B of this invention in more particular worthy to be mentioned are those compounds, which are from formula Ib or Ic as shown below, and in which
R1 is Ar1, or
Har3, or
Ah1 or Ha1, in which
either
Ar1 is naphthalen-2-yl, or 6-(R11)-naphthalen-2-yl, in which
R11 is 1-2C-alkoxy, 2-methoxyethoxy, hydroxyl, benzyloxy or 2-hydroxyethoxy, or
Ar1 is biphen-4-yl, or 2'-(R11)-biphen-4-yl, 3'-(R11)-biphen-4-yl or 4'-(R11)-biphen-4-yl, in which
R11 is 1-2C-alkoxy, fluorine or 1-2C-alkylcarbonylamino,
Har3 is dibenzofuran-4-yl,
Ah1 is 6-phenyl-pyridin-3-yl,
Ha1 is 4-[1N—(R17)-pyrazol-4-yl]-phenyl, in which
R17 is 1-2C-alkyl;
R2 is hydrogen;
R3 is -T-R30, —U—Ar2, —V-Har4, or Cyc2, in which
T is straight chain 1-4C-alkylene,
R30 is amino, either
U is a bond, and
Ar2 is 4-(R31)-phenyl, or 3-(R31)-phenyl, in which
R31 is guanidino, or U is a bond, and
Ar2 is 4-(R31)-phenyl, 3-(R31)-phenyl or 2-fluoro-4-(R31)-phenyl, in which
R31 is —W—R311, in which
W is methylene or ethylene,
R311 is —N(R301)R302, in which
R301 is hydrogen, methyl or 2-hydroxyethyl,
R302 is hydrogen, or U is methylene substituted with amino-1-2C-alkyl, and
Ar2 is 3,4-dichloro-phenyl,
V is a bond,
Har4 is R33-substituted pyridyl, or R33-substituted furanyl, in which
R33 is -Z-R331, in which
Z is methylene,
R331 is amino,
Cyc2 is 1,2,3,4-tetrahydroisoquinolin-6-yl or 1,2,3,4-tetrahydroisoquinolin-7-yl;
R4 is hydrogen;

and the salts of these compounds.

Further compounds according to aspect B of this invention in more particular worthy to be mentioned are those compounds, which are from formula Ic or, in particular, from formula Ib as shown below, and in which
R1 is Ar1, or
  Har3, or
  Hal, in which either Ar1 is 6-(R11)-naphthalen-2-yl, in which
R11 is 1-2C-alkoxy, 2-methoxyethoxy, hydroxyl, benzyloxy or 2-hydroxyethoxy, or Ar1 is biphen-4-yl, 3'-acetylamino-biphen-4-yl, 2'-(R11)-biphen-4-yl, 3'-(R11)-biphen-4-yl, or 4'-(R11)-biphen-4-yl, in which
R11 is methoxy, or fluorine,
Har3 is dibenzofuran-4-yl,
Hal is 4-(1N-methyl-pyrazol-4-yl)-phenyl,
R2 is hydrogen;
R3 is —U—Ar2, —V-Har4, or Cyc2, in which either U is a bond, and
Ar2 is 4-(R31)-phenyl, in which
R31 is guanidino, or U is a bond, and
Ar2 is 4-(R31)-phenyl, 3-(R31)-phenyl, or 2-fluoro-4-(R31)-phenyl, in which
R31 is —W—R311, in which
W is methylene or ethylene,
R311 is —N(R301)R302, in which
R301 is hydrogen or methyl,
R302 is hydrogen,
V is a bond,
Har4 is 6-(aminomethyl)-pyridin-3-yl, 2-(aminomethyl)-pyridin-4-yl, 6-(aminomethyl)-pyridin-2-yl, 5-(aminomethyl)-pyridin-3-yl or 5-(aminomethyl)-pyridin-2-yl, or 5-(aminomethyl)-furan-2-yl,
Cyc2 is 1,2,3,4-tetrahydroisoquinolin-6-yl or 1,2,3,4-tetrahydroisoquinolin-7-yl;
R4 is hydrogen;

and the salts of these compounds.

A special interest in the compounds according to this invention refers to those compounds of formula I which are included—within the scope of this invention—by one or, when possible, by more of the following special embodiments:

A special embodiment (embodiment 1) of the compounds of formula I according to this invention refers to those compounds of formula I, in which
R1 is dibenzofuranyl, such as, in particular, dibenzofuran-4-yl.

Another special embodiment (embodiment 2) of the compounds of formula I according to this invention refers to those compounds of formula I, in which
R1 is naphthyl, or R11-substituted naphthyl,
  such as, for example, naphthalen-1-yl or naphthalen-2-yl, or R11-substituted naphthalen-1-yl or R11-substituted naphthalen-2-yl, such as e.g. 6-(R11)-naphthalen-1-yl or 6-(R11)-naphthalen-2-yl, in particular, 6-benzyloxy-naphthalen-2-yl, 6-hydroxy-naphthalen-2-yl, 6-methoxy-naphthalen-2-yl, 6-ethoxy-naphthalen-2-yl, 6-[2-(methoxyethoxy)]-naphthalen-2-yl or 6-[2-(hydroxyethoxy)]-naphthalen-2-yl.

Another special embodiment (embodiment 3) of the compounds of formula I according to this invention refers to those compounds of formula I, in which
R1 is biphenyl, or R11-substituted biphenyl,
  such as, for example, biphen-3-yl, biphen-4-yl, R11-substituted biphen-3-yl or R11-substituted biphen-4-yl, such as e.g. 2'-(R11)-biphen-4-yl, 3'-(R11)-biphen-4-yl or 4'-(R11)-biphen-4-yl, or 3'-(R11)-biphen-3-yl or 4'-(R11)-biphen-3-yl, in particular, 4'-fluoro-biphen-3-yl, 3'-fluoro-biphen-4-yl, 2'-fluoro-biphen-4-yl, 4'-methoxy-biphen-4-yl, 3'-methoxy-biphen-4-yl, 2'-methoxy-biphen-4-yl or 3'-acetylamino-biphen-4-yl, or 4'-methoxy-biphen-3-yl, 3'-methoxy-biphen-3-yl, 3'-nitro-biphen-4-yl or 3'-acetylamino-biphen-3-yl.

sub-embodiment of embodiment 3 refers to those compounds of formula I, which are from formula Ia, in which
R1 is biphenyl, or R11-substituted biphenyl,
  such as, for example, biphen-4-yl, or R11-substituted biphen-4-yl, such as e.g. 2'-(R11)-biphen-4-yl, 3'-(R11)-biphen-4-yl or 4'-(R11)-biphen-4-yl,
  in particular, 4'-fluoro-biphen-4-yl, 3'-fluoro-biphen-4-yl, 2'-fluoro-biphen-4-yl, 4'-biphen-4-yl, 3'-methoxy-biphen-4-yl, 2'-methoxy-biphen-4-yl or 3'-acetylamino-biphen-4-yl.

Another special embodiment (embodiment 4) of the compounds of formula I according to this invention refers to those compounds of formula I, in which
R1 is phenyl-pyridyl, such as, in particular, 6-phenyl-pyridin-3-yl.

Another special embodiment (embodiment 5) of the compounds of formula I according to this invention refers to those compounds of formula I, in which
R1 is (1N-methyl-pyrazolyl)-phenyl, such as, in particular, 4-(1 N-methyl-pyrazol-4-yl)-phenyl.

Another special embodiment (embodiment 6) of the compounds of formula I according to this invention refers to those compounds of formula I, in which
R2 is hydrogen.

Another special embodiment (embodiment 7) of the compounds of formula I according to this invention refers to those compounds of formula I, in which
R3 is -T-R30.

Another special embodiment (embodiment 8) of the compounds of formula I according to this invention refers to those compounds of formula I, in which
R3 is —U—Ar2.

Another special embodiment (embodiment 9) of the compounds of formula I according to this invention refers to those compounds of formula I, in which
R3 is —V-Har4.

Another special embodiment (embodiment 10) of the compounds of formula I according to this invention refers to those compounds of formula I, in which
R3 is Cyc2.

Another special embodiment (embodiment 11) of the compounds of formula I according to this invention refers to those compounds of formula I, in which
R3 is -T-R30, in which
T is 1-4C-alkylene, such as e.g. trimethylene,
R30 is amino.

Another special embodiment (embodiment 12) of the compounds of formula I according to this invention refers to those compounds of formula I, in which
R3 is —U—Ar2, in which
U is a direct bond,
Ar2 is 3-(R31)-phenyl or 4-(R31)-phenyl, in which
R31 is —W—R311, in which
W is a direct bond,
R311 is amidino or guanidino, such as e.g., especially,
R3 is 4-guanidino-phenyl.

Another special embodiment (embodiment 13) of the compounds of formula I according to this invention refers to those compounds of formula I, in which
R3 is —U—Ar2, in which
U is a direct bond,
Ar2 is 3-(R31)-phenyl or 4-(R31)-phenyl, in which
R31 is —W—R311, in which
W is a direct bond,
R311 is Het2, in which
Het2 is bonded to W via a ring carbon atom, and is piperidinyl, pyrrolidinyl or homopiperidinyl, such as e.g. piperidin-3-yl.

Another special embodiment (embodiment 14) of the compounds of formula I according to this invention refers to those compounds of formula I, in which
R3 is —U—Ar2, in which
U is a direct bond,
Ar2 is R31-substituted phenyl, or R31- and R32-substituted phenyl, in which
R31 is —W—R311, in which
W is 1-4C-alkylene, such as e.g. methylene, dimethylene or 1,1-dimethyl-methylene,
R311 is —N(R301)R302, in which
R301 is hydrogen, 1-4C-alkyl or hydroxy-2-4C-alkyl, such as e.g. hydrogen, methyl or 2-hydroxy-ethyl,
R302 is hydrogen,
R32 is fluorine, or in which, in particular,
R3 is —U—Ar2, in which
U is a direct bond,
Ar2 is 3-(R31)-phenyl, 4-(R31)-phenyl, or 4-(R31)-fluorophenyl, in which
R31 is —W—R311, in which
W is 1-4C-alkylene, such as e.g. methylene, dimethylene or 1,1-dimethyl-methylene,
R311 is —N(R301)R302, in which
R301 is hydrogen, 1-4C-alkyl or hydroxy-2-4C-alkyl, such as e.g. hydrogen, methyl or 2-hydroxy-ethyl,
R302 is hydrogen, such as e.g., especially,
R3 is 4-(aminomethyl)-phenyl, 3-(aminomethyl)-phenyl, 4-(2-aminoethyl)-phenyl,
2-fluoro-4-(aminomethyl)-phenyl,
4-(N-methyl-aminomethyl)-phenyl, or
4-[N-(2-hydroxyethyl)-aminomethyl]-phenyl.
In a special sub-embodiment of embodiment 14
R3 is 3-(R31)-phenyl, or 4-(R31)-phenyl, in which
R31 is —W—R311, in which
W is 1-4C-alkylene, especially straight chain 1-4C-alkylene, such as e.g. methylene or dimethylene,
R311 is amino, such as e.g., especially,
R3 is 3-(2-aminoethyl)-phenyl, 3-(aminomethyl)-phenyl, 4-(2-aminoethyl)-phenyl or 4-(aminomethyl)-phenyl.
In a more precise sub-embodiment of embodiment 14
R3 is 3-(2-aminoethyl)-phenyl.
In another more precise sub-embodiment of embodiment 14
R3 is 3-(aminomethyl)-phenyl.
In another more precise sub-embodiment of embodiment 14
R3 is 4-(2-aminoethyl)-phenyl.
In another more precise sub-embodiment of embodiment 14
R3 is 4-(aminomethyl)-phenyl.

Another special embodiment (embodiment 15) of the compounds of formula I according to this invention refers to those compounds of formula I, in which
R3 is —U—Ar2, in which
U is methylene substituted with amino-1-2C-alkyl,
Ar2 is R31- and R32-substituted phenyl, in which
R31 is chlorine,
R32 is chlorine, such as e.g., especially,
R3 is 1-(2-aminoethyl)-1-(3,4-dichloro-phenyl)-methyl or 1-(aminomethyl)-1-(3,4-dichloro-phenyl)-methyl.

Another special embodiment (embodiment 16) of the compounds of formula I according to this invention refers to those compounds of formula I, in which
R3 is —V-Har4, in which
V is a direct bond,
Har4 is R33-substituted thiophenyl, or, especially, R33-substituted pyridyl, or R33-substituted furanyl, in which
R33 is -Z-R331, in which
Z is 1-4C-alkylene, such as e.g. methylene,
R331 is amino, such as e.g., especially,
R3 is 6-(aminomethyl)-pyridin-3-yl, 2-(aminomethyl)-pyridin-4-yl, 6-(aminomethyl)-pyridin-2-yl, 5-(aminomethyl)-pyridin-3-yl or 5-(aminomethyl)-pyridin-2-yl, or 5-(aminomethyl)-furan-2-yl.

In a special sub-embodiment of embodiment 16
R3 is R33-substituted pyridyl, in which
R33 is -Z-R331, in which
Z is straight chain 1-4C-alkylene, such as e.g., especially, methylene,
R331 is amino.

Another special embodiment (embodiment 17) of the compounds of formula I according to this invention refers to those compounds of formula I, in which
R3 is Cyc2, in which
Cyc2 is

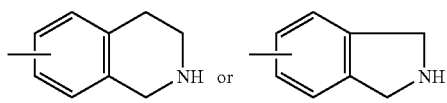

such as e.g. 1,2,3,4-tetrahydroisoquinolin-6-yl or 1,2,3,4-tetrahydroisoquinolin-7-yl, or isoindolin-5-yl or isoindolin-6-yl.

In a special sub-embodiment of embodiment 17
R3 is Cyc2, in which
Cyc2 is 1,2,3,4-tetrahydroisoquinolin-6-yl or 1,2,3,4-tetrahydroisoquinolin-7-yl,
especially
R3 is Cyc2, in which
Cyc2 is 1,2,3,4-tetrahydroisoquinolin-6-yl.

Another special embodiment (embodiment 18) of the compounds of formula I according to this invention refers to those compounds, which are from formula Ib,

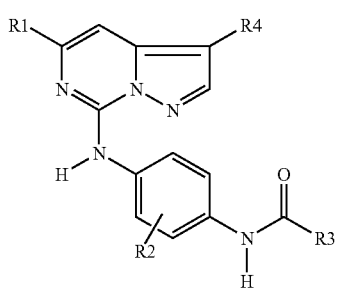

in which
R2 is hydrogen.

Embodiment 18 refers to those compounds of formula I, in which
the substituent —N(H)C(O)R3 is attached in the para position with respect to the binding position in which the phenyl ring is bonded to the pyrazolopyrimidinyl-amino moiety,
the substituent R4 is attached in the 3-position of the pyrazolopyrimidine scaffold, and
R2 is hydrogen.

Another special embodiment (embodiment 19) of the compounds of formula I according to this invention refers to those compounds, which are from formula Ic,

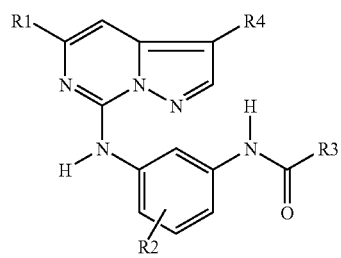

in which
R2 is hydrogen.

Embodiment 19 refers to those compounds of formula I, in which the substituent —N(H)C(O)R3 is attached in the meta position with respect to the binding position in which the phenyl ring is bonded to the pyrazolopyrimidinyl-amino moiety, the substituent R4 is attached in the 3-position of the pyrazolopyrimidine scaffold, and
R2 is hydrogen.

Another special embodiment (embodiment 20) of the compounds of formula I according to this invention refers to those compounds of formula I,
in which
R3 is T-R30, —U—Ar2, —V-Har4, or Cyc2, in which
T is straight chain 1-4C-alkylene,
R30 is —N(R301)R302, in which
R301 is hydrogen, 1-4C-alkyl or hydroxy-2-4C-alkyl,
R302 is hydrogen,
U is a bond, straight chain 1-4C-alkylene, or straight chain 1-4C-alkylene substituted with amino-1-4C-alkyl,
Ar2 is R31-substituted phenyl, or R31- and R32-substituted phenyl, in which
R31 is 1-4C-alkyl, fluorine, chlorine, guanidino, Het2, or —W—R311, in which
Het2 is bonded via a ring carbon atom to the phenyl moiety, and is pyrrolidinyl, piperidinyl or homopiperidinyl,
W is a bond or 1-4C-alkylene,
R311 has any one of the foregoing meanings of R30,
R32 is fluorine or chlorine,
V is a bond,
Har4 is substituted by R33, and is pyridyl, furanyl or thiophenyl, in which
R33 is -Z-R311, in which
Z is 1-4C-alkylene,
R331 has any one of the foregoing meanings of R30,
Cyc2 is

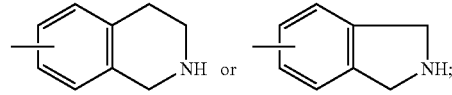

or in which, more precisely,
R3 is T-R30, —U—Ar2, —V-Har4, or Cyc2, in which
T is straight chain 1-4C-alkylene,
R30 is —N(R301)R302, in which
R301 is hydrogen, 1-2C-alkyl or hydroxy-2-3C-alkyl,
R302 is hydrogen, either
U is a bond,
Ar2 is R31-substituted phenyl, or R31- and R32-substituted phenyl, in which
R31 is guanidino, Het2, or —W—R311, in which
Het2 is bonded via a ring carbon atom to the phenyl moiety, and is pyrrolidinyl, piperidinyl or homopiperidinyl,
W is a bond or 1-4C-alkylene,
R311 has any one of the foregoing meanings of R30, and
R32 is fluorine, or
U is aminomethyl-methylene, or aminoethyl-methylene, and
Ar2 is 3,4-dichlorophenyl,
V is a bond,
Har4 is substituted by R33, and is pyridyl, furanyl or thiophenyl,
R33 is -Z-R311, in which
Z is 1-4C-alkylene,
R331 has any one of the foregoing meanings of R30,
Cyc2 is

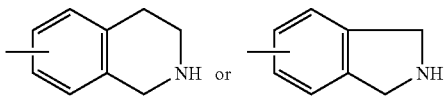

or in which, further more precisely,
R3 is T-R30, —U—Ar2, —V-Har4, or Cyc2, in which
T is straight chain 1-4C-alkylene,
R30 is amino, either
U is a bond,
Ar2 is 3-(R31)-phenyl, 4-(R31)-phenyl, or 3-(R31)- or 4-(R31)-fluorophenyl, in which
R31 is guanidino, Het2, amino, or —W—R311, in which
Het2 is bonded via a ring carbon atom to the phenyl moiety, and is pyrrolidinyl or piperidinyl,
W is 1-4C-alkylene,
R311 is —N(R301)R302, in which
R301 is hydrogen, methyl or 2-hydroxy-ethyl, and
R302 is hydrogen, or
U is aminomethyl-methylene, or (2-aminoethyl)-methylene, and
Ar2 is 3,4-dichlorophenyl,
V is a bond,
Har4 is substituted by R33, and is thiophenyl, or, especially, pyridyl or furanyl,
R33 is -Z-R311, in which
Z is 1-2C-alkylene,
R331 is amino,
Cyc2 is

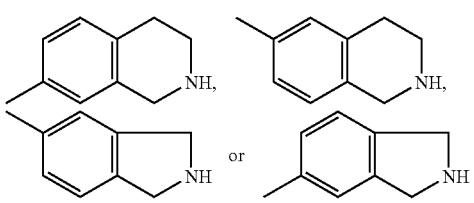

or in which, in particular precisely,

R3 is T-R30, —U—Ar2, —V-Har4, or Cyc2, in which
T is straight chain 1-4C-alkylene,
R30 is amino, either
U is a bond,
Ar2 is 3-(R31)-phenyl, 4-(R31)-phenyl, or 2-fluoro-4-(R31)-phenyl, in which
R31 is guanidino, Het2, amino, or —W—R311, in which
Het2 is piperidin-3-yl,
W is methylene, dimethylene or 1,1-dimethyl-methylene, especially methylene or dimethylene,
R311 is —N(R301)R302, in which
R301 is hydrogen, methyl or 2-hydroxy-ethyl, especially hydrogen, and
R302 is hydrogen, or
U is aminomethyl-methylene, or (2-aminoethyl)-methylene, and
Ar2 is 3,4-dichlorophenyl,
V is a bond,
Har4 is substituted by R33, and is pyridyl or furanyl,
R33 is -Z-R311, in which
Z is methylene,
R331 is amino,
Cyc2 is 1,2,3,4-tetrahydroisoquinolin-6-yl or 1,2,3,4-tetrahydroisoquinolin-7-yl;
or in which, in more particular precisely,
R3 is T-R30, —U—Ar2, —V-Har4, or Cyc2, in which
T is straight chain 1-4C-alkylene, such as e.g. trimethylene,
R30 is amino,
U is a bond,
Ar2 is 3-guanidino-phenyl, or 4-guanidino-phenyl, or 3-(R31)-phenyl, 4-(R31)-phenyl, or 2-fluoro-4-(R31)-phenyl, in which
R31 is —W—R311, in which
W is methylene or dimethylene,
R311 is —N(R301)R302, in which either
R301 is hydrogen,
R302 is hydrogen, or
R301 is methyl or 2-hydroxy-ethyl, and
R302 is hydrogen,
V is a bond,
Har4 is substituted by R33, and is pyridyl or furanyl,
R33 is -Z-R311, in which
Z is methylene,
R331 is amino, such as, for example,
Har4 is 6-(aminomethyl)-pyridin-3-yl, 2-(aminomethyl)-pyridin-4-yl, 6-(aminomethyl)-pyridin-2-yl, 5-(aminomethyl)-pyridin-3-yl, 4-(aminomethyl)-pyridin-2-yl, 5-(aminomethyl)-pyridin-2-yl, or 5-(aminomethyl)-furan-2-yl,
Cyc2 is 1,2,3,4-tetrahydroisoquinolin-6-yl or 1,2,3,4-tetrahydroisoquinolin-7-yl.

Another special embodiment (embodiment 21) of the compounds of formula I according to this invention refers to those compounds, which are from formula Ib or Ic, in which
R2 is hydrogen, and
R3 is any one selected from the group consisting of:
4-amino-phenyl, 4-tertbutyl-phenyl,
4-(piperidin-3-yl)-phenyl, 3-(piperidin-3-yl)-phenyl, 4-(1-amino-1-methyl-ethyl)-phenyl, 3-(1-amino-1-methyl-ethyl)-phenyl,
1-(2-aminoethyl)-1-(3,4-dichloro-phenyl)-methyl, 1-(aminomethyl)-1-(3,4-dichloro-phenyl)-methyl,
4-(aminomethyl)-phenyl, 3-(aminomethyl)-phenyl, 2-(aminomethyl)-phenyl,
4-(2-aminoethyl)-phenyl, 3-(2-aminoethyl)-phenyl
3-aminopropyl,
2-fluoro-4-(aminomethyl)-phenyl,
4-(N-methyl-aminomethyl)-phenyl, 3-(N-methyl-aminomethyl)-phenyl,
1,2,3,4-tetrahydroisoquinolin-6-yl, 1,2,3,4-tetrahydroisoquinolin-7-yl
4-guanidino-phenyl, 3-guanidino-phenyl
4-[N-(2-hydroxyethyl)-aminomethyl]-phenyl,
6-(aminomethyl)-pyridin-3-yl, 2-(aminomethyl)-pyridin-4-yl, 6-(aminomethyl)-pyridin-2-yl, 5-(aminomethyl)-pyridin-3-yl, 4-(aminomethyl)-pyridin-2-yl, 5-(aminomethyl)-pyridin-2-yl, and 5-(aminomethyl)-furan-2-yl;

or in which, in particular,
R2 is hydrogen, and
R3 is any one selected from the group consisting of:
4-(aminomethyl)-phenyl, 3-(aminomethyl)-phenyl,
4-(2-aminoethyl)-phenyl,
3-aminopropyl,
2-fluoro-4-(aminomethyl)-phenyl,
4-(N-methyl-aminomethyl)-phenyl,
1,2,3,4-tetrahydroisoquinolin-6-yl, 1,2,3,4-tetrahydroisoquinolin-7-yl
4-guanidino-phenyl,
4-[N-(2-hydroxyethyl)-aminomethyl]-phenyl,
6-(aminomethyl)-pyridin-3-yl, 2-(aminomethyl)-pyridin-4-yl, 6-(aminomethyl)-pyridin-2-yl, 5-(aminomethyl)-pyridin-3-yl, 5-(aminomethyl)-pyridin-2-yl, and
5-(aminomethyl)-furan-2-yl.

Another special embodiment (embodiment 22) of the compounds of formula I according to this invention refers to those compounds, which are from formula Ib or Ic, in which
R1 is any one selected from the group consisting of:
dibenzofuran-4-yl, biphen-3-yl, biphen-4-yl,
6-benzyloxy-naphthalen-2-yl, 6-hydroxy-naphthalen-2-yl, 6-methoxy-naphthalen-2-yl, 6-ethoxy-naphthalen-2-yl, 6-[2-(methoxyethoxy)]-naphthalen-2-yl, 6-[2-(hydroxyethoxy)]-naphthalen-2-yl, 4'-fluoro-biphen-4-yl, 3'-fluoro-biphen-4-yl, 2'-fluoro-biphen-4-yl, 4'-methoxy-biphen-4-yl, 3'-methoxy-biphen-4-yl, 2'-methoxy-biphen-4-yl, 3'-acetylamino-biphen-4-yl, 4'-methoxy-biphen-3-yl, 3'-methoxy-biphen-3-yl, 3'-nitro-biphen-4-yl, 3'-acetylamino-biphen-3-yl, 6-phenyl-pyridin-3-yl and 4-(1N-methyl-pyrazol-4-yl)-phenyl, and
R2 is hydrogen.

A sub-embodiment of embodiment 22 refers to those compounds which are from formula Ib or Ic, in which
R1 is any one selected from the group consisting of:
dibenzofuran-4-yl,
6-benzyloxy-naphthalen-2-yl, 6-hydroxy-naphthalen-2-yl, 6-methoxy-naphthalen-2-yl, 6-ethoxy-naphthalen-2-yl, 6-[2-(methoxyethoxy)]-naphthalen-2-yl, 6-[2-(hydroxyethoxy)]-naphthalen-2-yl, 4'-fluoro-biphen-4-yl, 3'-fluoro-biphen-4-yl, 2'-fluoro-biphen-4-yl, 4'-methoxy-biphen-4-yl, 3'-methoxy-biphen-4-yl, 2'-methoxy-biphen-4-yl, 3'-acetylamino-biphen-4-yl, 6-phenyl-pyridin-3-yl and 4-(1N-methyl-pyrazol-4-yl)-phenyl, R2 is hydrogen, and
R4 is hydrogen.

Another special embodiment (embodiment 23) of the compounds of formula I according to this invention refers to those compounds of formula I, in which R4 is hydrogen.

Another special embodiment (embodiment 24) of the compounds of formula I according to this invention refers to those compounds of formula I, which are from formula Ib in which R4 is hydrogen.

Another special embodiment (embodiment 25) of the compounds of formula I according to this invention refers to those compounds of formula I, which are from formula Ic in which R4 is hydrogen.

Another special embodiment (embodiment 26) of the compounds of formula I according to this invention refers to those compounds of formula I, in which R4 is bromine.

Another special embodiment (embodiment 27) of the compounds of formula I according to this invention refers to those compounds of formula I, which are from formula Ib in which R4 is bromine.

Another special embodiment (embodiment 28) of the compounds of formula I according to this invention refers to those compounds of formula I, which are from formula Ic in which R4 is bromine.

It is to be understood, that the present invention also includes any or all possible combinations and subsets of the embodiments defined herein afore.

Exemplary compounds according to the present invention may include, without being restricted thereto, any compounds of formula I selected from the group consisting of those compounds of formula I disclosed in the following examples as final compounds, particularly any compounds of formula I selected from those compounds of formula I listed in any of the Tables A to H in the appended "Biological Investigations", as well as the salts thereof.

The compounds according to the invention can be prepared, for example, as described as follows and according to the following specified reaction steps, or, particularly, in a manner as described by way of example in the following examples, or analogously or similarly thereto according to preparation procedures or synthesis strategies known to the person skilled in the art.

Compounds of formula I, in which R1, R2 and R3 have the meanings mentioned above and R4 is either hydrogen (i.e. compounds of formula Ia) or halogen, particularly bromine, can be obtained as shown in the reaction schemes 1 and 2 below.

As shown in the steps of the synthesis route outlined in scheme 1, compounds of the formula V, in which R1 has one of the meanings mentioned above, can be converted into corresponding compounds of formula IV with the aid of e.g. thiosemicarbazide. Said cyclization reaction can be carried out as known to the skilled person or as described in the following examples, advantageously in a suitable solvent, for example an alcohol (e.g. ethanol) at elevated temperature, such as e.g. reflux temperature of ethanol.

Compounds of formula V are art-known or can be obtained as shown exemplarily below according to known steps, such as e.g., via a first step, which is C-acylation of a ketone enolate with a carboxylic acid derivative R1-C(O)X, in which R1 has one of the meanings mentioned above and X is a suitable leaving group, such as e.g. chlorine, or in which R1-C(O)X is prepared in situ from the corresponding free acid R1-C(O)OH by a suitable activating reagent, such as e.g. carbonyldiimidazole (CDI). In a subsequent second step, the intermediate obtained can than be cyclized to compounds of formula V, or, alternatively, it can be directly converted with thiosemicarbazide via abovementioned cyclization reaction into compounds of formula IV. Said reactions can be carried out in a manner customary per se to the skilled person or as described in the following examples.

The ketone enolate mentioned can be obtained in situ, as it is known per se to the skilled person, with the aid of a suitable base, like lithium hexamethyldisilazide at reduced temperature as described in the following examples.

Compounds of formula IV can be converted into compounds of formula III by alkylation, particularly methylation, reaction, and then, optionally, introduction of the radical R4, in which R4 is halogen, particularly bromine. Compounds of formula III can be oxidized to obtain corresponding compounds of formula II, in which R4 stands for hydrogen or halogen.

Said steps can be performed as it is known to the skilled person or as described in the following examples, using e.g. methyl iodide as methylation reagent, a suitable halogenating reagent, such as e.g., when R4 is bromine, N-bromosuccinimide giving predominantly the 3-bromo-pyrazolo[1,5-c]pyrimidine derivatives, and a suitable peracid (e.g. m-chloroperbenzoic acid) as oxidation reagent.

As shown in reaction scheme 2, compounds of formula II, in which R1 has one of the meanings indicated above and R4 stands for hydrogen or halogen, can be reacted with compounds of formula VII, in which R2 has the meaning given above and PGI is a suitable protective group, such as for example tertbutoxycarbonyl (Boc) or one of those mentioned in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000), in a nucleophilic substitution reaction. Subsequent deprotection of the protecting group PGI in a manner habitual per se to the skilled person or as described in the following examples gives the corresponding free amino compounds of formula VI. Said reactions can be carried out in a manner known to the skilled person or as described in the following examples.

Reaction scheme 1:

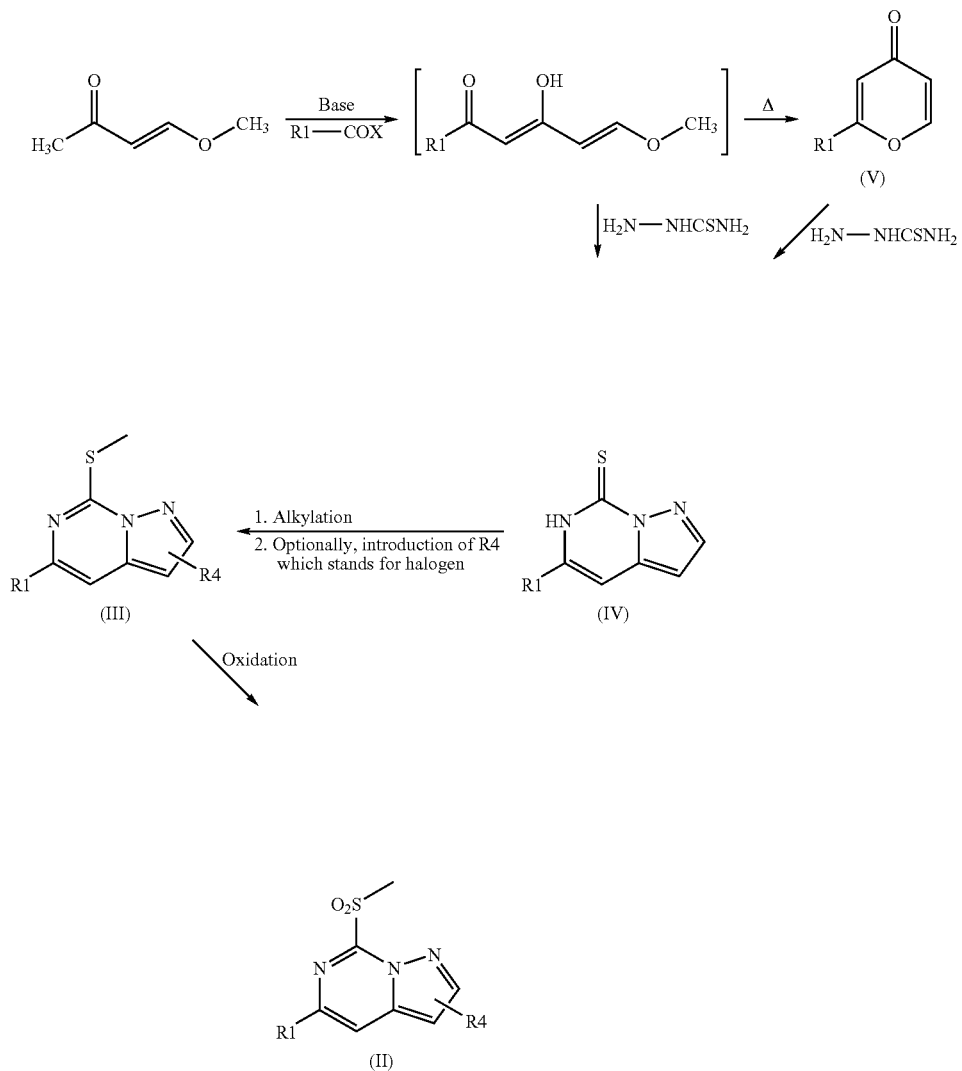

Reaction scheme 2:

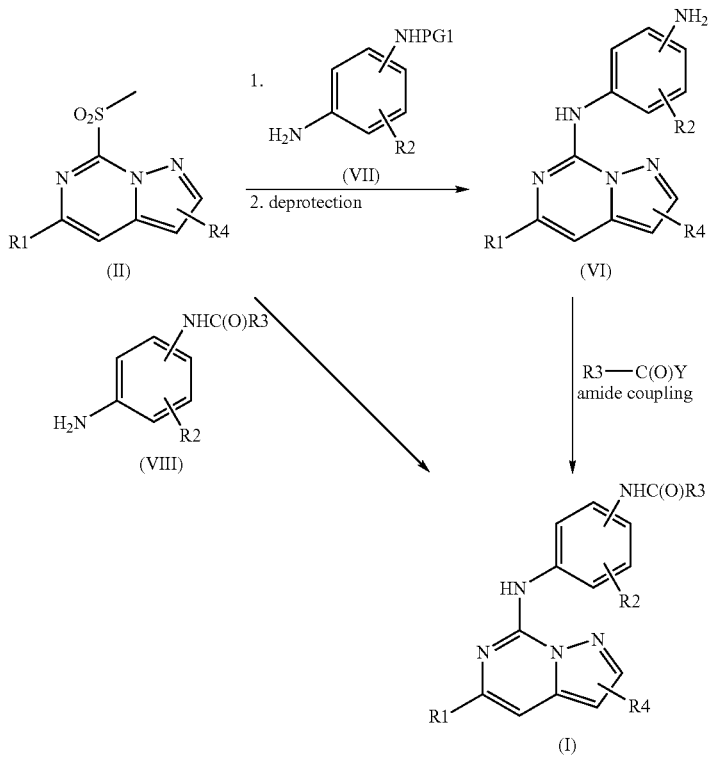

Compounds of formula VI can be converted to corresponding compounds of formula I. Said conversion can be obtained by reaction with compounds of formula R3-C(O)—Y, in which Y is a suitable leaving group, preferably a chlorine atom, and R3 stands for the substituents given above, which can be, if necessary, protected by temporary protective groups known to the person skilled in the art (such as e.g. the tertbutoxycarbonyl protective group for an amino function), to give, after optional removal of said temporary protective groups, compounds of formula I, in which R1, R2, R3 and R4 have the meanings mentioned above.

Alternatively, compounds of formula I, in which R1, R2, R3 and R4 have the meanings mentioned above, can be also obtained from compounds of formula VI by reaction with compounds of formula R3-C(O)—Y, in which Y is hydroxyl and R3 stands for the substituents given above, which can be, if necessary, protected by temporary protective groups known to the person skilled in the art (such as e.g. the tertbutoxycarbonyl protective group for an amino function), by reaction with amide bond linking reagents known to the person skilled in the art and subsequential optional removal of said temporary protective groups. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetra-methyluronium tetrafluoroborate or O-(benzotriazol-1-yl)-N,N,N',N'-tetramethyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride.

Said reactions of compounds of formula VI with compounds of formula R3-C(O)—Y can be carried out in an art-known manner or as described in the following examples.

Compounds of formula R3-C(O)—Y are known or can be obtained in a known manner or analogously or similarly to art-known compounds.

Yet alternatively, compounds of formula I, in which R1, R2, R3 and R4 have the meanings mentioned above, can be also obtained from compounds of formula II by reaction with compounds of formula VIII, in which R2 has the meanings indicated above and R3 stands for the substituents given above which can be, if necessary, protected by temporary protective groups known to the person skilled in the art (such as e.g. the tertbutoxycarbonyl protective group for an amino function), and subsequential optional removal of said temporary protective groups.

Said reactions of compounds of formula II with compounds of formula VIII can be carried out in an art-known manner or as described in the following examples.

Compounds of formula VIII are known or can be obtained in a known manner or analogously or similarly to art-known compounds, or they are accessible as described in the following examples or analogously or similarly thereto.

If suitable, compounds accessible as described herein which contain a (hetero)aromatic ring substituted by iodine or bromine or trifluoromethansulfonyloxy, such as e.g., without being restricted thereto, compounds of formula I or III, in which R1 is a (hetero)aromatic ring, particularly phenyl, substituted by iodine or bromine and R4 is hydrogen, or compounds of formula I or III, in which R1 is a (hetero)aromatic ring, particularly phenyl, substituted by iodine and R4 is bromine, can be subjected to a CC-bond formation reaction (e.g. aryl-aryl coupling) with suitable (hetero)aryl derivatives to give corresponding compounds containing a (hetero)aryl-(hetero)aryl radical. Said CC-bond formation reaction may be also, for example, a Kumada coupling, a Negishi coupling, a Hiyama coupling, a Stille reaction or, particularly, a Suzuki coupling reaction. Thus, for example, in the case of a Suzuki coupling reaction, compounds of formula I or III, in which R1 is a (hetero)aromatic ring substituted by iodine or bromine, can be reacted with (hetero)aryl-boronic acids or esters, such as, for example, phenyl-boronic acids (such as e.g. R11-substituted phenyl-boronic acids), to obtain a corresponding CC-coupled group, such as, for example, a (hetero)aryl-(hetero)aryl, e.g. a bisaryl or, in more detail, bisphenyl group.

Suitably, the Suzuki reaction can be carried out as it is known to the person of ordinary skill in the art and/or in a manner as it is described below and specified by way of example in the following examples or analogously or similarly thereto.

In more detail, the Suzuki reaction mentioned can be carried out in organic solvents alone, for example in toluene, benzene, dimethylformamide or in ethereal (e.g. dimethoxyethane or dioxane) or alcohol solvents or in a mixture thereof, or preferably in a mixture comprising an organic solvent (e.g. dimethoxyethane) and water, with organic (e.g. triethylamine) or preferably inorganic base (e.g. potassium hydroxide, thallium hydroxide, sodium bicarbonate, cesium carbonate, cesium fluoride or, in particular, potassium or sodium carbonate) in the presence of a transition metal catalyst, for example, a nickel or, in particular, palladium catalyst (e.g. $Pd(OAc)_2$, $PdCl_2(PPh_3)_2$ or $Pd(PPh_3)_4$), and, optionally, lithium chloride.

Optionally, compounds of a given formula, which can be prepared as described herein, may converted into further compounds of the respective formula by methods known to one of ordinary skill in the art. Thus e.g., optionally, compounds of formula I can be converted into further compounds of formula I by methods known to one of ordinary skill in the art. More specifically, for example, from compounds of the formula I in which a) R11 is benzyloxy, the corresponding free hydroxy compounds can be obtained by hydrogenation reactions;
b) R11 is hydroxyl, the corresponding O-ether compounds can be obtained by etherification reactions;
c) R301 or R303 is 1-4C-alkoxycarbonyl, such as e.g. a tertbutoxycarbonyl group, the corresponding free amino compounds can be obtained by removal of the 1-4C-alkoxycarbonyl group;
d) R30 is a cyano group, the corresponding amidino group can be obtained by imidoester formation and subsequential amination.
e) R301 and/or R302 is hydrogen, the corresponding N-ether compounds can be obtained by etherification reactions.
f) R30 is an amino group, the corresponding guanidino group can be obtained by guanidination reaction with the aid of suitable guanidino forming agents.

The methods mentioned under a) to f) can be expediently carried out analogously to the methods known to the person skilled in the art or as described by way of example in the following examples.

Optionally, compounds of the formula I can be converted into their salts, or, optionally, salts of the compounds of the formula I can be converted into the free compounds. Corresponding processes are habitual per se to the skilled person.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts can be obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts can be obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds according to this invention. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples serve to illustrate the invention further without restricting it. Likewise, further compounds according to this invention, whose preparation is not explicitly described, can be prepared in an analogous or similar manner or in a manner familiar per se to the person skilled in the art using customary process techniques.

Any or all of the compounds of formula I according to the present invention which are specified as final compounds in the following examples, as well as the salts thereof, are a particularly interesting subject of the present invention.

In the examples, mp stands for melting point, h for hour(s), min for minutes, conc. for concentrated, Boc for the tertbutoxycarbonyl group, calc. for calculated, fnd. for found, and other abbreviations have their meanings customary per se to the skilled person.

EXAMPLES

Final Compounds 1. 4-Aminomethyl-N-[4-(5-biphenyl-4-yl-pyrazolo[1,5-c]pyrimidin-7-ylamino)-phenyl]-benzamide; compound with 2,2,2-trifluoro-acetic acid A mixture of {4-[4-(5-biphenyl-4-yl-pyrazolo[1,5-c]pyrimidin-7-ylamino)-phenylcarbamoyl]benzyl}-carbamic acid tert-butyl ester (compound A1)(0.14 g) and trifluoroacetic acid (TFA)(1 ml) in dichloromethane (5 ml) is stirred 3 h at ambient temperature. The reaction mixture is evaporated, coevaporated with toluene and dried at high vacuum. Colorless crystals (0.13 g) are obtained in quantitative yield and a transition temperature of 170° C. and a melting temperature at 230° C.

Starting from the appropriate starting compounds, which are mentioned or described explicitly below, or which can be prepared in a manner known to the person skilled in the art or analogously or similarly to the examples described by way of example herein, the following and also further relevant, non-explicitly described analogous compounds can be obtained according to the procedure as in Example 1 or analogously or similarly thereto, or according to any procedure customary per se to the skilled person and/or described herein.

2. N-{4-[5-(3-Bromo-phenyl)-pyrazolo[1,5-c]pyrimidin-7-ylamino]-phenyl}-4-(4-methyl-piperazin-1-ylmethyl)-benzamide MS: calc.: C, 31; H, 30; Br, N, 7; O, (596.54). fnd.: [M+1] 586.3//598.3.

3. 4-Amino-N-{4-[5-(3-bromo-phenyl)-pyrazolo[1,5-c]pyrimidin-7-ylamino]-phenyl}-benzamide; compound with 2,2,2-trifluoro-acetic acid MS: calc.: C, 25; H, 19; Br, N, 6; O, (499.37). fnd.: [M+1]: 499.4//501.4.

4. 4-Amino-N-[4-(5-biphenyl-3-yl-pyrazolo[1,5-c]pyrimidin-7-ylamino)-phenyl]-benzamide; compound with 2,2,2-trifluoro-acetic acid MS: calc.: C, 31; H, 24; N, 6; O, (496.58). fnd.: [M+1]: 497.4.

5. N-[4-(5-Dibenzofuran-4-yl-pyrazolo[1,5-c]pyrimidin-7-ylamino)-phenyl]-4-(4-methyl-piperazin-1-ylmethyl)-benzamide MS: calc.: C, 37; H, 33; N, 7; O, 2; (607.72). fnd.: [M+1]: 608.4.

6. 4-Amino-N-[4-(5-dibenzofuran-4-yl-pyrazolo[1,5-c]pyrimidin-7-ylamino)-phenyl]-benzamide; compound with 2,2,2-trifluoro-acetic acid MS: calc.: C, 31; H, 22; N, 6; O, 2; (510.56). fnd.: [M+1]: 511.5.

7. N-[4-(5-Dibenzofuran-4-yl-pyrazolo[1,5-c]pyrimidin-7-ylamino)-phenyl]-benzamide MS: calc.: C, 31; H, 21; N, 5; O, 2; (495.55). fnd.: [M+1]: 496.5.

8. N-[4-(5-Dibenzofuran-4-yl-pyrazolo[1,5-c]pyrimidin-7-ylamino)-phenyl]-isonicotinamide MS: calc.: C, 30; H, 20; N, 6; O, 2; (496.53). fnd.: [M+1]: 497.5.

9. N-[4-(5-Dibenzofuran-4-yl-pyrazolo[1,5-c]pyrimidin-7-ylamino)-phenyl]-4-fluoro-benzamide MS: calc.: C, 31; H, 20; F, N, 5; O, 2; (513.54). fnd.: [M+1]: 514.5.

10. 4-tert-Butyl-N-[4-(5-dibenzofuran-4-yl-pyrazolo[1,5-c]pyrimidin-7-ylamino)-phenyl]-benzamide MS: calc.: C, 35; H, 29; N, 5; O, 2; (551.65). fnd.: [M+1]: 552.4.

11. N-[4-(5-Dibenzofuran-4-yl-pyrazolo[1,5-c]pyrimidin-7-ylamino)-phenyl]-2-(4-methoxy-phenyl)-acetamide MS: calc.: C, 33; H, 25; N, 5; O, 3; (539.60). fnd.: [M+1]: 540.4.

12. 2-(3-Chloro-phenyl)-N-[4-(5-dibenzofuran-4-yl-pyrazolo[1,5-c]pyrimidin-7-ylamino)-phenyl]-acetamide MS: calc.: C, 32; H, 22; Cl, N, 5; O, 2; (544.02). fnd.: [M+1]: 544.3.

13. Furan-2-carboxylic acid [4-(5-dibenzofuran-4-yl-pyrazolo[1,5-c]pyrimidin-7-ylamino)-phenyl]-amide MS: calc.: C, 29; H, 19; N, 5; O, 3; (485.51). fnd.: [M+1]: 486.4.

14. Furan-2-carboxylic acid [3-(5-dibenzofuran-4-yl-pyrazolo[1,5-c]pyrimidin-7-ylamino)-phenyl]-amide MS: calc.: C, 29; H, 19; N, 5; O, 3; (485.51). fnd.: [M+1]: 486.3.

15. 4-tert-Butyl-N-[3-(5-dibenzofuran-4-yl-pyrazolo[1,5-c]pyrimidin-7-ylamino)-phenyl]-benzamide MS: calc.: C, 35; H, 29; N, 5; O, 2; (551.65). fnd.: [M+1]: 552.4.

16. N-[3-(5-Dibenzofuran-4-yl-pyrazolo[1,5-c]pyrimidin-7-ylamino)-phenyl]-2-(4-methoxy-phenyl)-acetamide MS: calc.: C, 33; H, 25; N, 5; O, 3; (539.60). fnd.: [M+1]: 540.4.

17. 4-Aminomethyl-N-[3-(5-dibenzofuran-4-yl-pyrazolo[1,5-c]pyrimidin-7-ylamino)-phenyl]-benzamide; compound with 2,2,2-trifluoro-acetic acid MS: calc.: C, 32; H, 24; N, 6; O, 2; (524.59). fnd.: [M+1]: 525.3.

18. 3-Aminomethyl-N-[3-(5-dibenzofuran-4-yl-pyrazolo[1,5-c]pyrimidin-7-ylamino)-phenyl]-benzamide; compound with 2,2,2-trifluoro-acetic acid MS: calc.: C, 32; H, 24; N, 6; O, 2; (524.59). fnd.: [M+1]: 525.3.

19. 4-Aminomethyl-N-[4-(5-dibenzofuran-4-yl-pyrazolo[1,5-c]pyrimidin-7-ylamino)-phenyl]-benzamide; compound with 2,2,2-trifluoro-acetic acid MS: calc.: C, 32; H, 24; N, 6; O, 2; (524.59). fnd.: [M+1]: 525.3.

20. 3-Aminomethyl-N-[4-(5-dibenzofuran-4-yl-pyrazolo[1,5-c]pyrimidin-7-ylamino)-phenyl]-benzamide with 2,2,2-trifluoro-acetic acid MS: calc.: C, 32; H, 24; N, 6; O, 2; (524.59). fnd.: [M+1]: 525.3.

21. 4-(2-Amino-ethyl)-N-[3-(5-dibenzofuran-4-yl-pyrazolo[1,5-c]pyrimidin-7-ylamino)-phenyl]-benzamide with 2,2,2-trifluoro-acetic acid MS: calc.: C, 33; H, 26; N, 6; O, 2; (538.61). fnd.: [M+1]: 539.4.

22. 4-Amino-N-[3-(5-dibenzofuran-4-yl-pyrazolo[1,5-c]pyrimidin-7-ylamino)-phenyl]-butyramide with 2,2,2-trifluoro-acetic acid MS: calc.: C, 28; H, 24; N, 6; O, 2; (476.54). fnd.: [M+1]: 477.2.

23. 4-(2-Amino-ethyl)-N-[4-(5-dibenzofuran-4-yl-pyrazolo[1,5-c]pyrimidin-7-ylamino)-phenyl]-benzamide with 2,2,2-trifluoro-acetic acid MS: calc.: C, 33; H, 26; N, 6; O, 2; (538.61). fnd.: [M+1]: 539.4.

24. 4-Amino-N-[4-(5-dibenzofuran-4-yl-pyrazolo[1,5-c]pyrimidin-7-ylamino)-phenyl]-butyramide with 2,2,2-trifluoro-acetic acid MS: calc.: C, 28; H, 24; N, 6; O, 2; (476.54). fnd.: [M+1]: 477.2.

25. 2-Amino-N-[4-(5-dibenzofuran-4-yl-pyrazolo[1,5-c]pyrimidin-7-ylamino)-phenyl]-benzamide with 2,2,2-trifluoro-acetic acid MS: calc.: C, 31; H, 22; N, 6; O, 2;(510.56). fnd.: [M+1]: 511.3.

26. 3,4-Dichloro-N-[4-(5-dibenzofuran-4-yl-pyrazolo[1,5-c]pyrimidin-7-ylamino)-phenyl]-benzamide Mp [° C.]: >300

27. 4-Aminomethyl-N-[3-(5-dibenzofuran-4-yl-pyrazolo[1,5-c]pyrimidin-7-ylamino)-phenyl]-2-fluoro-benzamide Mp [° C.]: 225-227

28. 4-Aminomethyl-N-[4-(5-dibenzofuran-4-yl-pyrazolo[1,5-c]pyrimidin-7-ylamino)-phenyl]-2-fluoro-benzamide Mp [° C.]: 233-235

29. 6-Aminomethyl-N-[4-(5-dibenzofuran-4-yl-pyrazolo[1,5-c]pyrimidin-7-ylamino)-phenyl]-nicotinamide Mp [° C.]: 249-252

30. 2-Aminomethyl-N-[4-(5-dibenzofuran-4-yl-pyrazolo[1,5-c]pyrimidin-7-ylamino)-phenyl]-isonicotinamide Mp [° C.]: 235-236 decomp.

31. N-[4-(5-Dibenzofuran-4-yl-pyrazolo[1,5-c]pyrimidin-7-ylamino)-phenyl]-4-dimethylaminomethyl-benzamide Mp [° C.]: 283-285

32. N-[3-(5-Dibenzofuran-4-yl-pyrazolo[1,5-c]pyrimidin-7-ylamino)-phenyl]-4-methylaminomethyl-benzamide; compound with 2,2,2-trifluoro-acetic acid Mp [° C.]: 164-166

33. N-[4-(5-Dibenzofuran-4-yl-pyrazolo[1,5-c]pyrimidin-7-ylamino)-phenyl]-4-methylaminomethyl-benzamide; compound with 2,2,2-trifluoro-acetic acid Mp [° C.]: 238-250 amorpheous 34. 1,2,3,4-Tetrahydro-isoquinoline-7-carboxylic acid [3-(5-dibenzofuran-4-yl-pyrazolo[1,5-c]pyrimidin-7-ylamino)-phenyl]-amide; compound with 2,2,2-trifluoro-acetic acid Mp [° C.]: 230 decomposition 35. 1,2,3,4-Tetrahydro-isoquinoline-7-carboxylic acid [4-(5-dibenzofuran-4-yl-pyrazolo[1,5-c]pyrimidin-7-ylamino)-phenyl]-amide; compound with 2,2,2-trifluoro-acetic acid Mp [° C.]: 235-7

36. N-[3-(5-Dibenzofuran-4-yl-pyrazolo[1,5-c]pyrimidin-7-ylamino)-phenyl]-4-piperidin-3-yl-benzamide; compound with 2,2,2-trifluoro-acetic acid Mp [° C.]: amorpheous 37. N-[3-(5-Dibenzofuran-4-yl-pyrazolo[1,5-c]pyrimidin-7-ylamino)-phenyl]-4-piperidin-3-yl-benzamide; compound with 2,2,2-trifluoro-acetic acid Mp [° C.]: 310-312

38. 5-Aminomethyl-furan-2-carboxylic acid [4-(5-dibenzofuran-4-yl-pyrazolo[1,5-c]pyrimidin-7-ylamino)-phenyl]-amide; compound with 2,2,2-trifluoro-acetic acid Mp [° C.]: 250

39. 4-(1-Amino-1-methyl-ethyl)-N-[4-(5-dibenzofuran-4-yl-pyrazolo[1,5-c]pyrimidin-7-ylamino)-phenyl]-benzamide; compound with 2,2,2-trifluoro-acetic acid Mp [° C.]: amorph 40. 4-(1-Amino-1-methyl-ethyl)-N-[3-(5-dibenzofuran-4-yl-pyrazolo[1,5-c]pyrimidin-7-ylamino)-phenyl]-benzamide; compound with 2,2,2-trifluoro-acetic acid Mp [° C.]: 142

41. rac-3-Amino-N-[3-(5-dibenzofuran-4-yl-pyrazolo[1,5-c]pyrimidin-7-ylamino)-phenyl]-2-(3,4-dichloro-phenyl)-propionamide; compound with 2,2,2-trifluoro-acetic acid Mp [° C.]: 142-146

42. 4-Aminomethyl-N-{4-[5-(6-benzyloxy-naphthalen-2-yl)-pyrazolo[1,5-c]pyrimidin-7-ylamino]-phenyl}-benzamide; compound with 2,2,2-trifluoro-acetic acid Mp [° C.]: 252-4 decomp.

43. rac-4-Amino-N-[4-(5-dibenzofuran-4-yl-pyrazolo[1,5-c]pyrimidin-7-ylamino)-phenyl]-2-(3,4-dichloro-phenyl)-butyramide; compound with 2,2,2-trifluoro-acetic acid Mp [° C.]: 188-190

44. 4-Aminomethyl-N-{4-[5-(6-hydroxy-naphthalen-2-yl)-pyrazolo[1,5-c]pyrimidin-7-ylamino]-phenyl}-benzamide; compound with 2,2,2-trifluoro-acetic acid Mp [° C.]: 204-6 sintering at 180

45. 4-Aminomethyl-N-{4-[5-(6-methoxy-naphthalen-2-yl)-pyrazolo[1,5-c]pyrimidin-7-ylamino]-phenyl}-benzamide; compound with 2,2,2-trifluoro-acetic acid Mp [° C.]: 172-5

46. 4-Aminomethyl-N-{4-[5-(6-ethoxy-naphthalen-2-yl)-pyrazolo[1,5-c]pyrimidin-7-ylamino]-phenyl}-benzamide; compound with 2,2,2-trifluoro-acetic acid Mp [° C.]: 245

47. 4-Aminomethyl-N-(4-{5-[6-(2-methoxy-ethoxy)-naphthalen-2-yl]-pyrazolo[1,5-c]pyrimidin-7-ylamino}-phenyl)-benzamide compound with 2,2,2-trifluoro-acetic acid Mp [° C.]: 242-3 decomp 48. N-[4-(5-Dibenzofuran-4-yl-pyrazolo[1,5-c]pyrimidin-7-ylamino)-phenyl]-4-guanidino-benzamide hydrochloride Mp [° C.]: 299-302

49. {6-[7-(4-{[1-(4-Aminomethyl-phenyl)-methanoyl]-amino}-phenylamino)-pyrazolo[1,5-c]pyrimidin-5-yl]-naphthalen-2-yloxy}-acetic acid; compound with 2,2,2-trifluoro-acetic acid Mp [° C.]: >320

50. Aminomethyl-N-(4-{5-[6-(2-hydroxy-ethoxy)-naphthalen-2-yl]-pyrazolo[1,5-c]pyrimidin-7-ylamino}-phenyl)-benzamide; compound with 2,2,2-trifluoro-acetic acid Mp [° C.]: 182-4 sintering at 168

51. 6-Aminomethyl-pyridine-2-carboxylic acid [4-(5-dibenzofuran-4-yl-pyrazolo[1,5-c]pyrimidin-7-ylamino)-phenyl]-amide; compound with 2,2,2-trifluoro-acetic acid Mp [° C.]: 246-250

52. 5-Aminomethyl-N-[4-(5-dibenzofuran-4-yl-pyrazolo[1,5-c]pyrimidin-7-ylamino)-phenyl]-nicotinamide; compound with 2,2,2-trifluoro-acetic acid Mp [° C.]: 201-204

53. 4-Aminomethyl-pyridine-2-carboxylic acid [4-(5-dibenzofuran-4-yl-pyrazolo[1,5-c]pyrimidin-7-ylamino)-phenyl]-amide; compound with 2,2,2-trifluoro-acetic acid Mp [° C.]: 224-227

54. 4-Aminomethyl-N-{4-[5-(6-phenyl-pyridin-3-yl)-pyrazolo[1,5-c]pyrimidin-7-ylamino]-phenyl}-benzamide; compound with 2,2,2-trifluoro-acetic acid Mp [° C.]: 217 decomposition 55. 4-Aminomethyl-N-{4-[5-(4'-methoxy-biphenyl-4-yl)-pyrazolo[1,5-c]pyrimidin-7-ylamino]-phenyl}-benzamide; compound with 2,2,2-trifluoro-acetic acid Mp [° C.]: 233

56. 4-Aminomethyl-N-{4-[5-(2'-methoxy-biphenyl-4-yl)-pyrazolo[1,5-c]pyrimidin-7-ylamino]-phenyl}-benzamide; compound with 2,2,2-trifluoro-acetic acid Mp [° C.]: 138 Color change at 151

57. N-[4-(5-Dibenzofuran-4-yl-pyrazolo[1,5-c]pyrimidin-7-ylamino)-phenyl]-4-[(2-hydroxy-ethylamino)-methyl]-benzamide; compound with 2,2,2-trifluoro-acetic acid Mp [° C.]: amorpheous 58. 1,2,3,4-Tetrahydro-isoquinoline-6-carboxylic acid [4-(5-dibenzofuran-4-yl-pyrazolo[1,5-c]pyrimidin-7-ylamino)-phenyl]-amide; compound with 2,2,2-trifluoro-acetic acid Mp [° C.]: 215-217 decomposition 59. 4-Aminomethyl-N-{4-[5-(3'-methoxy-biphenyl-4-yl)-pyrazolo[1,5-c]pyrimidin-7-ylamino]-phenyl}-benzamide compound with 2,2,2-trifluoro-acetic acid Mp [° C.]: 226-233° C.

60. N-{4-[5-(3'-Acetylamino-biphenyl-4-yl)-pyrazolo[1,5-c]pyrimidin-7-ylamino]-phenyl}-4-aminomethyl-benzamide; compound with 2,2,2-trifluoro-acetic acid Mp [° C.]: 259-275° C.

61. 4-Aminomethyl-N-(4-{5-[4-(1-methyl-1H-pyrazol-4-yl)-phenyl]-pyrazolo[1,5-c]pyrimidin-7-ylamino}-phenyl)-benzamide; compound with 2,2,2-trifluoro-acetic acid Mp [° C.]: 200

62. 4-Aminomethyl-N-[4-(5-benzo[1,3]dioxol-4-yl-pyrazolo[1,5-c]pyrimidin-7-ylamino)-phenyl]-benzamide; compound with 2,2,2-trifluoro-acetic acid Mp [° C.]: 245-247

63. 1,2,3,4-Tetrahydro-isoquinoline-6-carboxylic acid [3-(5-dibenzofuran-4-yl-pyrazolo[1,5-c]pyrimidin-7-ylamino)-phenyl]-amide; compound with 2,2,2-trifluoro-acetic acid Mp[° C.]: 109-113

64. N-[4-(5-Dibenzofuran-4-yl-pyrazolo[1,5-c]pyrimidin-7-ylamino)-phenyl]-4-[(2-methanesulfonyl-ethylamino)-methyl]-benzamide; compound with 2,2,2-trifluoro-acetic acid Mp [° C.]: 230-233

65. 5-Aminomethyl-pyridine-2-carboxylic acid [4-(5-dibenzofuran-4-yl-pyrazolo[1,5-c]pyrimidin-7-ylamino)-phenyl]-amide; compound with 2,2,2-trifluoro-acetic acid Mp [° C.]: 187-189 decomposition 66. 1,2,3,4-Tetrahydro-isoquinoline-6-carboxylic acid [4-(5-benzo[1,3]dioxol-4-yl-pyrazolo[1,5-c]pyrimidin-7-ylamino)-phenyl]-amide Mp [° C.]: 125-145

67. 4-Aminomethyl-N-{4-[5-(4'-fluoro-biphenyl-4-yl)-pyrazolo[1,5-c]pyrimidin-7-ylamino]-phenyl}-benzamide; compound with 2,2,2-trifluoro-acetic acid Mp [° C.]: 230-242

68. 4-Aminomethyl-N-{4-[5-(4-iodo-phenyl)-pyrazolo[1,5-c]pyrimidin-7-ylamino]-phenyl}-benzamide; compound with 2,2,2-trifluoro-acetic acid Mp [° C.]: 241-246

69. 4-Aminomethyl-N-{4-[5-(2'-fluoro-biphenyl-4-yl)-pyrazolo[1,5-c]pyrimidin-7-ylamino]-phenyl}-benzamide; compound with 2,2,2-trifluoro-acetic acid Mp [° C.]: 223-228

70. 4-Aminomethyl-N-{4-[5-(3'-fluoro-biphenyl-4-yl)-pyrazolo[1,5-c]pyrimidin-7-ylamino]-phenyl}-benzamide; compound with 2,2,2-trifluoro-acetic acid Mp [° C.]: 237-242

71. 4-Aminomethyl-N-[4-(5-biphenyl-3-yl-pyrazolo[1,5-c]pyrimidin-7-ylamino)-phenyl]-benzamide; compound with 2,2,2-trifluoro-acetic acid Mp [° C.]: 232-237

72. 4-Aminomethyl-N-{4-[5-(4'-methoxy-biphenyl-3-yl)-pyrazolo[1,5-c]pyrimidin-7-ylamino]-phenyl}-benzamide; compound with 2,2,2-triflouro-acetic acid A mixture of (4-{4-[5-(4'-methoxy-biphenyl-3-yl)-pyrazolo[1,5-c]pyrimidin-7-ylamino]-phenylcarbamoyl}-benzyl)-carbamic acid tertbutyl ester (0.124 g) and trifluoroacetic acid (TFA)(1.5 ml) in dichloromethane (7 ml) is stirred 3 h at ambient temperature. The reaction mixture is evaporated, coevaporated with toluene and dried at high vacuum. Crystals (0.136 g) are obtained in quantitative yield and a melting temperature at 235-240° C.

Starting from the appropriate starting compounds, which are mentioned or described explicitly below, or which can be prepared in a manner known to the person skilled in the art or analogously or similarly to the examples described by way of example herein, the following and also further relevant, non explicitly described analogous compounds can be obtained according to the procedure as in Example 72 or analogously or similarly thereto, or according to any procedure customary per se to the skilled person and/or described herein.

73. N-{4-[5-(3'-Acetylamino-biphenyl-3-yl)-pyrazolo[1,5-c]pyrimidin-7-ylamino]-phenyl}-4-aminomethyl-benzamide; compound with 2,2,2-trifluoro-acetic acid Mp [° C.]: 110-120

74. 4-Aminomethyl-N-{4-[5-(3'-methoxy-biphenyl-3-yl)-pyrazolo[1,5-c]pyrimidin-7-ylamino]-phenyl}-benzamide; compound with 2,2,2-trifluoro-acetic acid Mp [° C.]: 206-212

75. 4-(2-Amino-ethyl)-N-{4-[5-(4'-fluoro-biphenyl-4-yl)-pyrazolo[1,5-c]pyrimidin-7-ylamino]- phenyl}-benzamide; compound with 2,2,2-trifluoro-acetic acid Mp [° C.]: 208-215

76. 1,2,3,4-Tetrahydro-isoquinoline-6-carboxylic acid {4-[5-(4'-fluoro-biphenyl-4-yl)-pyrazolo[1,5-c]pyrimidin-7-ylamino]-phenyl}amide; compound with 2,2,2-trifluoro-acetic acid Mp [° C.]: 235-240

77. 1,2,3,4-Tetrahydro-isoquinoline-6-carboxylic acid {4-[5-(3'-methoxy-biphenyl-4-yl)-pyrazolo[1,5-c]pyrimidin-7-ylamino]-phenyl}amide; compound with 2,2,2-trifluoro-acetic acid MS: calc.: C, 35 H, 30 N, 6 O, 2 (566,7) fnd.: [M+1]: 567.4

78. 4-(2-Amino-ethyl)-N-{4-[5-(3'-methoxy-biphenyl-4-yl)-pyrazolo[1,5-c]pyrimidin-7-ylamino]-phenyl}-benzamide; compound with 2,2,2-trifluoro-acetic acid MS: calc,: C, 34 H, 30 N, 6 O, 2 (554.7) fnd. [M+1]: 555.4

79. 4-Aminomethyl-N-{4-[5-(2-methyl-benzofuran-7-yl)-pyrazolo[1,5-c]pyrimidin-7-ylamino]-phenyl}-benzamide; compound with 2,2,2trifluoro-acetic acid Mp [° C.]: 230-233

80. 1,2,3,4-Tetrahydro-isoquinoline-6-carboxylic acid {4-[5-(3'-nitro-biphenyl-4-yl)-pyrazolo[1,5-c]pyrimidin-7-ylamino]-phenyl}-amide; hydrochloride A mixture of 6-{4-[5-(3'-nitro-biphenyl-4-yl)-pyrazolo[1,5-c]pyrimidin-7-ylamino]-phenylcarbamoyl}3,4-dihydro-1H-isoquinoline-2-carboxylic acid tert-butyl ester (0.09 g) and 4M HCl in dioxane (10 ml) is stirred overnight at ambient temperature. The precipitated cristals are exhausted and washed with dioxane and diisopropylether. The product is dried at high vacuum. Crystals (0.07 g) are obtained in quantitative yield with a melting temperature at 280-283° C.

Starting from the appropriate staring compounds, which are mentioned or described explicitly below, or which can be prepared in a manner known to the person skilled in the art or analogously or similarly to the examples described by way of example herein, the following and also further relevant, non-explicitly described analogous compounds can be obtained according to the procedure as in Example 80 or analogously or similarly thereto, or according to any procedure customary per se to the skilled person and/or described herein.

81. 4-(2-Amino-ethyl)-N-{4-[5-(3'-nitro-biphenyl-4yl)-pyrazolo[1,5-c]pyrimidin-7-ylamino]-phenyl}-benzamide; hydrochloride Mp [° C.]: 295-299

82. N-{4-[5-(3'-Acetylamino-biphenyl-4-yl)-pyrazolo[1,5-c]pyrimidin-7-ylamino]-phenyl}-4-(2-amino-ethyl)-benzamide; hydrochloride Mp [° C.]: 205-210

83. 1,2,3,4-Tetrahydro-isoquinoline-6-carboxylic acid {4-[5-(3'-acetylamino-biphenyl-4-yl)-pyrazolo[1,5-c]pyrimidin-7-ylamino]-phenyl}-amide; hydrochloride Mp [° C.]: 218-222

84. 4-(2-Amino-ethyl)-N-{4-[5-(4-bromo-phenyl)-pyrazolo[1,5-c]pyrimidin-7-ylamino]-phenyl}-benzamide; hydrochloride Mp [° C.]: 307-310

85. 1,2,3,4-Tetrahydro-isoquinoline-6-carboxylic acid {4-[5-(4-bromo-phenyl)-pyrazolo[1,5-c]pyrimidin-7-ylamino]-phenyl}-amide; hydrochloride Mp [° C.]: 254-260

86. 4-(2-Amino-ethyl)-N-{4-[3-bromo-5-(3'-methoxy-biphenyl-4-yl)-pyrazolo[1,5-]pyrimidin-7-ylamino]-phenyl}-benzamide; hydrochloride Mp [° C.]: 265-268

87. 4-Aminomethyl-N-{4-[3-bromo-5-(3'-methoxy-biphenyl-4-yl)-pyrazolo[1,5-c]pyrimidin-7-ylamino]-phenyl}-benzamide; hydrochloride Mp [° C.]: 272-276

88. 4-Aminomethyl-N-{4-[3-bromo-5-(4'-methoxy-biphenyl-4-yl)-pyrazolo[1,5-c]pyrimidin-7-ylamino]-phenyl}-benzamide; hydrochloride Mp [° C.]: 272-275

89. 4-Aminomethyl-N-{4-[3-bromo-5-(4'-fluoro-biphenyl-4-yl)-pyrazolo[1,5-c]pyrimidin-7-ylamino]-phenyl}-benzamide; hydrochloride Mp [° C.]: 269-272

90. N-{4-[5-(3'-Acetylamino-biphenyl-4-yl)-3-bromo-pyrazolo[1,5-c]pyrimidin-7-ylamino]-phenyl}-4-aminomethyl-benzamide; hydrochloride Mp [° C.]: 259-262

91. 4-Aminomethyl-N-[4-(3-bromo-5-dibenzofuran-4-yl-pyrazolo[1,5-c]pyrimidin-7-ylamino) -phenyl]-benzamide; hydrochloride Mp [° C.]: 282-278

Starting Compounds

A1. {4-[4-(5-Biphenyl-4-yl-pyrazolo[1,5-c]pyrimidin-7-ylamino)-phenylcarbamoyl]benzyl}-carbamic acid tert-butyl ester Under an inert gas atmosphere at 130° C. bath temperature is heated neat a mixture of 5-biphenyl-4-yl-7-methanesulfonyl-pyrazolo[1,5-c]pyrimidine (compound B1) and [4-(4-amino-phenylcarbamoyl)-benzyl]-carbamic acid tert-butyl ester (compound G1) overnight. The crude product is purified by silica gel flash chromatography.

In a similar way can be prepared:
(4-{4-[5-(6-Phenyl-pyridin-3-yl)-pyrazolo[1,5-c]pyrimidin-7-ylamino]-phenylcarbamoyl}-benzyl)-carbamic acid tert-butyl ester,
(4-{4-[5-(4'-Methoxy-biphenyl-4-yl)-pyrazolo[1,5-c]pyrimidin-7-ylamino]-phenylcarbamoyl}-benzyl)-carbamic acid tert-butyl ester,
(4-{4-[5-(2'-Methoxy-biphenyl-4-yl)-pyrazolo[1,5-c]pyrimidin-7-ylamino]-phenylcarbamoyl}-benzyl)-carbamic acid tert-butyl ester.

A2. (4-{4-[5-(6-Benzyloxy-naphthalen-2-yl)-pyrazolo[1,5-c]pyrimidin-7-ylamino]-phenylcarbamoyl}-benzyl)-carbamic acid tert-butyl ester To a solution of 4-(tert-butoxycarbonylamino-methyl)-benzoic acid (251 mg) and N-hydroxy-benzotriazole (HOBt) (153 mg) in DMF (10 ml) are added 1-ethyl-3-(3-dimethylaminopropyl)carbodiimide hydrochloride (EDC)(575 mg) and triethylamine (0.416 ml). The mixture is stirred for 0.5 h at ambient temperature. To this solution is added N-[5-(6-benzyloxy-naphthalen-2-yl)-pyrazolo[1,5-c]pyrimidin-7-yl]-benzene-1,4-diamine (compound B2)(0.38 g). After completion of the reaction the mixture is evaporated at high vacuum and the residue is treated with methanol. The resulting solid is filtered and dried. A colorless solid (0.523 g) is obtained in 91% yield.

In a similar way can be obtained:
6-[4-(5-Dibenzofuran-4-yl-pyrazolo[1,5-c]pyrimidin-7-ylamino)-phenylcarbamoyl]-3,4-dihydro-1H-isoquinoline-2-carboxylic acid tert-butyl ester,
{4-[4-(5-Dibenzofuran-4-yl-pyrazolo[1,5-c]pyrimidin-7-ylamino)-phenylcarbamoyl]-benzyl}-[2-(tetrahydro-pyran-2-yloxy)-ethyl]-carbamic acid dimethyl-ethyl ester,
{2-[4-(5-Dibenzofuran-4-yl-pyrazolo[1,5-c]pyrimidin-7-ylamino)-phenylcarbamoyl]-pyridin-4-ylmethyl}-carbamic acid tert-butyl ester,
[3-[4-(5-Dibenzofuran-4-yl-pyrazolo[1,5-c]pyrimidin-7-ylamino)-phenylcarbamoyl]-3-(3,4-dichloro-phenyl)-propyl]-carbamic acid tert-butyl ester,
[2-[3-(5-Dibenzofuran-4-yl-pyrazolo[1,5-c]pyrimidin-7-ylamino)-phenylcarbamoyl]-2-(3,4-dichloro-phenyl)-ethyl]-carbamic acid tert-butyl ester,
(1-{4-[3-(5-Dibenzofuran-4-yl-pyrazolo[1,5-c]pyrimidin-7-ylamino)-phenylcarbamoyl]-phenyl}-1-methyl-ethyl)-carbamic acid tert-butyl ester,
{5-[4-(5-Dibenzofuran-4-yl-pyrazolo[1,5-c]pyrimidin-7-ylamino)-phenylcarbamoyl]-furan-2-ylmethyl}-carbamic acid tert-butyl ester, A3. (4-{4-[5-(6-Hydroxy-naphthalen-2-yl)-pyrazolo[1,5-c]pyrimidin-7-ylamino]-phenylcarbamoyl}-benzyl)-carbamic acid tert-butyl ester A mixture of (4-{4-[5-(6-benzyloxy-naphthalen-2-yl)-pyrazolo[1,5-c]pyrimidin-7-ylamino]-phenylcarbamoyl}-benzyl)-carbamic acid tert-butyl ester (compound A2)(750 mg) and Pd/C (10%, 100 mg) in dioxane (100 ml) is hydrogenated (1.1 bar) at 80° C. for 3 days. The reaction mixture is filtered and the filtrate is evaporated. After silica gel flash chromatography the product is obtained as colorless solid in 48% yield.

A4. [4-(4-{5-[6-(2-Methoxy-ethoxy)-naphthalen-2-yl]-pyrazolo[1,5-c]pyrimidin-7-ylamino}-phenylcarbamoyl)-benzyl]-carbamic acid tert-butyl ester To a solution of (4-{4-[5-(6-hydroxy-naphthalen-2-yl)-pyrazolo[1,5-c]pyrimidin-7-ylamino]-phenylcarbamoyl}-benzyl)-carbamic acid tert-butyl ester (compound A3)(120 mg) in DMF (3 ml) are added NaH (8 mg) and 2-bromoethylmethylether (0.019 ml). The mixture is stirred overnight and after extraction the crude product is purified by silica gel flash chromatography. A nearly colorless solid (68 mg) in 52% yield is obtained.

In a similar way can be obtained:
{4-[4-(5-{6-[2-(Tetrahydro-pyran-2-yloxy)-ethoxy]-naphthalen-2-yl}-pyrazolo[1,5-c]pyrimidin-7-ylamino)-phenylcarbamoyl]-benzyl}-carbamic acid tert-butyl ester
(6-{7-[4-({1-[4-(tert-Butoxycarbonylamino-methyl)-phenyl]-methanoyl}-amino)-phenylamino]-pyrazolo[1,5-c]pyrimidin-5-yl}-naphthalen-2-yloxy)-acetic acid tert-butyl ester A5. (4-{4-[5-(4'-Methoxy-biphenyl-3-yl)-pyrazolo[1,5-c]pyrimidin-7-ylamino]-phenylcarbamoyl}-benzyl)-carbamic acid tert-butyl ester Under an inert gas atmosphere at 130° C. bath temperature is heated neat a mixture of 7-methanesulfonyl-5-(4'-methoxy-biphenyl-3-yl)-pyrazolo[1,5-c]pyrimidine and [4-(4-amino-phenylcarbamoyl)-benzyl]-carbamic acid tertbutyl ester (compound B3) overnight. The crude product is purified by silica gel flash chromatography.

In a similar way can be prepared:
(4-{4-[5-(3'-Acetylamino-biphenyl-3-yl)-pyrazolo[1,5-c]pyrimidin-7-ylamino]-phenylcarbamoyl}-benzyl)-carbamic acid tertbutyl ester
(4-{4-[5-(3'-Methoxy-biphenyl-3-yl)-pyrazolo[1,5-c]pyrimidin-7-ylamino]-phenylcarbamoyl}-benzyl)-carbamic acid tertbutyl ester
(4-{4-[5-(4'-Methoxy-biphenyl-3-yl)-pyrazolo[1,5-c]pyrimidin-7-ylamino]-phenylcarbamoyl}benzyl)-carbamic acid tert-butyl ester
(4-{4-[5-(2-Methylbenzofuran-7-yl)-pyrazolo[1,5-c]pyrimidin-7-ylamino]-phenylcarbamoyl}-benzyl)-carbamic acid tert-butyl ester
(4-{4-[3-Bromo-5-(4'-methoxy-biphenyl-4-yl)-pyrazolo[1,5-c]pyrimidin-7-ylamino]-phenylcarbamoyl}-benzyl)-carbamic acid tertbutyl ester
(4-{4-[5-(3'-Acetylamino-biphenyl-4-yl)-3-bromo-pyrazolo[1,5-c]pyrimidin-7-ylamino]-phenylcarbamoyl}-benzyl)-carbamic acid tertbutyl ester
{4-[4-(3-Bromo-5-dibenzofuran-4-yl-pyrazolo[1,5-c]pyrimidin-7-ylamino)-phenylcarbamoyl]-benzyl}-carbamic acid tert-butyl ester

A6. [2-(4-{4-[5-(4'-Fluoro-biphenyl-4-yl)-pyrazolo [1,5-c]pyrimidin-7-ylamino]-phenylcarbamoyl}-phenyl)-ethyl]-carbamic acid tert-butyl ester To a solution of 4-(tert-butoxycarbonylamino-ethyl)-benzoic acid (78 mg) and N-hydroxy-benzotriazole (HOBt)(45 mg) in DMF (5 ml) are added 1-ethyl-3-(3-dimethylaminopropyl)carbodiimide hydrochloride (EDC)(150 mg) and triethylamine (0.27 ml). The mixture is stirred for 0.5 h at ambient temperature. To this solution is added N-[5-(4'-Fluoro-biphenyl-4-yl)-pyrazolo[1,5-c]pyrimidin-7-yl]-benzene-1,4-diamine (compound B4)(0.1 g). After completion of the reaction the mixture is evaporated at high vacuum and the residue is treated with methanol. The resulting solid is filtered and dried. A yellow solid (0.097 g) is obtained.

In a similar way can be obtained:
6-{4-[5-(4'-Fluoro-biphenyl-4-yl)-pyrazolo[1,5-c]pyrimidin-7-ylamino]-phenylcarbamoyl}-3,4-dihydro-1H-isoquinoline-2-carboxylic acid tertbutyl ester
6-{4-[5-(3'-Methoxy-biphenyl-4-yl)-pyrazolo[1,5-c]pyrimidin-7-ylamino]-phenylcarbamoyl}-3,4-dihydro-1H-isoquinoline-2-carboxylic acid tertbutyl ester
[2-(4-{4-[5-(3'-Methoxy-biphenyl-4-yl)-pyrazolo[1,5-c]pyrimidin-7-ylamino]-phenylcarbamoyl}-phenyl)-ethyl]-carbamic acid tertbutyl ester
6-{4-[5-(3'-Nitro-biphenyl-4-yl)-pyrazolo[1,5-c]pyrimidin-7-ylamino]-phenylcarbamoyl}3,4-dihydro-1H-isoquinoline-2-carboxylic acid tertbutyl ester
[2-(4-{4-[5-(3'-Nitro-biphenyl-4-yl)-pyrazolo[1,5-c]pyrimidin-7-ylamino]-phenylcarbamoyl}-phenyl)-ethyl]carbamic acid tertbutyl ester
[2-(4-{4-[5-(3'-Acetylamino-biphenyl-4-yl)-pyrazolo[1,5-c]pyrimidin-7-ylamino]-phenylcarbamoyl}-phenyl)-ethyl]-carbamic acid tertbutyl ester
6-{4-[5-(3'-Acetylamino-biphenyl-4-yl)-pyrazolo[1,5-c]pyrimidin-7-ylamino]-phenylcarbamoyl}-3,4-dihydro-1H-isoquinoline-2-carboxylic acid tertbutyl ester
[2-(4-{4-[5-(4-Bromo-phenyl)-pyrazolo[1,5-c]pyrimidin-7-ylamino]-phenylcarbamoyl}-phenyl)-ethyl]-carbamic acid tertbutyl ester
6-{4-[5-(4-Bromo-phenyl)-pyrazolo[1,5-c]pyrimidin-7-ylamino]-phenylcarbamoyl}-3,4-dihydro-1H-isoquinoline-2-carboxylic acid tertbutyl ester
[2-(4-{4-[3-Bromo-5-(3'-methoxy-biphenyl-4-yl)-pyrazolo[1,5-c]pyrimidin-7-ylamino]-phenylcarbamoyl}-phenyl)-ethyl]-carbamic acid tert-butyl ester
(4-{4-[3-Bromo-5-(3'-methoxy-biphenyl-4-yl)-pyrazolo[1,5-c]pyrimidin-7-ylamino]-phenylcarbamoyl}-benzyl)-carbamic acid tert-butyl ester
(4-{4-[3-Bromo-5-(4'-fluoro-biphenyl-4-yl)-pyrazolo[1,5-c]pyrimidin-7-ylamino]-phenylcarbamoyl}-benzyl)-carbamic acid tert-butyl ester

B1. 5-Biphenyl-4-yl-7-methanesulfonyl-pyrazolo[1,5-c]pyrimidine

To a solution of 5-biphenyl-4-yl-7-methylsulfanyl-pyrazolo[1,5-c]pyrimidine (compound C1)(0.3 g) in dichloromethane (40 ml) at 0° C. is added m-chloroperbenzoic acid (0.7 g). The mixture is stirred at ambient temperature overnight and subsequently extracted with aqueous 5% sodium bicarbonate solution and the crude product is purified by silica gel flash chromatography. A colorless solid (0.23 g) is obtained in 70% yield.

In a similar way can be prepared:
5-Dibenzofuran-4-yl-7-methanesulfonyl-pyrazolo[1,5-c]pyrimidine,
7-Methylsulfonyl-5-(6-phenyl-pyridin-3-yl)-pyrazolo[1,5-c]pyrimidine,
5-(6-Benzyloxy-naphthalen-2-yl)-7-methanesulfonyl-pyrazolo[1,5-c]pyrimidine,
5-(2'-Methoxy-biphenyl-4-yl)-7-methanesulfonyl-pyrazolo[1,5-c]pyrimidine,
5-(4'-Methoxy-biphenyl-4-yl)-7-methanesulfonyl-pyrazolo[1,5-c]pyrimidine,
5-Biphenyl-3-yl-7-methylsulfonyl-pyrazolo[1,5-c]pyrimidine.

B2. N-[5-(6-Benzyloxy-naphthalen-2-yl)-pyrazolo[1,5-c]pyrimidin-7-yl]-benzene-1,4-diamine A mixture of {4-[5-(6-benzyloxy-naphthalen-2-yl)-pyrazolo[1,5-c]pyrimidin-7-ylamino]-phenyl}-carbamic acid tert-butyl ester (compound C2)(450 mg), TFA (2 ml) and dichloromethane (10 ml) is stirred 4 h at ambient temperature. The reaction mixture is evaporated and coevaporated with toluene. The residue is partitioned between a aqueous saturated solution of sodium bicarbonate and ethyl acetate. After drying the organic phase is evaporated and the residue is dried in vacuum. A solid in quantitative yield is obtained.

In a similar way can be are obtained:
[4-(5-Biphenyl-3-yl-pyrazolo[1,5-c]pyrimidin-7-yl]-benzene-1,4-diamine
[4-(5-Dibenzofuran-4-yl-pyrazolo[1,5-c]pyrimidin-7-yl]-benzene-1,4-diamine
[3-(5-Dibenzofuran-4-yl-pyrazolo[1,5-c]pyrimidin-7-yl]-benzene-1,3-diamine

B3. 7-Methanesulfonyl-5-(4'-methoxy-biphenyl-3-yl)-pyrazolo[1,5-c]pyrimidine To a solution of 5-(4'-methoxy-biphenyl-3-y)-7-methylsulfanyl-pyrazolo[1,5-c]pyrimidine (compound C3)(04.1 g) in dichloromethane (40 ml) at 0° C. is added m-chloroperbenzoic acid (0.6 g). The mixture is stirred at ambient temperature overnight and subsequently extracted with aqueous 5% sodium bicarbonate solution and the crude product is purified by silica gel flash chromatography. A colorless solid (0.22 g) is obtained in 50% yield.

In a similar way can be prepared:
N-[3'-(7-Methanesulfonyl-pyrazolo[1,5-c]pyrimidin-5-yl)-biphenyl-3-yl]-acetamide
7-Methanesulfonyl-5-(3-methoxy-biphenyl-3-yl)-pyrazolo[1,5-c]pyrimidine
5-(4'-Fluoro-biphenyl-4-yl)-7-methanesulfonyl-pyrazolo[1,5-c]pyrimidine
7-Methanesulfonyl-5-(3'-methoxy-biphenyl-4-yl)-pyrazolo[1,5-c]pyrimidine
7-Methanesulfonyl-5-(3'-nitro-biphenyl-4-yl)-pyrazolo[1,5-c]pyrimidine
N-[4'-(7-Methanesulfonyl-pyrazolo[1,5-c]pyrimidin-5-yl)-biphenyl-3-yl]-acetamide
5-(4-Bromo-phenyl)-7-methanesulfonyl-pyrazolo[1,5-c]pyrimidine
5-(3-Bromo-phenyl)-7-methanesulfonyl-pyrazolo[1,5-c]pyrimidine
7-Methanesulfonyl-5-(2-methyl-benzofuran-7-yl)-pyrazolo[1,5-c]pyrimidine
3-Bromo-7-methanesulfonyl-5-(3'-methoxy-biphenyl-4-yl)-pyrazolo[1,5-c]pyrimidine
3-Bromo-7-methanesulfonyl-5-(4'-methoxy-biphenyl-4-yl)-pyrazolo[1,5-c]pyrimidine
3-Bromo-5-(4'-fluoro-biphenyl-4-yl)-7-methanesulfonyl-pyrazolo[1,5-c]pyrimidine N[4'-(3-Bromo-7-methanesulfonyl-pyrazolo[1,5-c]pyrimidin-5-yl)-biphenyl-3-yl]-acetamide
3-Bromo-5-dibenzofuran-4-yl-7-methanesulfonyl-pyrazolo[1,5-c]pyrimidine

B4. N-[5-(4'-Fluoro-biphenyl-4-yl)-pyrazole[1,5-c]pyrimidin-7-yl]-benzene-1,4-diamine A mixture of {4-[5-(4-fluoro-biphenyl-4-yl)-pyrazolo[1,5-c]pyrimidin-7-ylamino]-phenyl}-carbamic acid tert-butyl ester (compound C4)(400 mg), TFA (4 ml) and dichloromethane (20 ml) is stirred 4 h at ambient temperature. The reaction mixture is evaporated and coevaporated with toluene. The residue is dried in vacuum. A grey solid (435 mg) in quantitative yield is obtained.

In a similar way can be are obtained:
N-[5-(3'-Methoxy-biphenyl-4-yl)-pyrazolo[1,5-c]pyrimidin-7-yl]-benzene-1,4-diamine
N-[5-(3'-Nitro-biphenyl-4-yl)-pyrazolo[1,5-c]pyrimidin-7-yl]-benzene-1,4-diamine
N-{4'-[7-(4-Amino-phenylamino)-pyrazolo[1,5-c]pyrimidin-5-yl]-biphenyl-3-yl}-acetamide
N-[5-(4-Bromo-phenyl)-pyrazolo[1,5-c]pyrimidin-7-yl]-benzene-1,4-diamine
N-[3-Bromo-5-(3'-methoxy-biphenyl-4-yl)-pyrazolo-[1,5-c]-pyrimidin-7-yl]-benzene-1,4-diamine

C1. 5-Biphenyl-4-yl-7-methylsulfanyl-pyrazolo[1,5-c]pyrimidine

Under an inert gas atmosphere is dissolved 5-(4-iodo-phenyl)-7-methylsulfanyl-pyrazolo[1,5-c]pyrimidine (compound D1)(0.45 g) and phenylboronic acid (0.35 g) in dimethoxyethane. To this solution are added bis-(triphenylphosphine)-palladium(II) chloride (0.19 mmol) and an aqueous sodium carbonate solution (2M, 6 ml). The reaction mixture is heated to reflux for 4.5 h. After 1 h further phenylboronic acid (0.2 g) is added in order to complete the reaction. The mixture is diluted with ethyl acetate and filtered over silica gel. The product is partitioned between ethyl acetate and an aqueous solution of sodium bicarbonate (5%), the organic phase is dried over sodium sulfate and the crude product is purified by silica gel flash chromatography. A nearly colorless solid (0.3 g) in 50% yield is obtained.

In a similar way can be prepared:
7-Methylsulfanyl-5-(6-phenyl-pyridin-3-yl)-pyrazolo[1,5-c]pyrimidine,
5-(2'-Methoxy-biphenyl-4-yl)-7-methanesulfonyl-pyrazolo[1,5-c]pyrimidine,
5-(4'-Methoxy-biphenyl-4-yl)-7-methanesulfonyl-pyrazolo[1,5-c]pyrimidine,
5-Biphenyl-3-yl-7-methylsulfanyl-pyrazolo[1,5-c]pyrimidine.

C2. {4-[5-(6-Benzyloxy-naphthalen-2-yl)-pyrazolo[1,5-c]pyrimidin-7-ylamino]-phenyl}-carbamic acid tert-butyl ester A mixture of 5-(6-benzyloxy-naphthalen-2-yl)-7-methanesulfonyl-pyrazolo[1,5-c]pyrimidine (compound D2)(87 mg) and 4-amino-phenyl-carbamic acid tert-butyl ester (208 mg) is heated neat at 130 to 140° C. bath temperature for 20 min. After cooling, the crude product is purified by silica gel flash chromatography. A nearly colorless solid (51 mg, 46%) with melting temperature of 189° C. is obtained.

In a similar way can be obtained:
[4-(5-Biphenyl-3-yl-pyrazolo[1,5-c]pyrimidin-7-ylamino)-phenyl]-carbamic acid tert-butyl ester
[4-(5-Dibenzofuran-4-yl-pyrazolo[1,5-c]pyrimidin-7-ylamino)-phenyl]-carbamic acid tert-butyl ester
[3-(5-Dibenzofuran-4-yl-pyrazolo[1,5-c]pyrimidin-7-ylamino)-phenyl]-carbamic acid tert-butyl ester

C3. 5-(4'Methoxy-biphenyl-3-yl)-7-methylsulfanyl-pyrazolo[1,5-c]pyrimidine

Under an inert gas atmosphere is dissolved 5-(3bromophenyl)-7-methylsulfanyl-pyrazolo-[1,5-c]pyrimidine (compound D3)(0.25 g) and 4-methoxyphenyl boronic acid (0.45 g) in dimethoxyethane. To this solution are added bis-(triphenylphosphine)palladium(II) chloride (0.13 mmol) and an aqueous sodium carbonate solution (2M, 8 ml). The reaction mixture is heated to reflux for 18 h The mixture is diluted with ethyl acetate and filtered over silica gel. The product is partitioned between ethyl acetate and an aqueous solution of sodium bicarbonate (5%), the organic phase is dned over sodium sulfate and the crude product is purified by silica gel flash chromatography. A nearly colorless solid (0.41 g) in 60% yield is obtained, In a similar way can be prepared:
N-[3'-(7-Methylsulfanyl-pyrazolo[1,5-c]pyrimidin-5-yl)-biphenyl-3-yl]-acetamide
5-(3'-Methoxy-biphenyl-3-yl)-7-methylsulfanyl-pyrazolo[1,5-c]pyrimidine
5-(4'-Fluoro-biphenyl-4-yl)-7-methylsulfanyl-pyrazolo[1,5-c]pyrimidine
5-(3'-Methoxy-biphenyl-4-yl)-7-methylsulfanyl-pyrazolo[1,5-c]pyrimidine
7-Methylsulfanyl-5-(3'-nitro-biphenyl-4-yl)-pyrazolo[1,5-c]pyrimidine
N-[4'-(7-Methylsulfanyl-pyrazolo[1,5-c]pyrimidin-5-yl)-biphenyl-3-yl]-acetamide
3-Bromo-5-(3'-methoxy-biphenyl-4-yl)-7-methylsulfanyl-pyrazolo[1,5-c]pyrimidine
3-Bromo-5-(4'-methoxy-biphenyl-4-yl)-7-methylsulfanyl-pyrazolo[1,5-c]pyrimidine
3-Bromo-5-(4'-fluoro-biphenyl-4-yl)-7-metlhylsulfanyl-pyrazolo[1,5-c]pyrimidine
N-[4'-(3-Bromo-7-methylsulfanyl-pyrazolo[1,5-c]pyrimidin-5-yl)-biphenyl-3-yl]acetamide

C4. {4-[5-(4'-Fluoro-biphenyl-4-yl)-pyrazolo[1,5-c]pyrimidin-7-ylamino]-phenyl}-carbamic acid tert-butyl ester A mixture of 5-(4'-fluoro-biphenyl-4-yl)-7-methanesulfonyl-pyrazolo[1,5-c]pyrimidine (700 mg) and 4 amino-phenyl-carbamic acid tert-butyl ester (1200 mg) is heated neat at 130 to 140° C. bath temperature for 20 min. After cooling, the crude product is purified by silica gel flash chromatography. A bright yellow solid (400 mg) in 42% yield is obtained.

In a similar way can be obtained
{4-[5-(3'-Methoxy-biphenyl-4-yl)-pyrazolo[1,5-c]pyrimidin-7-ylamino]-phenyl}-carbamic acid tert-butyl ester
{4-[5-(3'-Nitro-biphenyl-4-yl)-pyrazolo[1,5-c]pyrimidin-7-ylamino]-phenyl}-carbamic acid tertbutyl ester
{4-[5-(3'-Acetylamino-biphenyl-4-yl)-pyrazolo[1,5-c]pyrimidin-7-ylamino]-phenyl}-carbamic acid tert-butyl ester
{4-[5-(4-Bromo-phenyl)-pyrazolo[1,5-c]pyrimidin-7-ylamino]-phenyl}-carbamic acid tertbutyl ester
{4-[3-Bromo-5-(3'-methoxy-biphenyl-4-yl)-pyrazolo[1,5-c]pyrimidin-7-ylamino]-phenyl}-carbamic acid tert-butyl ester

D1. 5-(4-Iodo-phenyl)-7-methylsulfanyl-pyrazolo[1,5-c]pyrimidine

To a solution of 5-(4-iodo-phenyl)-6H-pyrazolo[1,5-c]pyrimidine-7-thione (compound E1)(2.09 g) in 2M aqueous NaOH (3 ml) and methanol (40 ml), methyl iodide (0.376 ml) is added at ambient temperature. After 30 min at this temperature further methyl iodide (0.376 ml) is added. After 60 min the mixture is neutralized with 2M hydrochloric acid and evaporated. The residue is partitioned between dichloromethane and water and the organic phase is washed twice with water. The organic phase is dried over sodium sulfate and the crude product is purified by silica gel flash chromatography. A nearly colorless solid (1.35 g, 62%) is obtained.

In a similar way can be prepared:
5-Dibenzofuran-4-yl-7-methylsulfanyl-pyrazolo[1,5-c]pyrimidine,
5-(6-Chloro-pyridin-3-yl)-7-methylsulfanyl-pyrazolo[1,5-c]pyrimidine,
5-(6-Benzyloxy-naphthalen-2-yl)-7-methylsulfanyl-pyrazolo[1,5-c]pyrimidine,
5-(3-Bromo-phenyl)-7-methylsulfanyl-pyrazolo[1,5-c]pyrimidine.

D2. 5-(6-Benzyloxy-naphthalen-2-yl)-7-methanesulfonyl-pyrazolo[1,5-c]pyrimidine The title compound can be obtained from 5-(6-benzyloxy-naphthalen-2-yl)-7-methylsulfanyl-pyrazolo[1,5-c]pyrimidine (compound E2) analogously as described for compound B1.

D3. 5-(3-Bromo-phenyl)-7-methylsulfanyl-pyrazolo[1,5-c]pyrimidine

To a solution of 5-(3-bromo-phenyl)-6H-pyrazolo[1,5-c]pyrimidine-7-thione (compound E3)(3.73 g) in 2M aqueous NaOH (6 ml) and methanol (100 ml) methyl iodide (0.785 ml) is added at ambient temperature. After 30 min at this temperature further methyl iodide (0.785 ml) is added After 60 min the mixture is neutralized with 2M hydrochloric acid and evaporated The residue is partitioned between dichloromethane and water and the organic phase is washed twice with water. The organic phase is dried over sodium sulfate and the crude product is purified by silica gel flash chromatography. A yellow solid (1.4 g, 36%) is obtained In a similar way can be prepared:
5-(4-Iodo-phenyl)-7-metlhylsulfanyl-pyrazolo[1,5-c]pyrimidine
5-(4-Bromo-phenyl)-7-methylsulfanyl-pyrazolo[1,5-c]pyrimidine
5-(3-Bromo-phenyl)-7-methylsulfanyl-pyrazolo[1,5-c]pyrimidine
5-(2-Methyl-benzofuran-7-yl)-7-methylsulfanyl-pyrazolo[1,5-c]pyrimidine
5-Dibenzofuran-4-yl-7-methylsulfanyl-pyrazolo[1,5-c]pyrimidine

D4. 3-Bromo-5-(4-iodo-phenyl)-7-methylsulfanyl-pyrazolo[1,5-c]pyrimidine

To a solution of 5-(4-iodo-phenyl)-7-methylsulfanyl-pyrazolo[1,5-c]pyrimidin (1000 mg) in chlorobenzene N-bromosuccinimide (730 mg) is added. The mixture is stirred for 1 hour then the chlorobenzene is evaporated. The residue is partitioned between ethylacetate and sodium-hydrogencarbonate (5%). The organic phase is dried over sodium sulfate and the crude product is purified by silica gel flash chromatography. A nearly white solid (840 mg, 70%) is obtained.

In a similar way can be prepared:
3-Bromo-5-dibenzofuran-4-yl-7-methylsulfanyl-pyrazolo[1,5-c]pyrimidine

E1. 5-(4-Iodo-phenyl)-6H-pyrazolo[1,5-c]pyrimidine-7-thione

A mixture of 1-(4-iodo-phenyl)-5-methoxy-pent-4-ene-1,3-dione (compound F1)(1.9 g) and thiosemicarbazide (5 g) in methanol (220 ml) is heated to reflux temperature. After the reaction is completed the solid is filtered and washed with methanol. The filtrate with the product is purified by flash silica gel chromatography.

In a similar way can be prepared:
5-Dibenzofuran-4-yl-6H-pyrazolo[1,5-c]pyrimidine-7-thione,
5-(6-Chloro-pyridin-3-yl)-6H-pyrazolo[1,5-c]pyrimidine-7-thione,
5-(6-Benzyloxy-naphthalen-2-yl)-6H-pyrazolo[1,5-c]pyrimidine-7-thione,
5-(3-Bromo-phenyl)-6H-pyrazolo[1,5-c]pyrimidine-7-thione.

E2. 5-(6-Benzyloxy-naphthalen-2-yl)-7-methylsulfanyl-pyrazolo[1,5-c]pyrimidine The title compound can be obtained in an analogous synthesis rout as described to give compound D1.

E3. 5-(3-Bromo-phenyl)-6H-pyrazolo[1,5-c]pyrimidine-7-thione

A mixture of (E)-1-(3-bromo-phenyl)-5-methoxy-pent-4-ene-3-dione (compound F2)(crude product) and thiosemicarbazide (6 g) in methanol (500 ml) is heated to reflux temperature. After the reaction is completed the solid is filtered and washed with methanol. The filtrate with the product is purified by flash silica gel chromatography.

In a similar way can be prepared
5-(4-Iodo-phenyl)-6H-pyrazolo[1,5-c]pyrimidine-7-thione
5-(4-Bromo-phenyl)-6H-pyrazolo[1,5-c]pyrimidine-7-thione
5-3-(Bromo-phenyl)-6H-pyrazolo[1,5-c]pyrimidine-7-thione
5-(2-Methyl-benzofuran-7-yl)-6H-pyrazolo[1,5-c]-pyrimidine-7-thione
5-Dibenzofuran-4-yl-6H-pyrazolo[1,5-c]pyrimidine-7-thione

F1. 1-(4-Iodo-phenyl)-5-methoxy-pent-4-ene-1,3-dione

In a 1 ltr flask is cooled a solution of lithium hexamethyldisilazide (50 ml, 1.5 M) in THF (250 ml) to −75° C. During a period of 1 h is added 4-methoxy-but-3-en-2-one (6 ml). The mixture is stirred for 1 h at −70° C. A solution of 4-iodobenzoylchloride (7.2 g) in THF (250 ml) is added to the above mixture during 1 h at −70° C. The resulting mixture is slowly heated to ambient temperature and stirred for 1 h. Subsequently, the mixture is added to a cold aqueous solution of ammonium chloride and the resulting suspension is extracted with ethyl acetate. The organic phase is extracted twice with an aqueous solution of ammonium chloride, dried over sodium sulfate and evaporated. The crude oily product is transferred to the next step without any further purification.

In a similar way can be are prepared:
1-Dibenzofuran-4-yl-5-methoxy-pent-4-ene-1,3-dione,
1-(6-Chloro-pyridin-3-yl)-5-methoxy-pent-4-ene-1,3-dione,
1-(6-Benzyloxy-naphthalen-2-yl)-5-methoxy-pent-4-ene-1,3-dione,
1-(3-Bromo-phenyl)-5-methoxy-pent-4-ene-1,3-dione.

F2. (E)-1-(3-Bromo-phenyl)-5-methoxy-pent-4-ene-1,3-dione

In a 1 ltr flask is cooled a solution of lithium hexamethyldisilazide (65 ml, 1.5 M) in THF (250 ml) to 75 °C. During a period of 1 h is added 4-methoxy-but-3-en-2-one (7 ml). The mixture is stirred for 1 h at −70° C. A solution of 3-bromobenzoylchloride (6 g) in THF (250 ml) is added to the above mixture during 1 h at −70° C. The resulting mixture is slowly heated to ambient temperature and stirred for 1 h. Subsequently, the mixture is added to a cold aqueous solution of ammonium chloride and the resulting suspension is extracted with ethyl acetate. The organic phase is extracted twice with an aqueous solution of ammonium chloride, dried over sodium sulfate and evaporated. The crude oily product is transferred to the next step without any further purification.

In a similar way can be are prepared
(E)-1-(4-Iodo-phenyl)-5-methoxy-pent-4-ene-1,3-dione
(E)-1-(4-Bromo-phenyl)-5-methoxy-pent-4-ene-1,3-dione
(E)-5-Methoxy-1-(2-methyl-benzofuran-7-yl)-pent-4-ene-1,3-dione
(E)-1-(3-Bromo-phenyl)-5-methoxy-pent-4-ene-1,3-dione
(E)-1-Dibenzofuran-4-yl-5-methoxy-pent-4ene-1,3-done GI.
[4-(4-Amino-phenylcarbamoyl)-benzyl]-carbamic acid tert-butyl ester To a solution of 4-(tert-butoxycarbonylamino-methyl)-benzoic acid (1.005 g) and N-hydroxy-benzotriazole (HOBt) (0.642 g) in DMF (30 ml) are added 1-ethyl-3-(3-dimethylaminopropyl)carbodiimide hydrochloride (EDC)(2.76 g) and triethylamine (2.005 ml). The mixture is stirred for 1 h at ambient temperature. This solution is added at 0° C. slowly to a solution of 1,4-diaminobenzene (0.43 g) and triethylamine (0.45 ml) in DMF (5 ml). After completion of the chemical reaction the mixture is evaporated at high vacuum and the residue is partitioned between ethyl acetate and an aqueous saturated sodium bicarbonate solution. The organic phase is dried over sodium sulfate and the crude product is purified by silica gel flash chromatography. A colorless solid (0.735 g) is obtained in 55% yield.

Commercial Utility

The compounds according to the present invention have valuable pharmacological properties, which can make them commercially applicable.

Thus, for example, pyrazolopyrimidine derivatives according to this invention can act as inhibitors of the protein kinase B (PKB)/Akt and exhibit cellular activity; and these pyrazolopyrimidine compounds are expected to be commercially applicable in the therapy of diseases responsive to the inhibition of this protein kinase.

The protein kinase B (PKB)/Akt is a serine/threonine specific protein kinase, which, for example, plays an important role for regulating cell survival and apotosis in human cancer.

Within the present invention, the protein kinase B (PKB)/Akt with the isoforms Akt1 (PKBα), Akt2 (PKB β) and Akt3 (PKB γ) is of particular importance.

Thus, these compounds according to this invention, which inhibit one or more isoforms of PKB/Akt, are a particular interesting embodiment of the compounds according to this invention.

Compounds according to this invention might be selective in the inhibition of the protein kinase B (PKB)/Akt or one or more isoforms thereof; this means that those compounds may exhibit greater inhibition against said protein kinases, when compared to the compounds inhibiting the activity of other protein kinases like e.g. protein kinase A (PKA).

These selective compounds are a preferred embodiment of the compounds according to this invention.

Further on, compounds according to this invention may be inhibitors of mentioned protein kinase activity in cells and tissues which might cause a shift towards dephosphorylated substrate proteins and as potential functional consequence, for example the induction of apoptosis, cell cycle arrest or sensitization towards chemotherapeutic or target-specific anti-cancer drugs.

In another embodimental detail of this invention, compounds according to this invention may exhibit anti-proliferative properties. Accordingly, these compounds can be useful for anti-proliferation treatment of malignant cells. Therefore, compounds according to this invention are expected for use in the induction of a proliferation arrest in mammals such as humans.

Thus, compounds according to this invention can be useful in treating, preventing, inhibiting or ameliorating diseases of benign or malignant behaviour as described herein, such as e.g. (hyper)proliferative diseases.

As a further consequence, compounds according to this invention can be useful in treating, preventing, inhibiting or ameliorating of benign or malignant neoplasia, such as cancer.

A "neoplasia" is defined by cells displaying aberrant cell proliferation and/or survival and/or a block in differentiation. A "benign neoplasia" is described by hyperproliferation of cells, incapable of forming an aggressive, metastasizing tumor in-vivo. In contrast, a "malignant neoplasia" is described by cells with multiple cellular and biochemical abnormalities, capable of forming a systemic disease, for example forming tumor metastasis in distant organs.

More specifically, compounds according to this invention are expected to be useful in the treatment of malignant neoplasia, also described as cancer. Examples of malignant neoplasia include solid and haematological tumors. Solid tumors can be exemplified by tumors of the breast, bladder, bone, brain, central and peripheral nervus system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasia include inherited cancers exemplified by Retinoblastoma and Wilms tumor. In addition, malignant neoplasia include primary tumors in said organs and corresponding secondary tumors in distant organs ("tumor metastases"). Hematological tumors can bee exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Compounds according to the present invention may commercially applicable for treatment, prevention or amelioration of the diseases of benign and malignant behavior as described herein, such as e.g. cancer, like those cancer diseases described above.

Neoplastic cell proliferation might also effect normal cell behaviour and organ function. For example the formation of new blood vessels, a process described as neovascularization, is induced by tumors or tumor metastases. Compounds according to this invention can be commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of PKB/Akt might lead to a resensitization towards standard chemotherapeutic or target specific cancer therapeutics. As a consequence, the commercial applicability of compounds according to this invention may not be limited to $1^{st}$ line treatment of cancer patients. In a preferred embodiment of this invention, cancer patients with resistance to cancer chemotherapeutics or target specific anti-cancer drugs may be also amenable for treatment with these compounds for e.g. $2^{nd}$ or $3^{rd}$ line treatment cycles. In particular, compounds according to this invention might be used in combination with standard chemotherapeutic or targeted drugs to resensitize tumors towards these agents.

Compounds according to this invention might also be useful in inhibiting tumor angiogenesis and metastasis.

Compounds according to this invention might further be useful in the chemoprevention of cancer. Chemoprevention means in this connection the inhibition of the development of invasive cancer by either blocking the initiating mutagenic event or by blocking the progression of premalignant cells that have already suffered an insult or inhibiting tumor relapse.

Further on, compounds according to this invention may be yet further useful in the treatment of cancers associated with irregularities in the activity of Akt. Such cancers include, but are not limited to ovarian, pancreatic and breast cancer.

Due to their anti-proliferative properties, compounds according to this invention may be also useful in the treatment of any disease process which features abnormal cellular proliferation, for example benign prostate hyperplasia, familial adenomatosis polyposis, neuro-fibromatosis, dermatoses, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, or fungal infections.

In another embodimental detail of this invention, compounds according to this invention may be cellular active, i.e. they may exhibit any cellular effect, in particular dephosphorylation of defined substrate proteins causing, as an example, induction of apoptosis or chemosensitization. The term "chemosensitization" is understood in a broad sense as sensitizing neoplastic cells for apoptotic stimuli in general. These stimuli include, for example, effectors of death receptor and survival pathways as well as cytotoxic/chemotherapeutic and targeted agents and finally also radiation. The term "induction of apoptosis" and analogous terms are used to identify a compound which excecutes programmed cell death in cells contacted with that compound alone or in combination with other compounds routinely used for therapy. "Apoptosis" is defined by complex biochemical events within the contacted cell, such as the activation of cystein specific proteinases ("caspases") and the fragmentation of chromatin. Induction of apoptosis in cells contacted with the compound might not necessarily coupled with inhibition of cell proliferation. Advantageously, the inhibition of proliferation and/or induction of apoptosis are specific to cells with aberrant cell growth.

Some of the compounds according to this invention may induce cellular effects as mentioned herein alone or in combination with standard cytotoxic or targeted cancer drugs.

Thus, compounds according to this invention may be useful in the therapy of diseases with aberrant apoptosis-inducing response, such as e.g. cancer.

Compounds according to the present invention exhibit anti-proliferative and/or pro-apoptotic and/or chemosensitizing properties. Accordingly the compounds of the present invention are useful for treatment of malignant cells. Therefore the compounds of the present invention are expected for use in the production of an anti-proliferative and/or pro-apoptotic and/or chemosensitizing effect in mammals such as human being.

It is further worthy to be mentioned, that compounds according to this invention can also be inhibitors of cyclin-dependent kinases (CDKs), especially CDK2.

Thus, compounds according to this invention can be inhibitors of the activity and function of one or more of the abovementioned protein kinases. A particular embodiment of the compounds according to this invention refers hereby to those compounds of this invention which predominantly inhibit one of the abovementioned protein kinases, preferably PKB/Akt or one or more of its isoforms.

The cyclin dependent kinases are serine/threonine protein kinases, which, for example, are the driving force behind the cell cycle and cell proliferation; in this connection, particularly CDK2 and CDK4 are worthy to be mentioned because their activities are frequently misregulated in a wide variety of human cancers.

CDKs regulate initiation, progression and completion of the mammalian cell cycle, and thus compounds according to this invention can be useful in therapy of diseases associated with CDKs, such as e.g. those diseases mentioned in WO 2004/026867, the disclosure of which is incorporated herein.

As mentioned afore, due to their anti-proliferative properties, compounds according to this invention may be useful in the therapy of proliferative diseases. Many of these diseases and disorders are listed in U.S. Pat. No. 6,413,974, the disclosure of which is incorporated herein.

The pharmacological properties of the compounds of this invention can be confirmed by a number of pharmacological assays, such as e.g. those exemplified pharmacological assays which are described later.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

The present invention further includes a method for treating mammals, including humans, which are suffering from one of the abovementioned conditions, illnesses, disorders or diseases. The method comprises that a pharmacologically active and therapeutically effective and tolerable amount of one or more of the compounds according to the present invention is administered to the subject in need of such treatment.

The present invention further includes a method for treating, preventing, inhibiting or ameliorating diseases mediated by a dysregulated function of one or more of the aforesaid protein kinases, with PKB/Akt as a particular example, or downstream protein kinases dependent thereof within a defined pathway or signalling network, in a mammal, including human, comprising administering a pharmacologically active and therapeutically effective and tolerable amount of one or more of the compounds according to the present invention to said mammal.

The present invention further includes a method for treating, preventing, inhibiting or ameliorating diseases responsive to inhibition of protein kinases mentioned above, such as e.g. one or more isoforms of PKB/Akt, in a mammal, including human, comprising administering a pharmacologically active and therapeutically effective and tolerable amount of one or more of the compounds according to the present invention to said mammal.

The present invention further includes a method for treating (hyper)proliferative diseases of benign or malignant behaviour and/or disorders responsive to induction of apoptosis, such as e.g. benign or malignant neoplasia, like cancer, particularly any of those cancer diseases described herein above, in a mammal, including human, comprising administering a pharmacologically active and therapeutically effective and tolerable amount of one or more of the compounds according to the present invention to said mammal.

The present invention further relates to a method for treating benign and/or malignant neoplasia, such as, for example, any of those diseases mentioned herein, such as e.g. cancer, in a mammal, including human, comprising administering a pharmacologically active and therapeutically effective and tolerable amount of one or more of the compounds according to the present invention to said mammal.

The present invention further includes a method for inhibiting cellular (hyper)proliferation or arresting aberrant cell growth in a mammal, including human, comprising administering a pharmacologically active and therapeutically effective and tolerable amount of one or more of the compounds according to the present invention to said mammal.

The present invention further includes a method for inducing apoptosis in cells of aberrant cell growth in a mammal, including human, comprising administering a pharmacologically active and therapeutically effective and tolerable amount of one or more of the compounds according to the present invention to said mammal.

The present invention further includes a method for inhibiting PKB/Akt activity and/or CDK, such as e.g. CDK2, activity in a mammal, including human, comprising administering a pharmacologically active and therapeutically effective and tolerable amount of one or more of the compounds according to the present invention to said mammal.

The present invention further includes a method for inhibiting PKB/Akt activity, or the activity of one or more of its isoforms, in the treatment of diseases which are responsive thereto, such as e.g. any of those diseases mentioned above, in a mammal, including human, comprising administering a pharmacologically active and therapeutically effective and tolerable amount of one or more of the compounds according to the present invention to said mammal.

The present invention further includes a method for treating malignant neoplasia, such as e.g. cancer, particularly any of those cancer diseases described herein above, by sensitizing towards chemotherapeutic or target-specific anti-cancer drugs in a mammal, including human, comprising administering a pharmacologically active and therapeutically effective and tolerable amount of one or more of the compounds according to the present invention to said mammal.

The present invention further includes a method for sensitizing towards chemotherapeutic or target- specific anti-cancer agents in a mammal, including human, comprising administering a pharmacologically active and therapeutically effective and tolerable amount of one or more of the compounds according to the present invention to said mammal.

The present invention further relates to the use of compounds according to the present invention for the manufacture of pharmaceutical compositions which can be used in the treatment, prevention, inhibition or amelioration of those diseases mentioned herein, such as, in a particular example, cancer.

The present invention further relates to the use of compounds according to the present invention for the manufacture of pharmaceutical compositions which can be used in the treatment, prevention or amelioration of diseases responsive to protein kinase inhibitor treatment, for example PKB/Akt inhibitor treatment, such as e.g. those diseases mentioned herein.

The present invention further relates to the use of compounds according to the present invention for the manufacture of pharmaceutical compositions which can be used in the treatment, prevention or amelioration of diseases responsive to arresting of aberrant cell growth and/or inducing of apoptosis, such as e.g. those diseases mentioned herein, e.g. cancer, particularly any of those cancer diseases mentioned herein.

The present invention further relates to the use of compounds according to the present invention for the manufacture of pharmaceutical compositions which can be used in the treatment, prevention or amelioration of (hyper)proliferative diseases of benign or malignant behaviour and/or disorders responsive to the induction of apoptosis in a mammal, such as e.g. those diseases mentioned herein.

The present invention further relates to the use of compounds according to the present invention for the manufacture of pharmaceutical compositions which can be used in the treatment of benign and/or malignant neoplasia, such as e.g. cancer, particularly any of those cancer diseases described herein above.

The present invention further relates to the use of compounds according to the present invention for the manufacture of pharmaceutical compositions, which can be used for sensitizing towards chemotherapeutic and/or target-specific anti-cancer agents, such as e.g. any of those anti-cancer agents mentioned herein above.

The present invention further relates to the use of compounds according to the present invention for the manufacture of pharmaceutical compositions, which can be used for sensitizing towards radiation therapy of those diseases mentioned herein, especially cancer, particularly any of those cancer diseases mentioned herein above.

The present invention further relates to the use of compounds according to the present invention for the manufacture of pharmaceutical compositions, which can be used in the treatment of diseases sensitive to abovementioned protein kinase inhibitor therapy and different to cellular neoplasia. These non-malignant diseases include, but are not limited to those mentioned herein, such as e.g. benign prostate hyperplasia.

The present invention further relates to pharmaceutical compositions comprising one or more of the compounds according to the present invention and a pharmaceutically acceptable carrier or diluent.

The present invention further relates to combinations comprising one or more of the compounds according to the present invention and pharmaceutically acceptable auxiliaries, excipients or vehicles, e.g. for use in the treatment, prevention or amelioration of (hyper)proliferative diseases of benign or malignant behaviour and/or disorders responsive to the induction of apoptosis in a mammal, such as e.g. any of those diseases mentioned herein, especially cancer, particularly any of those cancer diseases described herein above.

The present invention further relates to a composition consisting essentially of a therapeutically effective and tolerable amount of one or more compounds according to the present invention together with the usual pharmaceutically acceptable vehicles, diluents and/or excipients for use in therapy, e.g. for treating diseases sensitive to inhibition of protein kinases.

The present invention further relates to compounds according to the present invention for use in therapy, in particular in the therapy of those diseases mentioned herein.

The present invention further relates to compounds according to the present invention for use in therapy, such as, for example, in the treatment, prevention or amelioration of diseases sensitive to inhibition of abovementioned protein kinases, in particular PKB/Akt, such as e.g. (hyper)proliferative diseases of benign or malignant behaviour and/or disorders responsive to the induction of apoptosis, such as e.g. those diseases mentioned herein, particularly cancer.

The present invention further relates to compounds according to this invention having PKB/Akt inhibiting properties.

The present invention further relates to compounds according to this invention having CDK, especially CDK2, inhibiting properties.

The present invention further relates to compounds according to the present invention having anti-proliferative and/or apoptosis inducing activity.

Additionally, the invention relates to an article of manufacture, which comprises packaging material and a pharmaceutical agent contained within said packaging material, wherein the pharmaceutical agent is therapeutically effective for inhibiting the effects of one or more of the abovementioned protein kinases, such as e.g. inhibiting the protein kinase B/Akt, ameliorating the symptoms of a disorder mediated by one or more of said protein kinases, and wherein the packaging material comprises a label or package insert which indicates that the pharmaceutical agent is useful for preventing, inhibiting, ameliorating or treating disorders mediated by one or more of said protein kinases, and wherein said pharmaceutical agent comprises one or more of the compounds according to the present invention. The packaging material, label and package insert otherwise parallel or resemble what is generally regarded as standard packaging material, labels and package inserts for pharmaceuticals having related utilities.

The pharmaceutical compositions according to this invention can be prepared by processes which are known per se and familiar to the person skilled in the art. As pharmaceutical compositions, the compounds of the present invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, pre-servatives, solubilizers, colorants, complexing agents or permeation promoters, can be used.

Depending upon the particular disease, to be treated or prevented, additional therapeutic active agents, which are normally administered to treat or prevent that disease, may optionally be coadministered with compounds according to the present invention. As used herein, additional therapeutic agents that are normally administered to treat or prevent a particular disease are known as appropriate for the disease being treated.

For example, compounds according to the present invention may be combined with one or more standard therapeutic agents or radiation used for treatment of the diseases as mentioned before. Thus, in one particular embodiment, compounds according to the present invention may be combined with one or more art-known anti-cancer agents, such as e.g. with one or more chemotherapeutic and/or target specific anti-cancer agents, and/or radiation.

Examples of known chemotherapeutic anti-cancer agents used in cancer therapy include, but not are limited to (i) alkylating/carbamylating agents such as Cyc1 ophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin or carboplatin (Carboplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof, epothilones such as Epothilone B (Patupilone®), Azaepothilone (Ixabepilone®) or ZK-EPO, a fully synthetic epothilone B analog; (iv) topoisomerase inhibitors such as anthracyclines such as Doxorubicin (Adriblastin®), epipodophyllotoxines such as Etoposide (Etopophos®) and camptothecin and camptothecin analogs such as Irinotecan (Camptosar®) or Topotecan (Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) and pemetrexed (Alimta®).

Examples of target specific anti-cancer drug classes used in experimental or standard cancer therapy include but are not limited to (i) kinase inhibitors such as e.g. Imatinib (Glivec®), ZD-1839/Gefitinib (Iressa®), BAY43-9006 (Sorafenib), SU11248/Sunitinib (Sutent®) or OSI-774/Erlotinib (Tarceva®); (ii) proteasome inhibitors such as PS-341/Bortezomib (Velcade®); (iii) histone deacetylase inhibitors like SAHA, PXD101, MS275, MGCDO103, CI-994, Depsipeptide/FK228, NVP-LBH589, LAQ-824, Valproic acid (VPA) and butyrates; (iv) heat shock protein 90 inhibitors like 17-allylaminogeldanamycin (17-AAG); (v) vascular targeting agents (VAT) like combretastatin A4 phosphate or AVE8062/AC7700 and anti-angiogenic drugs like VEGF antibodies, such as e.g. Bevacizumab (Avastin®), or KDR tyrosine kinase inhibitors, such as e.g. PTK787/ZK222584 (Vatalanib); (vi) monoclonal antibodies such as Trastuzumab (Herceptin®) or Rituximab (MabThera/Rituxan®) or Alemtuzumab (Campath®) or Tositumab (Bexxar®) or C225/Cetuximab (Erbitux®) or Avastin (see above) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®); (viii) Toll-like receptor/TLR 9 agonists like Promune®; (ix) protease inhibitors (x) hormonal therapeutics such as anti-estrogens (e.g. Tamoxifen or Raloxifen), anti-androgens (e.g. Flutamide or Casodex), LHRH analogs (e.g. Luprolide, Goserelin or Triptorelin) and aromatase inhibitors.

Other known target specific anti-cancer agents which can be used for combination therapy include bleomycin, retinoids such as all-trans retinoic acid (ATRA), DNA methyltransferase inhibitors such as the 2-deoxycytidine derivative Decitabine (Docagen®), alanosine, cytokines such as interleukin-2 or interferons such as interferon oc2 or interferon-γ, death receptor agonists, such as TRAIL, DR4/5 agonistic antibodies, FasL and TNF-R agonists.

As exemplary anti-cancer agents which may be useful in combination therapy according to the present invention any of the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAM-BUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PATUPILONE, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VERTEPORFIN, VINBLASTINE, VINCRISTINE, VINDESINE, VINORELBINE, VOROZOLE and ZEVALIN.

The person skilled in the art is aware on the base of his/her expert knowledge of the total daily dosage(s) and administration form(s) of the additional therapeutic agent(s) coadministered. Said total daily dosage(s) can vary within a wide range.

In practicing the present invention, compounds according to the present invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in a particular example, art-known anti-cancer agents, such as e.g. any of those mentioned above (e.g. chemotherapeutic and/or target specific anti-cancer agents).

In this context, the present invention further relates to a combination comprising a first active ingredient, which is at least one compound according to the present invention, and a second active ingredient, which is at least one standard therapeutic, in particular at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The term "combination" according to the present invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The present invention further relates to a pharmaceutical composition comprising a first active ingredient, which is at least one compound according to the present invention, and a second active ingredient, which is at least one standard therapeutic agent, in particular at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy, such as e.g. in therapy of diseases responsive to the inhibition of PKB/Akt, particularly (hyper)proliferative diseases and/or disorders responsive to induction of apoptosis, such as e.g. any of those diseases mentioned herein, like benign or malignant neoplasia, especially cancer, particularly any of those cancer diseases described above.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to the present invention, and a pharmaceutically acceptable carrier or diluent; a preparation of a second active ingredient, which is an standard therapeutic agent, for example an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat benign and/or malignant neoplasia, such as e.g. cancer, particularly any of those cancer diseases described above.

The present invention further relates to a combined preparation comprising at least one compound according to the present invention and at least one known therapeutic agent, for example at least one art-known anti-cancer agent for simultaneous, concurrent, sequential or separate administration.

In this connection, the present invention further relates to combinations, compositions, formulations, preparation or kits according to the present invention having PKB/Akt inhibiting properties.

Also in this connection, the present invention further relates to combinations, compositions, formulations, preparation or kits according to the present invention having anti-(hyper)proliferative and/or apoptosis inducing activity.

Also in this connection, the present invention further relates to combinations, compositions, formulations, preparation or kits according to the present invention having CDK, especially CDK2, inhibiting properties.

In addition, the present invention further relates to a method for treating diseases and/or disorders responsive to the inhibition of PKB/akt, such as e.g. (hyper)proliferative diseases and/or disorders responsive to induction of apoptosis, like cancer, in a patient comprising administering a combination, composition, formulation, preparation or kit as described herein to said patient in need thereof.

In addition, the present invention further relates to a method for treating diseases and/or disorders mediated by a dysregulated function of one or more of the abovementioned protein kinases, with the protein kinase B (PKB)/Akt as a particular example, or downstream protein kinases dependent thereof within a defined pathway or signalling network, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to the present invention and a pharmaceutically acceptable carrier or diluent, and a pharmaceutically active and therapeutically effective and tolerable amount of one or more standard therapeutic agents, for example, one or more art-known anti-cancer agents, such as e.g. one or more of those mentioned herein, to said patient in need thereof.

In further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating those diseases mentioned herein.

The present invention further relates to the use of one or more of the compounds according to this invention for the manufacture of a medicament for use in combination with one or more anti-cancer agents, e.g. one or more anti-cancer agents selected from chemotherapeutic and target-specific anti-cancer agents, such as e.g. from those mentioned herein, for the treatment of cancer, particularly for the treatment of any one of those cancer diseases mentioned above.

The present invention further relates to a commercial package comprising one or more compounds of the present invention together with instructions for simultaneous, sequential or separate use with one or more standard therapeutics, such as e.g. one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, sequential or separate use with one or more standard therapeutics, such as e.g. art-known anti-cancer agents, such as e.g. any of those mentioned herein.

The present invention further relates to a commercial package comprising one or more art-known anti-cancer agents, such as e.g. any of those mentioned herein, together with instructions for simultaneous, sequential or separate use with one or more compounds according to the present invention.

The compositions, combinations, preparations, formulations, kits or packages mentioned in the context of the combination therapy according to the present invention may include one or more than one of the compounds according to the present invention and/or one or more than one of the standard therapeutics, such as e.g. the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a (hyper)proliferative disease and/or disorders responsive to induction of apoptosis, such as e.g. benign or malignant neoplasia, like cancer, particularly any one of those cancer diseases mentioned herein.

In addition, compounds according to the present invention can be used in the pre- or post-surgical treatment of cancer.

In further addition, compounds of the present invention can be used in combination with radiation therapy, in particular in sensitisation of cancer patients towards standard radiation therapy.

A combination according to the present invention can refer to a composition comprising both the compound according to the present invention and the other standard therapeutics, such as e.g. one or more active anti-cancer agents in a fixed combination (fixed unit dosage form), or a medicament pack comprising the two active ingredients as discrete separate dosage forms (non-fixed combination). In case of a medicament pack comprising the two active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

The administration of the pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention can be in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations, which may be mentioned, are, for example, powders, emulsions, suspensions, sprays, oils, ointments, fatty ointments, creams, pastes, gels or solutions.

The pharmaceutical compositions according to the invention can be prepared by processes known per se. The dosage of the compounds of the invention (=active compounds) is carried out in the order of magnitude customary for protein kinase inhibitors. Topical application forms (such as e.g. ointments) for the treatment of dermatoses thus contain the active compounds in a concentration of, for example, 0.1-99%. The customary dose in the case of systemic therapy (p.o.) is between 0.03 and 30 mg/kg per day, (i.v.) is between 0.03 and 30 mg/kg/h. In another embodiment, the dose the case of systemic therapy (p.o.) is between 0.3 and 30 mg/kg per day, (i.v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Biological Investigations

Expression and Purification of ΔPHAkt1, Akt1(Active), Akt1 (Inactive), PDK1 cdk2 and PKA:

For the biochemical assay ΔPHAkt1 is used devoid of its PH domain as a GST fusion protein (named GST-deltaPH-Akt1; 107-480aa; cloned in the pAcG1 vector (BD Biosciences Pharmingen)), co-expressed with PDK1 in SF9 insect cells. The protein is purified using glutathion-affinity chromatography by standard protocols.

For the biochemical Akt1 assay recombinant full-length human Akt1, containing N-terminal His6 tag is cloned and expressed in baculovirus infected Sf21 insect cells. Akt1 is activated with GST-MAPKAP-K2 and PDK1, and repurified on Ni2+/NTA-agrose and glutathioneagarose (Upstate, UK; #14-276).

For the biochemical Akt1 (inactive) assay recombinant full-length human Akt1 a containing N-terminal His6 tag is cloned and expressed in baculovirus infected Sf21 insect cells. The enzyme is purified using Ni2+/NTA-agarose (Upstate, UK; #14-279).

For the biochemical Akt1 (inactive) assay, recombinant full-length human PDK1, containing N-terminal His6 tag is cloned and expressed in baculovirus infected Sf21 insect cells. The enzyme is purified using Ni2+/NTA-agarose.

For the biochemical PKA assay the catalytic subunit of PKA is expressed in *E. coli* as a His-tagged human recombinant protein and purified accordingly (PanVera, USA; #R3791).

For the biochemical cdk2 assay the human cdk2 (amino acids M1-L298; N-terminally fused to GST; Proqinase, Freiburg, Germany) and the human cyclinE (amono acids M1-A394; N-terminally fused to GST; Proqinase, Freiburg, Germany) are coexpressed in Sf9 insect cells. The proteins are purified using glutathion-affinity chromatography by standard protocols. The expression and purification is performed cells at Proqinase (Freiburg, Germany).

Biochemical ΔPH Akt1 Assay:

In order to study the inhibition of Akt according to the invention, a flashplate-based assay has been developed.

The Akt1 assay is a biochemical assay using Akt1 devoid of its PH domain and co-expressed with PDK1 in insect cells. The GST-ΔPH-Akt1 assay is run in 96 well plates by incubating 100 ng/well GST-ΔPH-Akt1, 100 ng/well histone 2B (Roche, #223514) as substrate, 10 µl of compound of invention (test compounds were dissolved as 10 mM solutions in dimethylsulfoxide (DMSO) and subsequently diluted) and 100 nM ATP (including $^{33}$P-ATP) in 100 µl of reaction buffer (50 nM HEPES, pH7,5; 3 mM MgCl$_2$; 3 mM MnCl$_2$; 3 µM Na-Orthovanadat; 1 mM DTT; 1 µg/ml PEG8000) for 80 minutes at 30° C. The reactions are terminated by adding 100 µl stopping buffer (2% H$_3$PO$_4$ for 5 minutes) and are washed 3 times by using washing buffer (0.9% NaCl). Relying on the incorporation of $^{33}$P into the protein substrate histone 2B, the detection is based on the adhesion of the phosphorylated protein to the surface of scintillator-coated flash plates (NEN, USA; #SMP-200). This phosphorylation is measured by counting the plate for 60 sec. using a plate reader (Wallac Microbeta; Perkin Elmer, USA). The analysis of the data is performed using a biostatistical program (GraphPad Prism, USA). Preferred compounds show an IC$_{50}$ of deltaPH Akt1 inhibition below 5 µM or, particularly, below 2 µM.

Representative IC$_{50}$ values for deltaPHAkt1 inhibition determined in the aforementioned assay are depicted in the following table A, in which the numbers of the compounds correspond to the numbers of the examples.

TABLE A

| ΔPHAkt1 inhibition: | |
|---|---|
| Compounds | IC$_{50}$ (µmol/l) |
| 1, 6, 17 to 24, 27 to 30, 32 to 48, 50 to 61, 63, 65, 67 to 70, 72, 75 to 78, 80 to 82, and 84 to 91 | The inhibitory values of these listed Examples are ≤1.75 |
| 10, 12, 71, 73, and 74 | The inhibitory values of these listed Examples are ≤2.45 |

Biochemical Akt1 Assay (Full-length Akt1 Active):

In order to study the inhibition of Akt1 (full-length version) according to the invention, a flashplate-based assay has been developed.

The full-length Akt1 assay is a biochemical assay using Akt1 N-terminally fused to GST and co-expressed with PDKI in insect cells. The Akt1 assay is run in 96 well plates by incubating 500 ng/well GST-Akt1, 1 µM Crosstide (N-terminally biotinylated synthetic peptide (KGSGSGRPRTSS-FAEG) Upstate, #12-385) as substrate, 10 µl of test compound (test compounds were dissolved as 10 mM solutions in dimethylsulfoxide (DMSO) and subsequently diluted) and 100 nM ATP (including $^{33}$P-ATP) in 100 µl of reaction buffer (50 mM HEPES, pH7,5; 3 mM MgCl$_2$; 3 mM MnCl$_2$; 3 µM Na-Orthovanadat; 1 mM DTT; 1 µg/ml PEG8000) for 60 minutes at 30° C. in 96 well microtiter plates. The reactions are terminated by adding 100 µl stopping buffer (5M NaCl, 35 mM EDTA pH 8.0) for 5 minutes. 190µl of the reaction mixture are transferred into streptavidin-coated Flashplates (Perkin Elmer, #SMP-103) and incubated for further 30 minutes at room temperature. The plates are washed 3 times by using washing buffer (0.9% NaCl). Relying on the incorporation of $^{33}$P into the peptide substrate crosstide, the detection is based on the specific binding of the biotinylated peptide to the streptavidin-coated surface of scintillator-coated flash plates (NEN, USA; #SMP-103). This phosphorylation is measured by counting the plate for 60 sec. using a plate reader (Wallac Microbeta; Perkin Elmer, USA). The analysis of the data is performed using a biostatistical program (GraphPad Prism, USA). Preferred compounds show an IC$_{50}$ of full-length Akt1 (active) inhibition below 5 µM or, particularly, below 2 µM.

Representative IC$_{50}$ values for inhibition of Akt1 (full-length Akt1, active) determined in the aforementioned assay follow from the following table B, in which the numbers of the compounds correspond to the numbers of the examples.

TABLE B

| Akt1 inhibition (full-length Akt1, active): | |
|---|---|
| Compounds | IC$_{50}$ (µmol/l) |
| 24, 59, 61, 63 and 87 | The inhibitory values of these listed Examples are ≤4.03 |

Biochemical Akt1 Assay (Full-length Akt1 Inactive):

In order to study the inhibition of Akt1 activation of the compounds according to the invention, an IMAP-based assay has been developed for the protein kinase B alpha, PKBα (fullAkt1, inactive). PDK1-dependent activation and subsequent enzymatic activity of Akt1: Activity of purified human Akt1 is routinely measured in an assay in which the enzyme is first activated by PDK1 in the presence of phosphatidylinositol-3,4,5-triphosphate (PIP3). Once activated, Akt1-dependent phosphorylation of a fluorescence labelled peptide substrate is measured by fluorescence polarisation using the IMAP technology (Molecular Devices).

This Akt-activation-assay uses inactive full length AKT1 (Upstate, #25675U), full length PDK1, a fluorescence labelled AKT1 substrate peptide (Thermo Electron GmbH, 5-Fluorescein-NH-RARTSSFAEPG-CONH$_2$), and phospholipid vesicles (PIP3, Biomol, Cat. #PH-107;DOPC/DOPS "Upstate Lipid Blend", Avanti Polar Lipids, Cat. #790595P).

The phospholipids are prepared as follows: 5 mg DOPC/DOPS are solved in 200 µl 10 mM Tris (pH 7.4) and 300 µg PIP3 are resuspended in 950 µl 10 mM Tris (pH 7.4) by pipetting. 950 µl solved PIP3 are mixed with 50 µl solved DOPC/DOPS and incubated for 2 h at a temperature below 20° C. Then the mixture is subjected to sonification for 30 min. at max. power until a translucent phopholipid vesicle preparation is obtained. Aliquots of the vesicle suspension are frozen at -80° C. until needed, likewise the solved DOPC/DOPS.

Assays are performed in 384-well plates. Incubations are carried out for 60 min. at room temperature. The reaction buffer mixture contained in a final volume of 25 µl: 10 mM Tris pH 7,4, 10 mM MgCl$_2$. 1 mM DTT, and 0.1 mg/ml BSA. In contrast the activation buffer contained: 50 ng/well Akt1, 20 ng/well PDK1, 1.25 µM peptide substrat, 50 µM ATP, and phospholipid vesicles (1:20). Test compounds are added from stock solutions in DMSO before activation of Akt1 by PDK1. After the incubation the beads (IMAP binding reagent; Molecular Devices; 1:167) are added and the fluorescence polarization is measured (excitation 485 nm, emission 530 nm). The analysis of the data is performed using a biostatistical program.

Preferred compounds show an $IC_{50}$ of full-length Akt1 (inactive) inhibition below 5 µM or, particularly, below 2 µM.

Representative $IC_{50}$ values for inhibition of Akt1 (full-length Akt1, inactive) determined in the aforementioned assay follow from the following table C, in which the numbers of the compounds correspond to the numbers of the examples.

TABLE C

| Inhibition of Akt1 activation (full-length Akt1, inactive): | |
| --- | --- |
| Compounds | $IC_{50}$ (µmol/l) |
| 24, 59, 61, 63 and 87 | The inhibitory values of these listed Examples are $\leq 5.0$ |

Biochemical PKA Assay:

In order to study the kinase inhibition activity of the compounds according to the invention, a flashplate-based assay has been developed for the serine/threonine kinase, PKA. The assay is run in 96 well plates by incubating 1 ng/well His-PKA (PanVera, USA; #R3791), 0.5 µM/well PKA peptide (#12-394; Upstate, USA) as substrate, 10 µl of compound of invention (test compounds were dissolved as 10 mM solutions in dimethylsulfoxide (DMSO) and subsequently diluted) and 100 nM ATP (including $^{33}$P-ATP) in 100 µl of reaction buffer (50 nM HEPES, pH7,5; 3 mM $MgCl_2$; 3 mM $MnCl_2$; 3 µM Na-Orthovanadat; 1 mM DTT) for 80 minutes at 22° C. The reactions are stopped by adding 100 µl stopping buffer (2% $H_3PO_4$ for 5 minutes) and are washed 3 times by using washing buffer (200 µl 1×PBS). Relying on the incorporation of $^{33}$P into the peptide substrate, the detection is based on the adhesion of the phosphorylated peptide to the surface of scintillator-coated Flash plates (Perkin Elmer, USA; #SMP-103). This phosphorylation is measured by counting the plate for 60 sec. using a plate reader (Wallac Microbeta; Perkin Elmer, USA). By using this method the $IC_{50}$ of the PKA inhibition is determined. The analysis of the data is performed using a biostatistical program (GraphPad Prism, USA).

Preferred compounds show an $IC_{50}$ of PKA inhibition above 5 µM or, particularly, above 10 µM.

Representative $IC_{50}$ values for PKA inhibition determined in the aforementioned assay are depicted in the following table D, in which the numbers of the compounds correspond to the numbers of the examples.

TABLE D

| PKA inhibition: | |
| --- | --- |
| Compounds | $-\log IC_{50}$ (mol/l) |
| 1, 23, 27 to 30, 33, 35, 38, 41, 42, 46, 47, 48, 50, 51, 52, 53, 55, 57, and 58 | These listed Examples do not substantially inhibit PKA (<4.0) |
| 32, 34, 36, 37, 39, 40, 43, 54, 56, 59, 60, 61, 63, 65, 67, 68, 69, and 70 | The inhibitory values of these listed Examples are in the range from 4.0 to 5.2 |

Biochemical cdk2 Assay:

In order to study the kinase inhibition activity of the compounds according to the invention, a Flashplate-based assay is developed for the cyclin-dependent kinase 2, cdk2. The cdk2 assay is run in 96 well plates by incubating 50ng/well cdk2 (cdk2/cyclinE; Proqinase, Freiburg, Germany), 10 ng/well Histon 1 (#223-549; Roche) as substrate, 10 µl of compound of invention (test compounds are dissolved as 10 mM solutions in dimethylsulfoxide (DMSO) and subsequently diluted) and 100 nM ATP (including $^{33}$P-ATP) in 100 µl of reaction buffer (50 mM HEPES, pH7,5; 3 mM $MgCl_2$; 3 mM $MnCl_2$; 3 µM Na-Orthovanadat; 1 mM DTT) for 80 minutes at 30° C. The reactions are stopped by adding 100 µl stopping buffer (2% $H_3PO_4$ for 5 minutes) and are washed 3 times by using washing buffer (200 µl $H_2O$). Relying on the incorporation of $^{33}$P into the substrate, the detection is based on the adhesion of the phosphorylated substrate to the surface of scintillator-coated Flash plates (NEN, USA; #SMP-200). This phosphorylation is measured by counting the plate for 60 sec. using a plate reader (Wallac Microbeta; Perkin Elmer, USA). By using this method the $IC_{50}$ of the cdk2 inhibition is determined. The analysis of the data is performed using a biostatistical program (GraphPad Prism, USA).

Preferred compounds of this invention show an $IC_{50}$ of cdk2 inhibition below 5 µM or, particularly, below 1 µM.

Representative $IC_{50}$ values for cdk2 inhibition determined in the aforementioned assay follow from the following table E, in which the numbers of the compounds correspond to the numbers of the examples.

TABLE E

| CDK2 inhibition: | |
| --- | --- |
| Compounds | $-\log IC_{50}$ (mol/l) |
| 1, 24, 30, 46, 48, 50 and 55 | The inhibitory values of these listed Examples lie in the range from 5.8 to 7.1 |

Cellular PI3K/Akt Pathway Assay

In order to study the cellular activity of the compounds according to the invention, an ELISA-based assay has been established. The assay is based on a Sandwich ELISA kit (PathScan™ Phospho-Akt1 (Ser473); Cell Signaling, USA; #7160).

The assay detects endogenous levels of phosphorylated Akt1 protein. A phospho-Akt (Ser473) antibody (Cell Signaling, USA; #9271) has been coated onto the microwells. After incubation with cell lysates, the phosphorylated Akt protein is captured by the coated antibody. Following extensive washing, Akt1 monoclonal antibody (Cell Signaling, USA; #2967) is added to detect the captured phospho-Akt1 protein. HRP-linked anti-mouse antibody (Cell Signaling, USA; #7076) is then used to recognize the bound detection antibody. HRP substrate (=TMB; Cell Signaling, USA; #7160) is added to develop colour. The magnitude of optical density for this developed color is proportional to the quantity of phosphorylated Akt1 protein.

MCF7 cells (ATCC HTB-22) are seeded into 96 well fate bottom plates at a density of 10000 cells/well. 24 hours after seeding the cells are starved using estrogen-free medium (IMEM including 0.1% charcoal treated FCS). After 24 hours 1 µl each of the compound dilutions (test compounds were dissolved as 10 mM solutions in DMSO and subsequently diluted) are added into each well of the 96 well plates and incubated for 48 h at 37° C. in a humidified atmosphere containing 5% $CO_2$. To stimulate Akt phosphorylation, β-Heregulin (20 ng/ml) is added in parallel to the compounds. Wells containing unstimulated control cells (no β-Heregulin stimulation) are incubated with or without the diluted compound. Wells containing untreated control cells (no compound) are filled with medium containing 0.5% v:v DMSO and are with P-Heregulin or are not stimulated.

Cells are harvested under nondenaturing conditions and lysed with brief sonification in 1× cell lyses buffer (20 mM Tris (pH7.5), 150 mM NaCl, 1 mM ethylene diaminetetraacetate (EDTA), 1 mM ethylene glycolbis-(2-aminoethyl)-N,N,N',N'-tetraacetic acid (EGTA), 1% Triton X-100, 2.5 mM sodium pyrophosphate, 1 mM β-glycerolphosphate, 1 mM Na3VO4, 1 μg/ml leupeptin). The lysate is microcentrifuged for 10 minutes at 4° C. and the supernatant is transferred to a new tube. 100 μl of sample diluent (0.1% tween-20, 0.1% sodium azide in 20× PBS) are added to a microcentrifuge tube and 100 μl of cell lysate are transferred into the tube and vortexed. 100 μl of each diluted cell lysate are added to the appropriate well (phospho-Akt (Ser473) antibody coated microwells; Cell Signaling, USA; #7160) and incubated overnight at 4° C. The plates are washed 4 times with 1× wash buffer (1% tween-20, 0.33% thymol, in 20×PBS). Then 100 μl of detection antibody (Akt1 (2H10) monoclonal detection antibody; Cell Signaling, USA; #2967) are added to each well and incubated for 1 h at 37° C. The washing procedure is repeated between each step. 100 μl of HRP-linked secondary antibody (anti-mouse IgG HRP-linked antibody; Cell Signaling, USA; #7076) are added to each well and incubated for 30 minutes at 37° C. Than 100 μl of TMB substrate (0.05% 3,3',5,5' tetramethylbenzidine, 0.1% hydrogen peroxide, complex polypeptides in a buffered solution; Cell Signaling, USA; #7160) are added to each well and incubated for 30 minutes at 25° C. Finally 100 μl of STOP solution (0.05% α and P unsaturated carbonyl compound) are added to each well and the plate are shaked gently for a few seconds. The absorbance is read at 450 nm (Wallac Victor2; Perkin Elmer, USA) within 30 minutes after adding STOP solution. The analysis of the data is performed using a statistical program (Excel; Microsoft, USA).

Preferred compounds show an inhibitory activity (IC50) towards Akt phosphorylation below 10 μM.

Representative $IC_{50}$ values for Akt pathway inhibition determined in the aforementioned assay follow from the following table F, in which the numbers of the compounds correspond to the numbers of the examples.

TABLE F

| Akt pathway inhibition (pAkt-ELISA): | |
| --- | --- |
| Compounds | $IC_{50}$ (μmol/l) |
| 24, 59, 63 and 87 | The inhibitory values of these listed Examples are ≦6 |

Cellular PGSK3 Assay:

In order to study the cellular activity of the compounds according to the invention, an ELISA-based assay has been established for the phosphorylated glycogen synthetase kinase 3, GSK3. The assay is based on a solid phase sandwich ELISA that detects endogenous levels of the phosphorylated GSK3 (BioSource International, Inc.; Catalog #KH00461). A phospho-GSK3 (Ser9) antibody has been coated onto the microwells. After incubation with cell lysates, the coated antibody captures the phosphorylated GSK3 protein. Following extensive washing, GSK3 polyclonal antibody is added to detect the captured phospho-GSK3 protein. HRP-linked anti-mouse antibody (anti-rabbit IgG-HRP) is then used to recognize the bound detection antibody. After the second incubation and washing to remove all the excess anti-rabbit IgG-HRP, a substrate solution is added, which is acted upon by the bound enzyme to produce color. The intensity of this colored product is directly proportional to the concentration of GSK-3 β [pS9] present in the original specimen.

MCF7 cells (ATCC HTB-22) are seeded into 96 well plates at a density of 10000 cells/well. After 24 hours 1 μl each of the compound dilutions (test compounds were dissolved as 10 mM solutions in DMSO and subsequently diluted) are added into each well of the 96 well plates and incubated for 48 h at 37° C. in a humidified atmosphere containing 5% $CO_2$.

Cells are harvested and lysed with brief vortexing in cell extraction buffer (10 mM Tris, pH 7.4, 100 mM NaCl, 1 mM EDTA, 1 mM EGTA, 1 mM NaF, 20 mM Na4P2O7, 2 mM Na3VO4, 1% Triton X-100, 10% glycerol, 0.1% SDS, 0.5% deoxycholate, 1 mM PMSF). The lysate are centrifuged for 10 minutes at 4° C. and the supernatant transferred to a new tube. 50 μl of sample diluent (standard diluent buffer, Biosource) are added and 100 μl of cell lysate transferred into the tube and vortexed. 100 μl of each diluted cell lysate are added to the appropriate well (phospho-GSK3 (Ser9) antibody coated microwells; BioSource) and incubated for 3 h at room temperature. The plates are washed 4 times with 1× wash buffer (Biosource). 50 μl of detection antibody (GSK3 (Ser9) detection antibody; BioSource) are added to each well and incubated for 30 min. at room temperature. The washing procedure is repeated between each step. 100 μl of HRP-linked secondary antibody (anti-mouse IgG HRP-linked antibody) are added to each well and incubated for 30 minutes at room temperature. 100 μl of TMB substrate (0.05% 3,3',5,5' tetramethylbenzidine, 0.1% hydrogen peroxide, complex polypeptides in a buffered solution; Biosource) are added to each well and incubated for 30 minutes at room temperature. Finally 100 μl of Stop solution (0.05% α and β unsaturated carbonyl compound) are added to each well and the plate are shaked gently for a few seconds. The absorbance is measured at 450 nm (Wallac Victor2; Perkin Elmer, USA) within 30 minutes after adding Stop solution. The analysis of the data is performed using a statistical program (Microsoft Excel, USA) and the inhibition of pGSK3 phosphorylation is determined.

Preferred compounds show an inhibitory activity (IC50) towards GSK3 inhibition below 10 μM.

Representative $IC_{50}$ values for GSK3 inhibition determined in the aforementioned assay follow from the following table G, in which the numbers of the compounds correspond to the numbers of the examples.

TABLE G

| GSK3 inhibition (pGSK3-ELISA): | |
| --- | --- |
| Compounds | $IC_{50}$ (μmol/l) |
| 24, 59 and 63 | The inhibitory values of these listed Examples are <10 |

Cellular Proliferation/Cytotoxicity Assay:

The anti-proliferative activity of the compounds as described herein, is evaluated using MCF7 and MDA-MB-468 (ATCC HTB-22 and HTB-132) cell lines and the Alamar Blue (Resazurin) cell viability assay (O'Brien et al. Eur J Biochem 267, 5421-5426, 2000). Resazurin is reduced to the fluorescent resorufin by cellular dehydrogenase activity, correlating with viable, proliferating cells. Test compounds are dissolved as 10 mM solutions in DMSO and subsequently diluted. MCF7 or MDA-MB-434 cells were seeded into 96 well flat bottom plates at a density of 10000 cells/well (MCF7) or 5000 cells/well (MDA-MB-468) in a volume of 200 μl/well. 24 hours after seeding, 1 μl each of the compound dilutions are added into each well of the 96 well plates. Each compound dilution is tested as at least as duplicates. Wells containing untreated control cells were filled with 200 μl DMEM containing 0.5% v:v DMSO. The cells are then incubated with the substances for 48 hours at 37° C. in a humidified atmosphere containing 5% carbon dioxide. To determine cell viability, 20 μl of a Resazurin solution (Sigma; 90 mg/l) are added. After 4 hours incubation at 37° C. the fluorescence is measured at an extinction of 544 nm and an emission of 590 nm (Wallac Victor2; Perkin Elmer, USA). For the calculation of the cell viability the emission value from untreated cells is set as 100% viability and the emission rates of treated cells are set in relation to the values of untreated cells. Viabilities are expressed as % values. The corresponding $IC_{50}$ values of the compounds for cytotoxic activity are determined from the concentration-effect curves by means of non-linear regression. The analysis of the data is performed using a biostatistical program (GraphPad Prism, USA).

Representative $IC_{50}$ values for anti-proliferative/cytotoxic potency determined in the aforementioned assay are depicted in the following table H, in which the numbers of the compounds correspond to the numbers of the examples.

TABLE H

| Anti-proliferative/cytotoxic activity: | | |
|---|---|---|
| Compounds | $IC_{50}$ MCF7 (μmol/l) | $IC_{50}$ MDA468 (μmol/l) |
| 1, 2, 17 to 20, 23, 24, 27 to 29, 32 to 35, 38, 39, 41 to 43, 45 to 47, 50, 52, 53, 55 to 59, 61, 63, 65, 67 to 70, 78, 80, 81, 83, 85 and 87 | The inhibitory values of these listed Examples are ≦16.9 | The inhibitory values of these listed Examples are ≦13.6 |

Any or all of the compounds of formula I which are listed in one or more of the Tables A to H as well as their salts are a preferred subject in the present invention.

Chemosensitization Assay

The herein disclosed compounds are evaluated for the ability to sensitize cancer cells towards apoptotic stimuli. Compounds described in this invention are tested alone and in combination with chemotherapeutic and/or targeted cancer therapeutics to determine the effect on apoptosis induction. Cancer cells are seeded in 96 well plates at concentrations ranging from $2\times10^3$ to $1\times10^4$ cells per well in their respective growth media. 48-72 hours later, the apoptosis assay are set up as follows:

a) For combination assays with a chemotherapeutic agent like a topoisomerase inhibitor, such as e.g. camptothecin or camptothecin analogs, compounds are added at respective concentrations indicated and plates incubated at 37° C. in a $CO_2$ incubator for 18 hours. For standard combination assays uitilizing treatment with camptothecin are added at the same time at the respective concentrations indicated.

b) For combinations assays involving addition of pro-apoptotic agents like a death receptor agonist, such as e.g. TRAIL/Apo2L (Research Diagnostics), compounds are added for 1.5 hours prior to addition of TRAIL and plates incubated an additional 3 to 4 hours post TRAIL addition. In the case of the time course, plates are incubated for 2, 3, 4 and 6 hours with TRAIL ligand before ending the assay.

For both procedures, total final volumes do not exceed 250 μl. At the end of the incubation time, the cells are pelleted by centrifugation (200×g; 10 min. at RT) and the supernatant is discarded. The cells are resuspended and incubated using lysis buffer for 30 min. at RT (Cell Death Detection ELISA$^{PLUS}$, Roche, Cat. No. 11 774 425 001). After the centrifugation is repeated (200×g; 10 min. at RT) an aliquot of the supernatant are transferred to a streptavidin-coated well of a microplate. Followed by the incubation (2 h, RT) and binding of nucleosomes in the supernatant with two monoclonal antibodies, anti-histone (biotin-labeled) and anti-DNA (peroxidase-conjugated; Cell Death Detection ELISA$^{PLUS}$, Roche, Cat. No. 11 774 425 001). The antibody-nucleosome complexes are bound to the microplate. The immobilized antibody-histone complexes are washed three times at RT to remove cell components that are not immunoreactive. The substrate solution (ABTS; Cell Death Detection ELISA$^{PLUS}$, Roche, Cat. No. 11 774 425 001) are added and the samples were incubated for 15 min., RT. The amount of coloured product (and thus, of immobilized antibodyhistone complexes) is determined spectrophotometrically (absorbance at 405 nm). Data are expressed as percent activity of control with cisplatin used as a positive control. Apoptosis induction by 50 μM cisplatin is arbitrarily defined as 100 cisplatin units (100 CPU).

The invention claimed is:

1. A compound of formula I

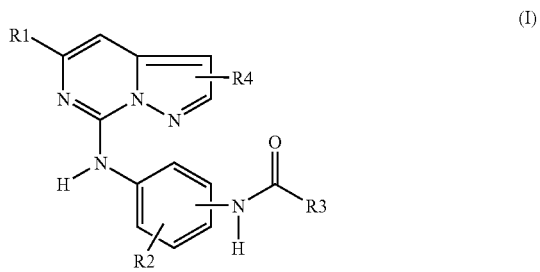

(I)

in which
R1 is Ar1, or
Har1, Har2 or Har3, or
Cyc1, or
Hh1, Ah1 or Ha1, in which
Ar1 is optionally substituted by R11, and is phenyl, naphthyl, fluorenyl or Aa1, in which
Aa1 is a bisaryl radical made up of two aryl groups, which are independently selected from the group consisting of phenyl and naphthyl, and which are linked together via a single bond,
R11 is 1-4C-alkoxy, 1-4C-alkoxy-2-4C-alkoxy, halogen, nitro, hydroxyl, phenoxy, phenyl-1-4C-alkoxy, hydroxy-2-4C-alkoxy, carboxy-1-4C-alkoxy or 1-4C-alkylcarbonylamino,
Har1 is optionally substituted by R12, and is an unsaturated monocyclic 5- or 6-membered heteroaryl radical comprising one to four heteroatoms, each of which is selected from the group consisting of nitrogen, oxygen and sulphur, in which
R12 is 1-4C-alkyl,
Har2 is optionally substituted by R13, and is an unsaturated fused bicyclic 9- or 10-membered heteroaryl radical comprising one to four heteroatoms, each of which is selected from the group consisting of nitrogen, oxygen and sulphur, in which R13 is 1-4C-alkyl, Har3 is optionally substituted by R14, and is an unsaturated fused tricyclic 13- or 14-membered heteroaryl radical comprising one to four heteroatoms, each of which is selected from the group consisting of nitrogen, oxygen and sulphur, in which R14 is 1-4C-alkyl, Cyc1 is a group of formula A

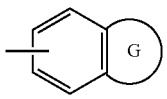

(A)

in which

G is a 5- or 6-membered saturated or partially unsaturated heterocyclic ring comprising one or two heteroatoms independently selected from the group consisting of oxygen and sulfur, whereby said Cyc1 ring system is attached to the parent molecular group via any substitutable carbon atom, Hh1 is optionally substituted by R15, and is a bisheteroaryl radical made up of two heteroaryl groups, which are independently selected from the group consisting of monocyclic 5- and 6-membered heteroaryl radicals comprising one or two heteroatoms, each of which is selected from the group consisting of nitrogen, oxygen and sulfur, and which are linked together via a single bond, in which R15 is 1-4C-alkyl, Ah1 is optionally substituted by R16, and is an arylheteroaryl radical made up of an aryl group selected from the group consisting of phenyl and naphthyl, and a heteroaryl group selected from the group consisting of monocyclic 5- and 6-membered heteroaryl radicals comprising one or two heteroatoms, each of which is selected from the group consisting of nitrogen, oxygen and sulfur, whereby said aryl and heteroaryl groups are linked together via a single bond, in which R16 is 1-4C-alkyl, Ha1 is optionally substituted by R17, and is a heteroarylaryl radical made up of a heteroaryl group selected from the group consisting of monocyclic 5- and 6-membered heteroaryl radicals comprising one or two heteroatoms, each of which is selected from the group consisting of nitrogen, oxygen and sulfur, and an aryl group selected from the group consisting of phenyl and naphthyl, whereby said heteroaryl and aryl groups are linked together via a single bond, in which R17 is 1-4C-alkyl, whereby each of the radicals Har1, Har2, Har3, Hh1 and Ah1 is bonded via a ring carbon atom to the pyrazolopyrimidine scaffold;

R2 is hydrogen, halogen or 1-4C-alkyl;

R3 is -T-R30, —U—Ar2, —V—Har4, or Cyc2, in which

T is 1-4C-alkylene,

R30 is —N(R301)R302, cyano, amidino, carbamoyl, guanidino, ureido, 1-4C-alkylsulfonyl, or Het2, in which R301 is hydrogen, 1-4C-alkyl, 1-4C-alkoxycarbonyl, hydroxy-2-4C-alkyl or 1-4C-alkoxy-2-4C-alkyl, R302 is hydrogen or 1-4C-alkyl, or R301 and R302 together and with inclusion of the nitrogen atom to which they are bonded form a radical Het1, in which Het1 is a monocylic 3- to 7-membered saturated heterocyclic ring comprising the nitrogen atom, to which R301 and R302 are attached, and optionally one further heteroatom selected from the group consisting of oxygen, nitrogen, N(R303) and sulfur, in which R303 is hydrogen, 1-4C-alkyl or 1-4C-alkoxycarbonyl, Het2 is a monocylic 3- to 7-membered saturated heterocyclic ring, which comprises one nitrogen atom and optionally one further heteroatom selected from the group consisting of oxygen, nitrogen, N(R304) and sulfur, whereby said Het2 radical is attached to the parent molecular group via a ring carbon atom, in which R304 is 1-4C-alkyl, U is a bond, 1-4C-alkylene, or 1-4C-alkylene substituted with amino-1-4C-alkyl, Ar2 is phenyl, or R31- and /or R32-substituted phenyl, in which R31 is 1-4C-alkyl, 1-4C-alkoxy, halogen, trifluoromethyl, or —W—R311, in which W is a bond or 1-4C-alkylene, R311 has one of the meanings of R30 as defined above, R32 is halogen, V is a bond, Har4 is optionally substituted by R33, and is a monocyclic or fused bicyclic 5- to 10-membered unsaturated heteroaryl radical comprising one to four heteroatoms, each of which is selected from the group consisting of nitrogen, oxygen and sulfur, whereby said Har4 radical is attached to the moiety V via a ring carbon atom, in which R33 is -Z-R331, in which Z is 1-4C-alkylene, R331 has one of the meanings of —N(R301)R302 as defined above, Cyc2 is a group of formula A

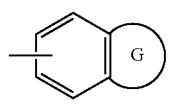

(A)

in which

G is a 5- or 6-membered saturated heterocyclic ring comprising one nitrogen atom and optionally one further heteroatom selected from the group consisting of oxygen, nitrogen and sulfur, whereby said Cyc2 ring system is attached to the parent molecular group via any substitutable carbon atom;

R4 is hydrogen or halogen;

or a salt thereof.

2. The compound of formula I according to claim 1 in which

R1 is Ar1, or

Har1, Har2 or Har3, or

Cyc1, or

Hh1, Ah1 or Ha1, in which

Ar1 is optionally substituted by R11, and is phenyl, naphthyl, fluorenyl or Aa1, in which Aa1 is a bisaryl radical made up of two aryl groups, which are independently selected from the group consisting of phenyl and naphthyl, and which are linked together via a single bond, R11 is 1-4C-alkoxy, 1-4C-alkoxy-2-4C-alkoxy, halogen, hydroxyl, phenoxy, phenyl-1-4C-alkoxy, hydroxy-2-4C-alkoxy, carboxy-1-4C-alkoxy or 1-4C-alkylcarbonylamino;

Har1 is optionally substituted by R12, and is an unsaturated monocyclic 5- or 6-membered heteroaryl radical comprising one to four heteroatoms, each of which is selected from the group consisting of nitrogen, oxygen and sulphur, in which R12 is 1-4C-alkyl, Har2 is optionally substituted by R13, and is an unsaturated fused bicyclic 9- or 10-membered heteroaryl radical comprising one to four heteroatoms, each of which is selected from the group consisting of nitrogen, oxygen and sulphur, in which R13 is 1-4C-alkyl, Har3 is optionally substituted by R14, and is an unsaturated fused tricyclic 13- or 14-membered heteroaryl radical comprising one to four heteroatoms, each of which is selected from the group consisting of nitrogen, oxygen and sulphur, in which R14 is 1-4C-alkyl, Cyc1 is a group of formula A

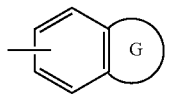

(A)

in which

G is a 5- or 6-membered saturated or partially unsaturated heterocyclic ring comprising one or two heteroatoms independently selected from the group consisting of oxygen and sulfur,
whereby said Cyc1 ring system is attached to the parent molecular group via any substitutable carbon atom, Hh1 is optionally substituted by R15, and is a bisheteroaryl radical made up of two heteroaryl groups, which are independently selected from the group consisting of monocyclic 5- and 6-membered heteroaryl radicals comprising one or two heteroatoms, each of which is selected from the group consisting of nitrogen, oxygen and sulfur, and which are linked together via a single bond, in which R15 is 1-4C-alkyl, Ah1 is optionally substituted by R16, and is an arylheteroaryl radical made up of an aryl group selected from the group consisting of phenyl and naphthyl, and a heteroaryl group selected from the group consisting of monocyclic 5- and 6-membered heteroaryl radicals comprising one or two heteroatoms, each of which is selected from the group consisting of nitrogen, oxygen and sulfur, whereby said aryl and heteroaryl groups are linked together via a single bond, in which R16 is 1-4C-alkyl, Ha1 is optionally substituted by R17, and is a heteroarylaryl radical made up of a heteroaryl group selected from the group consisting of monocyclic 5- and 6-membered heteroaryl radicals comprising one or two heteroatoms, each of which is selected from the group consisting of nitrogen, oxygen and sulfur, and an aryl group selected from the group consisting of phenyl and naphthyl, whereby said heteroaryl and aryl groups are linked together via a single bond, in which R17 is 1-4C-alkyl, whereby each of the radicals Har1, Har2, Har3, Hh1 and Ah1 is bonded via a ring carbon atom to the pyrazolopyrimidine scaffold;

R2 is hydrogen, halogen or 1-4C-alkyl;

R3 is -T-R30, —U—Ar2, —V-Har4, or Cyc2, in which

T is 1-4C-alkylene,

R30 is —N(R301)R302, cyano, amidino, carbamoyl, guanidino, ureido, or Het2, in which R301 is hydrogen, 1-4C-alkyl, 1-4C-alkoxycarbonyl, hydroxy-2-4C-alkyl or 1-4C-alkoxy-2-4C-alkyl, R302 is hydrogen or 1-4C-alkyl, or R301 and R302 together and with inclusion of the nitrogen atom to which they are bonded form a radical Het1, in which Het1 is a monocylic 3- to 7-membered saturated heterocyclic ring comprising the nitrogen atom, to which R301 and R302 are attached, and optionally one further heteroatom selected from the group consisting of oxygen, nitrogen, N(R303) and sulfur, in which R303 is hydrogen, 1-4C-alkyl or 1-4C-alkoxycarbonyl, Het2 is a monocylic 3- to 7-membered saturated heterocyclic ring, which comprises one nitrogen atom and optionally one further heteroatom selected from the group consisting of oxygen, nitrogen, N(R304) and sulfur, whereby said Het2 radical is attached to the parent molecular group via a ring carbon atom, in which R304 is 1-4C-alkyl, U is a bond, 1-4C-alkylene, or 1-4C-alkylene substituted with amino-1-4C-alkyl, Ar2 is phenyl, or R31- and /or R32-substituted phenyl, in which R31 is 1-4C-alkyl, 1-4C-alkoxy, halogen, trifluoromethyl, or —W—R311, in which W is a bond or 1-4C-alkylene, R311 has one of the meanings of R30 as defined above, R32 is halogen, V is a bond, Har4 is optionally substituted by R33, and is a monocyclic or fused bicyclic 5- to 10-membered unsaturated heteroaryl radical comprising one to four heteroatoms, each of which is selected from the group consisting of nitrogen, oxygen and sulfur, whereby said Har4 radical is attached to the moiety V via a ring carbon atom, in which R33 is -Z-R331, in which Z is 1-4C-alkylene, R331 has one of the meanings of —N(R301)R302 as defined above, Cyc2 is a group of formula A

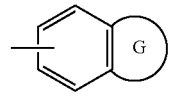

(A)

in which

G is a 5- or 6-membered saturated heterocyclic ring comprising one nitrogen atom and optionally one further heteroatom selected from the group consisting of oxygen, nitrogen and sulfur, whereby said Cyc2 ring system is attached to the parent molecular group via any substitutable carbon atom;

R4 is hydrogen;

or a salt thereof.

3. The compound according to claim 1, which is either from formula Ib or from formula Ic,

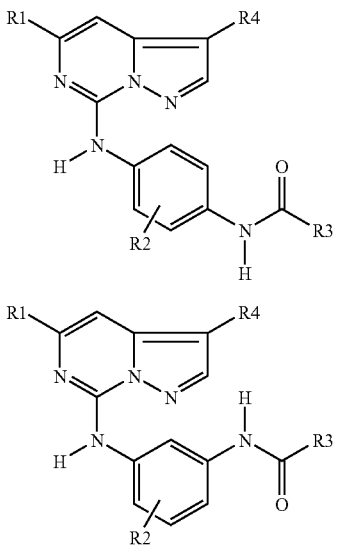

and in which
R1 is Ar1, or
Har3, or
Ah1 or Ha1, in which
Ar1 is optionally substituted by R11, and is phenyl, naphthyl or Aa1, in which
Aa1 is biphenyl,
R11 is 1-4C-alkoxy, 1-4C-alkoxy-2-4C-alkoxy, halogen, hydroxyl, nitro, phenoxy, phenyl-1-4C-alkoxy, hydroxy-2-4C-alkoxy, carboxy-1-4C-alkoxy or 1-4C-alkylcarbonylamino,
Har3 is dibenzofuranyl,
Ah1 is a phenyl-pyridyl radical,
Ha1 is optionally substituted by R17 on the pyrazolyl moiety, and is a pyrazolyl-phenyl radical, in which
R17 is 1-4C-alkyl;
R2 is hydrogen;
R3 is T-R30, —U—Ar2, —V-Har4, or Cyc2, in which
T is 1-4C-alkylene,
R30 is —N(R301)R302, in which
R301 is hydrogen, 1-4C-alkyl or hydroxy-2-4C-alkyl,
R302 is hydrogen or 1-4C-alkyl,
either
U is a bond,
Ar2 is R31-substituted phenyl, or R31- and R32-substituted phenyl, in which
R31 is amidino, guanidino, Het2 or —W—R311, in which
Het2 is piperidinyl or pyrrolidinyl,
whereby said Het2 radical is attached to the parent molecular group via a ring carbon atom,
W is a bond or 1-4C-alkylene,
R311 has one of the meanings of R30 as defined above and
R32 is halogen,
or
U is 1-4C-alkylene substituted with amino-1-4C-alkyl,
Ar2 is R31- and R32-substituted phenyl, in which
R31 is halogen, and
R32 is halogen,
V is a bond, Har4 is R33-substituted pyridyl, R33-substituted thiophenyl
or R33-substituted furanyl, in which
R33 is -Z-R331, in which
Z is 1-4C-alkylene,
R331 has one of the meanings of R30 as defined above,
Cyc2 is

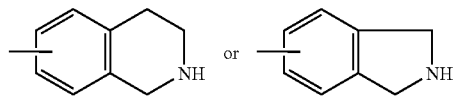

whereby the substituent —N(H)C(O)R3 is attached in the meta or para position with respect to the binding position in which the phenyl ring is bonded to the pyrazolopyrimidinyl-amino moiety;
R4 is hydrogen or bromine;
or a salt thereof.

4. The compound according to claim 1, which is either from formula Ib or from formula Ic

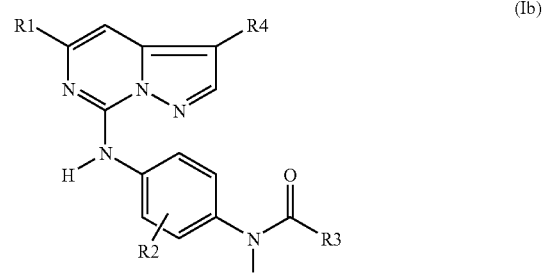

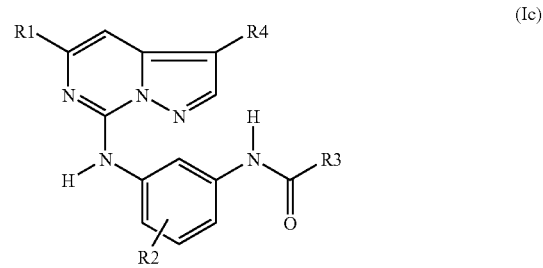

and in which
R1 is Ar1, or
Har3, or
Ah1 or Ha1, in which
either
Ar1 is naphthalen-2-yl or 6-(R11)-naphthalen-2-yl, in which
R11 is 1-2C-alkoxy, 2-methoxyethoxy, hydroxyl, benzyloxy or 2-hydroxyethoxy,
or
Ar1 is biphen-3-yl, biphen-4-yl, 2'-(R11)-biphen-3-yl, 3'-(R11)-biphen-3-yl, 4'-(R11)-biphen-3-yl, 2'-(R11)-biphen-4-yl, 3'-(R11)-biphen-4-yl or 4'-(R11)-biphen-4-yl, in which
R11 is 1-2C-alkoxy, nitro, 1-2C-alkylcarbonylamino or halogen, or
  Ar1 is 3-(R11)-phenyl or 4-(R11)-phenyl, in which
    R11 is halogen,
  Har3 is dibenzofuran-4-yl,
  Ah1 is phenyl-pyridyl,
  Ha1 is 3-(pyrazol-1-yl)-phenyl, 3-(1N—H-pyrazolyl)-phenyl, 3-[1N-(1-2C-alkyl)-pyrazolyl]-phenyl, 4-(pyrazol-1-yl)-phenyl, 4-(1N—H-pyrazolyl)-phenyl or 4-[1N-(1-2C-alkyl)-pyrazolyl]-phenyl;
  R2 is hydrogen;
  R3 is -T-R30, —U—Ar2, —V-Har4, or Cyc2, in which
    T is 1-4C-alkylene,
    R30 is amino,
either
  U is a bond, and
  Ar2 is 2-(R31)-phenyl, 3-(R31)-phenyl or 4-(R31)-phenyl, in which
    R31 is amino,
or
  U is a bond, and
  Ar2 is 3-(R31)-phenyl or 4-(R31)-phenyl, in which
    R31 is guanidino, amidino or 1N—H-piperidinyl,
or
  U is a bond, and
  Ar2 is 3-(R31)-phenyl, 4-(R31)-phenyl, R32-substituted 3-(R31)-phenyl, or R32-substituted 4-(R31)-phenyl, in which
    R31 is —W—R311, in which
      W is 1-4C-alkylene,
      R311 is —N(R301)R302, in which
        R301 is hydrogen, 1-2C-alkyl or 2-hydroxyethyl,
        R302 is hydrogen, and
    R32 is fluorine,
or
  U is 1-4C-alkylene substituted with amino-1-4C-alkyl, and
  Ar2 is R31- and R32-substituted phenyl, in which
    R31 is chlorine, and
    R32 is chlorine,
  V is a bond,
  Har4 is R33-substituted pyridyl, or R33-substituted furanyl, in which
    R33 is -Z-R331, in which
      Z is 1-4C-alkylene,
      R331 is amino,
  Cyc2 is any one of the following radicals:

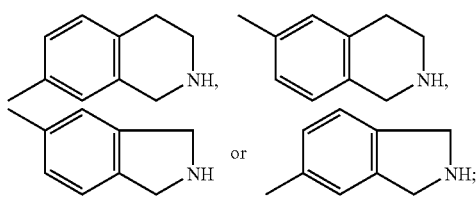

R4 is hydrogen or bromine;
or a salt thereof.

5. The compound according to claim 1, which is either from formula Ib or from formula Ic

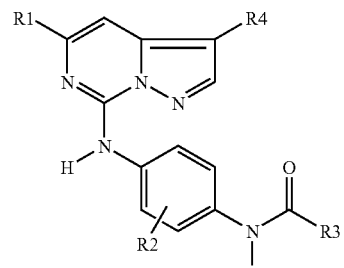

(Ib)

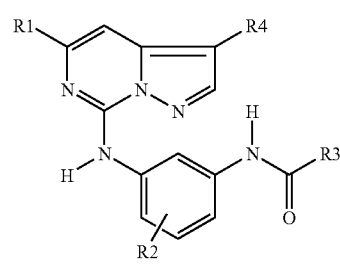

(Ic)

and in which
  R1 is Ar1, or
    Har3, or
    Ah1 or Ha1, in which
either
  Ar1 is naphthalen-2-yl, or 6-(R11)-naphthalen-2-yl, in which
    R11 is 1-2C-alkoxy, 2-methoxyethoxy, hydroxyl, benzyloxy or 2-hydroxyethoxy,
or
  Ar1 is biphen-3-yl, biphen-4-yl, 2'-(R11)-biphen-4-yl, 3'-(R11)-biphen-4-yl, 4'-(R11)-biphen-4-yl, 3'-(R11)-biphen-3-yl or 4'-(R11)-biphen-3-yl, in which
    R11 is 1-2C-alkoxy, nitro, fluorine or 1-2C-alkylcarbonylamino,
or
  Ar1 is 3-(R11)-phenyl or 4-(R11)-phenyl, in which
    R11 is bromine or iodine,
  Har3 is dibenzofuran-4-yl,
  Ah1 is 6-phenyl-pyridin-3-yl,
  Ha1 is 4-[1N-(1-2C-alkyl)-pyrazol-4-yl]-phenyl;
  R2 is hydrogen;
  R3 is -T-R30, —U—Ar2, —V-Har4, or Cyc2, in which
    T is straight chain 1-4C-alkylene,
    R30 is amino,
either
  U is a bond, and
  Ar2 is 4-(R31)-phenyl or 3-(R31)-phenyl, in which
    R31 is guanidino, or
  U is a bond, and
  Ar2 is 4-(R31)-phenyl, 3-(R31)-phenyl or 2-fluoro-4-(R31)-phenyl, in which
    R31 is —W—R311, in which
      W is methylene or ethylene,
      R311 is —N(R301)R302, in which
        R301 is hydrogen, methyl or 2-hydroxyethyl,
        R302 is hydrogen,
or
  U is methylene substituted with amino-1-2C-alkyl, and
  Ar2 is 3,4-dichloro-phenyl,
  V is a bond, Har4 is R33-substituted pyridyl, or R33-substituted furanyl, in which
R33 is -Z-R331, in which
Z is methylene,
R331 is amino,
Cyc2 is 1,2,3,4-tetrahydroisoquinolin-6-yl or 1,2,3,4-tetrahydroisoquinolin-7-yl;
R4 is hydrogen or bromine;
or a salt thereof.

6. The compound according to claim 1, which is either from formula Ib or from formula Ic,

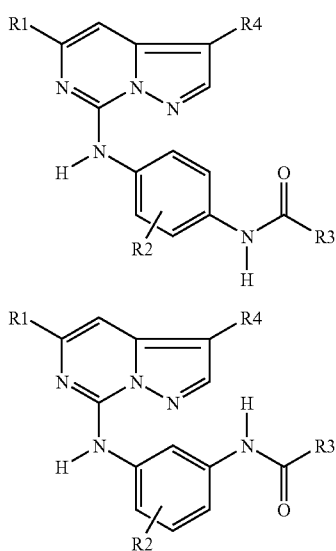

and in which
R1 is Ar1, or
Har3, or
Ah1 or Ha1, in which
either
Ar1 is 6-(R11)-naphthalen-2-yl, in which
R11 is 1-2C-alkoxy, 2-methoxyethoxy, hydroxyl, benzyloxy or 2-hydroxyethoxy,
or
Ar1 is biphen-3-yl, biphen-4-yl, 2'-(R11)-biphen-4-yl, 3'-(R11)-biphen-4-yl, 4'-(R11)-biphen-4-yl, 3'-(R11)-biphen-3-yl or 4'-(R11)-biphen-3-yl, in which
R11 is methoxy, fluorine, acetylamino or nitro,
Har3 is dibenzofuran-4-yl,
Ah1 is 6-phenyl-pyridin-3-yl,
Ha1 is 4-(1N-methyl-pyrazol-4-yl)-phenyl;
R2 is hydrogen;
R3 is —U—Ar2, —V-Har4, or Cyc2, in which
either
U is a bond, and
Ar2 is 4-(R31)-phenyl or 3-(R31)-phenyl, in which
R31 is guanidino,
or
U is a bond, and
Ar2 is 4-(R31)-phenyl, 3-(R31)-phenyl or 2-fluoro-4-(R31)-phenyl, in which
R31 is —W—R311, in which
W is methylene or ethylene,
R311 is —N(R301)R302, in which
R301 is hydrogen or methyl,
R302 is hydrogen,
V is a bond,
Har4 is 6-(aminomethyl)-pyridin-3-yl, 2-(aminomethyl)-pyridin-4-yl, 6-(aminomethyl)-pyridin-2-yl, 5-(aminomethyl)-pyridin-3-yl, 5-(aminomethyl)-pyridin-2-yl, or 5-(aminomethyl)-furan-2-yl,
Cyc2 is 1,2,3,4-tetrahydroisoquinolin-6-yl or 1,2,3,4-tetrahydroisoquinolin-7-yl;
R4 is hydrogen;
or a salt thereof.

7. The compound according to claim 1, which is either from formula Ib or from formula Ic

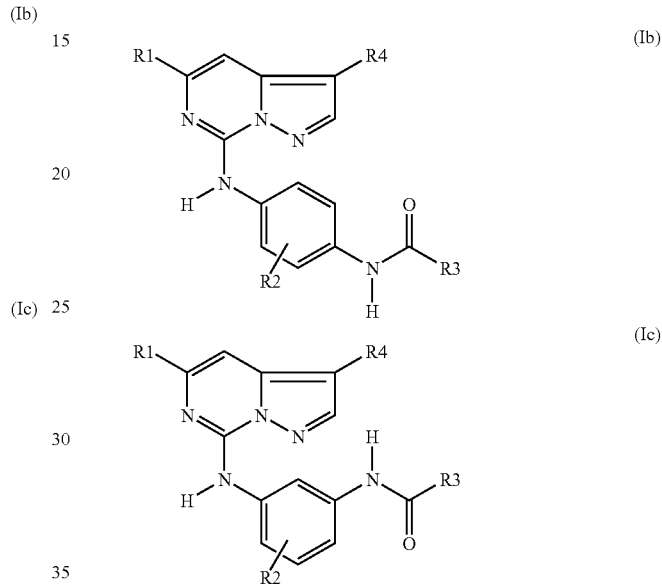

and in which
R1 is Ar1, or
Har3, or
Ah1 or Ha1, in which
either
Ar1 is 6-(R11)-naphthalen-2-yl, in which
R11 is 1-2C-alkoxy, 2-methoxyethoxy, hydroxyl, benzyloxy or 2-hydroxyethoxy,
or
Ar1 is biphen-3-yl, biphen-4-yl, 2'-(R11)-biphen-4-yl, 3'-(R11)-biphen-4-yl, 4'-(R11)-biphen-4-yl, 3'-(R11)-biphen-3-yl or 4'-(R11)-biphen-3-yl, in which
R11 is methoxy, fluorine, acetylamino or nitro,
Har3 is dibenzofuran-4-yl,
Ah1 is 6-phenyl-pyridin-3-yl,
Ha1 is 4-(1N-methyl-pyrazol-4-yl)-phenyl;
R2 is hydrogen;
R3 is —U—Ar2, —V-Har4, or Cyc2, in which
either
U is a bond, and
Ar2 is 4-(R31)-phenyl or 3-(R31)-phenyl, in which
R31 is guanidino,
or
U is a bond, and
Ar2 is 4-(R31)-phenyl, 3-(R31)-phenyl or 2-fluoro-4-(R31)-phenyl, in which
R31 is —W—R311, in which
W is methylene or ethylene,
R311 is —N(R301)R302, in which
R301 is hydrogen or methyl, R302 is hydrogen,
V is a bond,
Har4 is 6-(aminomethyl)-pyridin-3-yl, 2-(aminomethyl)-pyridin-4-yl, 6-(aminomethyl)-pyridin-2-yl, 5-(aminomethyl)-pyridin-3-yl, 5-(aminomethyl)-pyridin-2-yl, or 5-(aminomethyl)-furan-2-yl,
Cyc2 is 1,2,3,4-tetrahydroisoquinolin-6-yl or 1,2,3,4-tetrahydroisoquinolin-7-yl;
R4 is bromine;
or a salt thereof.

8. The compound according to claim 2, which is either from formula Ib or from formula Ic

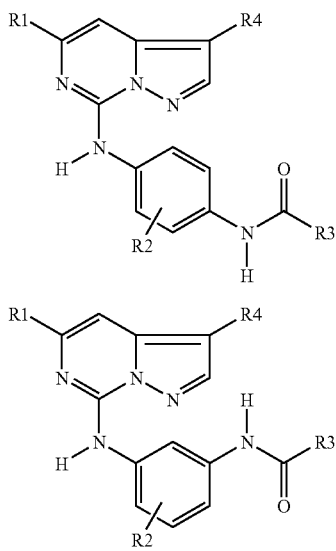

and in which
R1 is Ar1, or
Har3, or
Ha1, in which
either
Ar1 is 6-(R11)-naphthalen-2-yl, in which
R11 is 1-2C-alkoxy, 2-methoxyethoxy, hydroxyl, benzyloxy or 2-hydroxyethoxy,
or
Ar1 is biphen-4-yl, 3'-acetylamino-biphen-4-yl, 2'-(R11)-biphen-4-yl, 3'-(R11)-biphen-4-yl, or 4'-(R11)-biphen-4-yl, in which
R11 is methoxy, or fluorine,
Har3 is dibenzofuran-4-yl,
Ha1 is 4-(1N-methyl-pyrazol-4-yl)-phenyl;
R2 is hydrogen;
R3 is —U—Ar2, —V-Har4, or Cyc2, in which
either
U is a bond, and
Ar2 is 4-(R31)-phenyl, in which
R31 is guanidino,
or
U is a bond, and
Ar2 is 4-(R31)-phenyl, 3-(R31)-phenyl, or 2-fluoro-4-(R31)-phenyl, in which
R31 is —W—R311, in which
W is methylene or ethylene,
R311 is —N(R301)R302, in which
R301 is hydrogen or methyl,
R302 is hydrogen,
V is a bond,
Har4 is 6-(aminomethyl)-pyridin-3-yl, 2-(aminomethyl)-pyridin-4-yl, 6-(aminomethyl)-pyridin-2-yl, 5-(aminomethyl)-pyridin-3-yl, 5-(aminomethyl)-pyridin-2-yl, or 5-(aminomethyl)-furan-2-yl,
Cyc2 is 1,2,3,4-tetrahydroisoquinolin-6-yl or 1,2,3,4-tetrahydroisoquinolin-7-yl;
R4 is hydrogen;
or a salt thereof.

9. The compound according to claim 1, which is either from formula Ib or from formula Ic

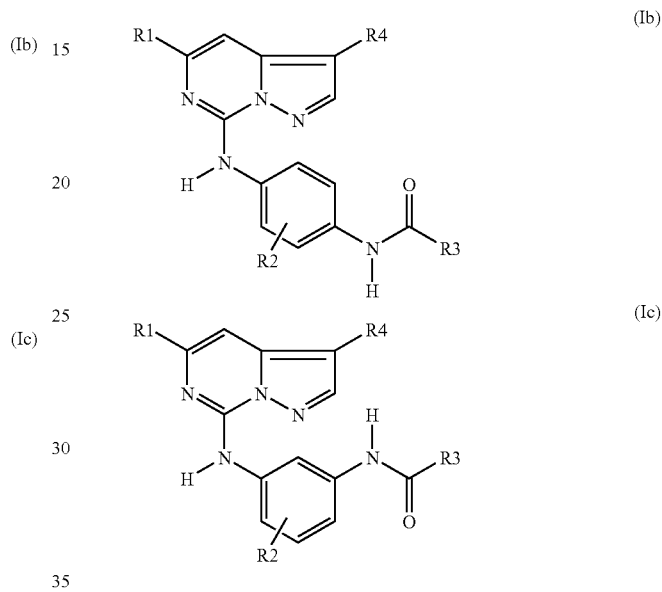

and in which
R1 is selected from the group consisting of Ar1, Har3, Ah1 and Ha1,
in which
either
Ar1 is naphthalen-2-yl, or 6-(R11)-naphthalen-2-yl, in which
R11 is methoxy, ethoxy, 2-methoxyethoxy, hydroxyl, benzyloxy or 2-hydroxyethoxy,
or
Ar1 is biphen-4-yl, biphen-3-yl, 2'-(R11)-biphen-4-yl, 3'-(R11)-biphen-4-yl, 4'-(R11)-biphen-4-yl, 3'-(R11)-biphen-3-yl or 4'-(R11)-biphen-3-yl, in which
R11 is methoxy, fluorine, nitro or acetylamino,
Har3 is dibenzofuran-4-yl,
Ah1 is phenyl-pyridinyl,
Ha1 is (1N-methyl-pyrazolyl)-phenyl;
R2 is hydrogen; and
R3 is selected from the group consisting of -T-R30, —U—Ar2, —V-Har4 and Cyc2, in which
T is straight chain 1-4C-alkylene,
R30 is amino,
either
U is a bond, and
Ar2 is 4-(R31)-phenyl, or 3-(R31)-phenyl, in which
R31 is guanidino,
or
U is a bond, and
Ar2 is 4-(R31)-phenyl, 3-(R31)-phenyl or 2-fluoro-4-(R31)-phenyl, in which
R31 is —W—R311, in which W is methylene or ethylene,
R311 is —N(R301)R302, in which
R301 is hydrogen, methyl or 2-hydroxyethyl,
R302 is hydrogen,
V is a bond,
Har4 is R33-substituted pyridyl, or R33-substituted furanyl, in which
R33 is -Z-R331, in which
Z is methylene,
R331 is amino,
Cyc2 is 1,2,3,4-tetrahydroisoquinolin-6-yl or 1,2,3,4-tetrahydroisoquinolin-7-yl;
or a salt thereof.

10. The compound, which is either from formula Ib or from formula Ic

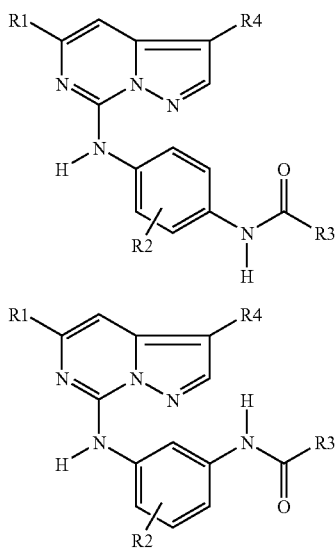

and in which
R1 is selected from the group consisting of:
biphen-4-yl, biphen-3-yl, 4'-methoxy-biphen-4-yl, 3'-methoxy-biphen-4-yl, 2'-methoxy-biphen-4-yl, 4'-fluoro-biphen-4-yl, 3'-fluoro-biphen-4-yl, 2'-fluoro-biphen-4-yl, 3'-acetylamino-biphen-4-yl, 3'-nitro-biphen-4-yl, 4'-methoxy-biphen-3-yl, 3'-methoxy-biphen-3-yl, 3'-acetylamino-biphen-3-yl, 6-methoxy-naphthalen-2-yl, 6-ethoxy-naphthalen-2-yl, 6-(2-methoxyethoxy)-naphthalen-2-yl, 6-hydroxy-naphthalen-2-yl, 6-benzyloxy-naphthalen-2-yl, 6-(2-hydroxyethoxy)-naphthalen-2-yl, 4-[1N-methyl-pyrazol-4-yl]-phenyl, 6-phenyl-pyridin-3-yl, and dibenzofuran-4-yl;
R2 is hydrogen; and
R3 is selected from the group consisting of:
4-(aminomethyl)-phenyl, 3-(aminomethyl)-phenyl, 4-(2-aminoethyl)-phenyl, 3-aminopropyl, 2-fluoro-4-(aminomethyl)-phenyl, 4-(N-methyl-aminomethyl)-phenyl, 1,2,3,4-tetrahydroisoquinolin-6-yl, 1,2,3,4-tetrahydroisoquinolin-7-yl-4-guanidino-phenyl, 4-[N-(2-hydroxyethyl)-aminomethyl]-phenyl, 6-(aminomethyl)-pyridin-3-yl, 2-(aminomethyl)-pyridin-4-yl, 6-(aminomethyl)-pyridin-2-yl, 5-(aminomethyl)-pyridin-3-yl, 5-(aminomethyl)-pyridin-2-yl, and 5-(aminomethyl)-furan-2-yl;
or a salt thereof.

11. A pharmaceutical composition comprising a therapeutically effective amount of one or more compounds according to claim 1, or a salt thereof, together with a pharmaceutically acceptable carrier or diluent.

12. A combination comprising
a first active ingredient, which is at least one compound according to claim 1, or a salt thereof, and
a second active ingredient, which is at least one anti-cancer agent selected from the group consisting of chemotherapeutic anti-cancer agents and target-specific anti-cancer agents,
for separate, sequential, simultaneous, concurrent or chronologically staggered use in chemotherapeutic therapy.

13. The combination according to claim 12, in which said chemotherapeutic anti-cancer agents are selected from (i) alkylating/carbamylating agents; (ii) platinum derivatives; (iii) antimitotic agents/tubulin inhibitors; (iv) topoisomerase inhibitors; (v) pyrimidine antagonists; (vi) purin antagonists; and (vii) folic acid antagonists.

14. The combination according to claim 12, in which said target-specific anti-cancer agents are selected from (i) kinase inhibitors; (ii) proteasome inhibitors; (iii) histone deacetylase inhibitors; (iv) heat shock protein 90 inhibitors; (v) vascular targeting agents (VAT); (vi) monoclonal antibodies Trastuzumab, Rituximab, Alemtuzumab, Tositumomab, Cetuximab and Bevacizumab, as well as mutants and conjugates of monoclonal antibodies Gemtuzumab ozogamicin or Ibritumomab tiuxetan; (vii) oligonucleotide based therapeutic Oblimersen; (viii) Toll-like receptor/TLR 9 agonists; (ix) protease inhibitors; (x) anti-estrogens hormonal therapeutics; (xi) anti-androgens hormonal therapeutics; (xii) luteinizing-hormone releasing hormone (LHRH) agents Leuprorelin, Goserelin or Triptorelin; (xiii) aromatase inhibitors; (xiv) bleomycin; (xv) retinoids; (xvi) DNA methyltransferase inhibitors; (xvii) alanosine; (xviii) cytokines; (xix) interferons; and (xx) death receptor agonists.

* * * * *

UNITED STATES PATENT AND TRADEMARK OFFICE
CERTIFICATE OF CORRECTION

PATENT NO. : 7,745,446 B2
APPLICATION NO. : 11/661111
DATED : June 29, 2010
INVENTOR(S) : Thomas Maier et al.

It is certified that error appears in the above-identified patent and that said Letters Patent is hereby corrected as shown below:

Column 89, Claim 10, Line 15:
Please delete "compound, which" and replace with -- compound according to claim 1, which --

Column 90, Claim 10, Lines 9-10:
Please delete "1,2,3,4-tetrahydroisoquinolin-7-yl-4-guanidino-phenyl" and replace with
-- 1,2,3,4-tetrahydroisoquinolin-7-yl --

Signed and Sealed this

Seventeenth Day of August, 2010

David J. Kappos
*Director of the United States Patent and Trademark Office*